US006703485B2

(12) United States Patent
Kandel et al.

(10) Patent No.: US 6,703,485 B2
(45) Date of Patent: Mar. 9, 2004

(54) BRAIN AND HEART CYCLIC NUCLEOTIDE GATED ION CHANNEL COMPOUNDS AND USES THEREOF

(75) Inventors: Eric R. Kandel, Riverdale, NY (US); Bina Santoro, Rome (IT); Dusan Bartsch, New York, NY (US); Steven Siegelbaum, New York, NY (US); Gareth Tibbs, New York, NY (US); Seth Grant, Edinburgh (GB)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/086,436

(22) Filed: May 28, 1998

(65) Prior Publication Data

US 2003/0118988 A1 Jun. 26, 2003

Related U.S. Application Data

(63) Continuation-in-part of application No. 08/997,685, filed on Dec. 23, 1997, now Pat. No. 6,551,821.

(51) Int. Cl.[7] ............................ C07K 1/00; C12Q 1/68; C12N 5/02; C07H 21/02

(52) U.S. Cl. ........................... 530/350; 435/6; 435/325; 435/354; 435/366; 435/375; 536/23.1

(58) Field of Search ............................ 435/6, 325, 354, 435/366, 375; 536/23.1, 24.1; 530/300, 350, 386, 387.1

(56) References Cited

U.S. PATENT DOCUMENTS 5,194,596 A * 3/1993 Tischer
5,350,836 A * 9/1994 Kopchick et al.

OTHER PUBLICATIONS

Genetwork, TIG Oct. 1996 vol. 12, No. 10, pp. 425–427.*

Errors in genome annotation, TIG Apr. 1999, vol. 15, No. 4, pp. 132–133.*

Temple F. Smith et al., The challenges of genome sequence annotation or "The devil is in the details", Nature Biotechnology, vol. 15, Nov. 1997, pp. 1222–1223.*

C.C.Pilbeam et al., Comparison of the Effects of Various Lengths of Synthetic Human Parathyroid Hormone–Related Peptide (hPTHrP) of Malignancy on Bone Resorption and Formation in Organ Culture, Bone, 14, pp. 717–720.*

(List continued on next page.)

*Primary Examiner*—Karen A. Lacourciere
*Assistant Examiner*—Terra C. Gibbs
(74) *Attorney, Agent, or Firm*—John P. White; Cooper & Dunham LLP

(57) ABSTRACT

The present invention provides an isolated nucleic acid encoding a BCNG protein or a portion thereof or BCNG-related protein or a portion thereof. The present invention further provides a method for identifying a nucleic acid in a sample which encodes a BCNG protein or a BCNG-related protein. The present invention also provides a method for testing whether a compound affects the expression of a BCNG protein or a BCNG-related protein. In addition, the present invention further provides a method for identifying a compound capable of interacting with a BCNG protein or a BCNG-related protein. Also, the present invention provides a method for identifing a compound capable of modulating BCNG protein or BCNG-related protein activity. Further, the present invention also provides a method of treating a condition in a subject which comprises administering to the subject an amount of the provided compound, effective to treat the condition.

2 Claims, 31 Drawing Sheets

OTHER PUBLICATIONS

Slobodan Vukicevic et al., Induction of nephrogenic mesenchyme by osteogenic protein 1 (bone morphogenetic protein 7), Proc. Natl. Acad. Sci. USA, vol. 93, pp. 9021–9026.*

Laura E. Benjamin et al., A plasticity window for blood vessel remodeling is defined by pericyte coverage of the performed endothelial network and is regulated by PDGF–B and VEGF, Development 125, pp. 1591–1598.*

Genetwork, Protein annotation: detective work for function prediction, TIG Jun. 1998 vol. 14, No. 6, pp. 248–250.*

Jeffrey Skolnick et al., From genes to protein structure and function: novel applications of computational approaches in the genomic era, Trends in Biotech, 18 (1): pp. 34–39.*

Peer Bork, Powers and Pitfalls in Sequence Analysis: The 70% Hurdle, Genome Research, pp. 398–400.*

James A. Wells, Additivity of Mutational Effects in Proteins, Biochemistry, vol. 29, No. 37, Sep. 18, 1990, pp. 8509–8517.*

J. Thomas Ngo et al., Computational Complexity, Protein Structure Prediction, and the Levinthal Paradox, pp. 491–495.*

Ruth Keller et al., Antisense inhibition of the GDP–mannose pyrophosphorylase reduces the ascorbate content in transgenic plants leading to developmental changes during senescence, The Plant Journal (1999) 19(2), pp. 131–141.*

Santoro et al, Cell vol. 93, pp 717–729, Jun. 8, 1998.*

Ludwig et al, Nature vol. 393, pp 587–591, Jun. 22, 1998.*

Adelman, J. P. et al. (1992) "Calcium–Activated Potassium Channels Expressed from Cloned Complementary DNAs," *Neuron*, 9: 209–216.

Adelman J. P. (1995) "Protein that Interact with the Pore–Forming Subunits of Voltage–Gated Ion Channels," *Current Opinion in Neurobiology*, 5(3): 286–295.

Aiba, H. et al. (1982) "Molecular Cloning and Nucleotide Sequencing of the Gene for *E. Coli* cAMP Receptor Protein," *Nucleic Acids Res.*, 10(4): 1345–1361.

Arancio, O. et al. (1995) "Activity–Dependent Long–Term Enhancement of Trasmitter Release by Presynaptic 3' ,5'–Cyclic GMP in Cultured Hippocampal Neurons," *Nature*, 376: 74–80.

Atkinson, N. S. et al. (1991) "A Component of Calcium–Activated Potassium Channels Encoded by the Drosophila slo Locus," *Science*, 253(5019): 551–555.

Bolshakov, V. Y. (1997) "Recruitment of New Sites of Synaptic Transmission During the cAMP–Dependent Late Phase of LTP at CA3–CA1 Synapses in the Hippocampus," *Neuron*, 19: 635–651.

Bradley, J. et al. (1997) "Functional Expression of the Heteromeric 'Olfactory' Cyclic Nucleotide–Gated Channel in the Hippocampus: A Potential Effector of Synpaptic Plasticity in Brain Neurons," *J. of Neurosci.*, 17(6): 1993–2005.

Bradley, J. et al. (1994) "Heteromeric Olfactory Cyclic Nucleotide–Gated Channels: A Subunit That Confers Increased Sensitivity to cAMP," *Proc. Natl. Acad. Sci. USA*, 91: 8890–8894.

Brugge, J. S. et al. (1985) "Neurones Express High Levels of a Structurally Modified Activated Form of $pp60^{c-src}$," *Nature*, 316: 554–557.

Bruggemann, A. et al. (1993) "Ether–a–go–go Encodes a Voltage–Gated Channel Permeable to $K^+$ and $Ca^{2+}$ and Modulated by cAMP," *Nature*, 365: 445–448.

Chen, T. Y. et al. (1993) "A New Subunit of the Cyclic Nucleotide–Gated Cation Channel in Retinal Rods," *Nature*, 362: 764–767.

Erickson, P. F. et al. (1982) "Quantitative Electrophoretic Transfer of Polypeptides from SDS Polyacrylamide Gels to Nitrocellulose Sheets: A Method for Their Re–Use in Immunoautoradiographic Detection of Antigens," *J. Immunol. Methods*, 51: 241–249.

Fields, S. et al. (1989) "A Novel Genetic System to Detect Protein–Protein Interactions," *Nature*, 340: 245–246.

Frey, U. et al. (1993) "Effects of cAMP Simulate a Late Stage of LTP in Hippocampal CA1 Neurons," *Science*, 260: 1661–1664.

Green, W. N. et al. (1995) "Ion–Channel Assembly," *Trends In Neurosci.*, 18: 280–287.

Hoshi, T. (1995) "Regulation of Voltage Dependence of KAT1 Channel by Intracellular Factors," *J. Gen. Physiol.*, 105: 309–328.

Ingram, S. L. et al. (1996) "Modulation of the Hyperpolarization–Activated Current ($I_h$) by Cyclic Nucleotides in Guinea–Pig Primary Afferent Neurons," *J. Physiol.*, 492: 97–227.

Jenkins, Y. et al. (1992) "A Sequence–Specific Molecular Light Switch: Tethering of an Oligonucleotide to a Dipyridophenazine Complex of Ruthenium(II)," *J. Am. Chem. Soc.*, 114(22): 8736–8738.

Kamb, A. et al. (1987) "Molecular Characterization of Shaker, a Drosophila Gene That Encodes a Potassium Channel," *Cell*, 50(3): 405–413.

Kaupp, U. B. et al. (1989) "Primary Structure and Functional Expression from Complementary DNA of the Rod Photoreceptor Cyclic GMP–Gated Channel," *Nature*, 342: 762–766.

Kohler, M. et al. (1996) "Small–Conductance, Calcium–Activated Potassium Channels from Mammalian Brain," *Science*, 273: 1709–1714.

Krapivinsky, G. et al. (1995) "$G_{\beta\rho}$Binds Directly to G Protein–Gated $K^+$Channel, $I_{KACh}$," *J. Biol. Chem.*, 270: 29059–29062.

Lidofsky, S. D. (1996) "Regulation of Cation–Selective Channels in Liver Cells," *J. Membr. Biol.*, 157: 231–236.

Liman, E. R. et al. (1994) "A Second Subunit of the Olfactory Cyclic Nucleotide–Gated Channel Confers High Sensitivity to cAMP," *Neuron*, 13: 611–621.

Martinez, R. (1987) "Neuronal $pp60^{c-src}$ Contains a Six–Amino Acid Insertion Relative to Its Non–Neuronal Counterpart," *Science*, 237: 411–415.

Matthaei, F. S. et al. (1986) "Rapid and Effective Transfer of Integral Membrane Proteins from Isoelectric Focusing Gels to Nitrocellulose Membranes," *Anal. Biochem.*, 157: 123–128.

Marunaka, Y. et al. (1991) "Cyclic GMP–Activated Channel Activity in Renal Epithelial Cells (A6)," *Biochim. Biophys. Acta*, 1070: 152–156.

Pallanck, L. & Ganetzky, B. (1994) "Cloning and Characterization of Human and Mouse Homologs of the Drosophila Calcium–Activated Potassium Channel Gene, Slowpoke," *Hum. Mol. Genet.*, 3: 1239–1243.

Papazian, D. M. et al. (1991) "Alteration of Voltage–Dependence of Shaker Potassium Channel by Mutations in the S4 Sequence," *Nature*, 349(24): 305–310.

Papazian, D. M. et al. (1987) "Cloning of Genomic and Complementary DNA from Shaker, a Putative Potassium Channel Gene from Drosophila," *Science*, 237: 749–753.

Pawson, T. (1995) "Protein Modules and Signalling Networks," *Nature*, 373(16): 573–5.
Pedarzani, P. et al. (1995) "Protein Kinase A–Independent Modulation of Ion Channels in the Brain by Cyclic AMP," *Proc. Natl. Acad. Sci. USA*, 92: 11716–11720.
Santoro, B. et al. (1997) "Interactive Cloning with the SH3 Domain of N–src Identifies a New Brain Specific Ion Channel Protein, with Homology to Eag and Cyclic Nucleotide–Gated Channels," *Proc. Natl. Acad. Sci. USA*, 94: 14815–14820.
Sheng, M. et al. (1994) "Contrasting Subcellular Localization of the Kv1.2 $K^+$ Channel Subunit in Different Neurons of Rat Brain," *J. Neurosci.*, 14(4): 2408–2417.
Staub, O. et al. (1996) "WW Domain of Nedd4 Bind to the Proline–Rich PY Motifs in the Epithelial $Na^+$ Channel Deleted in Liddle's Syndrome," *EMBO J.*, 15(10): 2371–2380.
Strong, M. et al. (1993) "Molecular Evolution of Voltage–Sensitive Ion Channel Genes: On the Origins of Electrical Excitability," *Mol. Biol. Evol.*, 10(1): 221–242.
Studol, M. (1996) "The WW Module Competes with the SH3 Domain?" *Trends in Biochem. Sci.*, 21: 161–163.
Sugrue, M. M. et al. (1990) "Immunocytochemical Localization of the Neuron–Specific Form of the c–src Gene Product, $pp60^{c-src(+)}$, in Rat Brain," *J. Neurosci.*, 10(8): 2513–2527.
Thomas, M. J. et al. (1996) "Activity–Dependent β–Adrenergic Modulation of Low Frequency Stimulation Induced LTP in the Hippocampal CA1 Region," *Neuron*, 17: 475–482.
Wang, H. et al. (1994) "Localization of Kv1.2, Two K Channel Proteins, to Synaptic Terminals, Somata, and Dendrites in the Mouse Brain," *J. Neurosci.*, 14: 4588–4599.

Warmke, J. W. et al. (1991) "A Family of Potassium Channel Genes Related to Eag in Drosophila and Mammals," *Science*, 91: 3438–3442.

Warmke, J. W. et al. (1991) "A Distinct Potassium Channel Polypeptide Encoded by the Drosophila Eag Locus," *Proc. Natl. Acad. Sci. USA*, 252(5012): 1560–1562.

Weber, I. T. et al. (1989) "Predicted Structures of the cGMP Binding Domains of the cGMP–Dependent Protein Kinase: A Key Alanine/Threonine Difference in Evolutionary Divergence of cAMP and cGMP Binding Sites," *Biochemistry*, 28: 6122–6127.

Zagotta, W. N. et al. (1996) "Structure and Function of Cyclic Nucleotide–Gated Channels," *Annu. Rev. Neurosci.*, 19: 235–263.

Zervos, A. S. et al. (1993) "Mxi1, a Protein That Specifically Interacts with Max to Bind Myc–Max Recognition Sites," *Cell*, 72: 223–232.

Ludwig et al, "A family of hyperpolarization–activated mammalian cation channels," *Nature*, 393:587–591 (1998) Macmillan Journals Ltd.

* cited by examiner

FIG. 1A

50
MEGGGKPNSASNSRDDGNSVFPSKAPATGPVAADKRLGTPPRGGAAGKEH

100
GNSVCFKVDGGGGEEPAGSFEDAEGPRRQYGFMQRQFTSMLQPGVNKFSL

S1 150
RMFGSQKAVEKEQERVKTAGFWIIHPYSDERFYWDLIMLIMMVGNLVIIP

S2 200
VGITFFTEQTTTPWIIFNVASDTVFLLDLIMNFRTGTVNEDSSEIILDPK

S3 250
VIKMNYLKSWFVVDFISSIPVDYIFLIVEKGMDSEVYKTARALRIVRFTK

S4 300
ILSLLRLLRLSRLIRYIHQWEEIFHMTYDLASAVVRIFNLIGMMLLLCHW

S5 P 350
DGCLQFLVPLLQDFPPDCWVSLNEMVNDSWGKQYSYALFKAMSHMLCIGY

S6 400
GAQAPVSMSDLWITMLSMIVGATCYAMFVGHATALIQSLDSSRRQYQEKY

450
KQVEQYMSFHKLPADMRQKIHDYYEHRYQGKIFDEENILSELNDPLREEI

500
VNFNCRKLVATMPLFANADPNFVTAMLSKLRFEVFQPGDYIIREGAVGKK

550
MYFIQHGVAGVITKSSKEMKLTDGSYFGEICLLTKGRRTASVRADTYCRL

600
YSLSVDNFNEVLEEYPMMRRAFETVAIDRLDRIGKKNSILLQKFQKDLNT

650
GVFNNQENEILKQIVKHDREMVQAIPPINYPQMTALNCTSSTTTPTSRMR

700
TQSPPVYTATSLSHSNLHSPSPSTQTPQPSAILSPCSYTTAVCSPPIQSP

750
LATRTFHYASPTASQLSLMQQPQQQLPQSQVQQTQTQTQQQQQQQQQQQQ

800
QQQQQQQQQQQQQQQQQQQQQQQQQPQTPGSSTPKNEVHKSTQALHNTNL

850
TKEVRPLSASQPSLPHEVSTLISRPHPTVGESLASIPQPVAAVHSTGLQA

900
GSRSTVPQRVTLFRQMSSGAIPPNRGVPPAPPPPAAVQRESPSVLNTDPD

AEKPRFASNL*

A

B

C

D

F

E

| | mBCNG-2 | mBCNG-3 | hBCNG-1 | hBCNG-2 |
|---|---|---|---|---|
| mBCNG-1 | 84 % | 86 % | 100 % | 84 % |
| mBCNG-2 | | 89 % | 84 % | 98 % |
| mBCNG-3 | | | 86 % | 89 % |
| hBCNG-1 | | | | 84 % |

FIG. 8A

```
                                                                                                     100
mBNCG-1  MEGGGKPNSASNSRDDGNSVFPSKAPATGPVAADKRLGTPPRGGAAGKEHGNSVCFKVDGGGGEEPAGSFEDAEGPRRQYGFMQRQFTSMLQPGVNKFSL
mBCNG-2                                                                                                  ----
mBCNG-3                                                  C-QPSADTAIKVE--AAAIDHILPE--VRLG-S-------GA-----------
mBCNG-4
hBCNG-1
hBCNG-2                                                                      EEAGPAG-PRGS-AS------GAL----------

                                        S1                              S2                            200
mBCNG-1  RMFGSQKAVEKEQERVKTAGFWIIHPYSDFRFYWDLIMLIMMVGNLVIIPVGITFFTEQTTTPWIIFNVASDTVFLLDLIMNFRTGTVNEDSSEIILDPK
mBCNG-2  ----------R------S--A--------------FT--LF-----I---------KDE--A---V---V---F--M--VL-----I-I--NT------E
mBCNG-3  ----------R------S-----------------T--LL-----I---------KDEN-----V---V---F--I--VL-----I-V--NT------Q
mBCNG-4
hBCNG-1            -----------------------------------------------------------------------------------------
hBCNG-2  ----------R------S--A--------------FT--LF-----I---------KDE--A---V---V---F--M--VL-----I-I--NT------E

                S3                              S4                                                    300
mBCNG-1  VIKMNYLKSWFVVDFISSIPVDYIFLIVEKGMDSEVYKTARALRIVRFTKILSLLRLLRLSRLIRYIHQWEEIFHMTYDLASAVVRIFNLIGMMLLLCHW
mBCNG-2  K--KK--RT------V---------------I----------------------------------------------------M--C---S--------
mBCNG-3  R---K----------------E-------TRI----------V--------------------------------------------V------------
mBCNG-4
hBCNG-1  ----------------------------------------------------------------------------------------------------
hBCNG-2  K--KK--RT----V-V---------------I----------------------------------------------------M--C---S--------

  S5                      *              P                           S6                               400
mBCNG-1  DGCLQFLVPLLQDFPPDCWVSLNEMVNDSWGKQYSYALFKAMSHMLCIGYGAQAPVSMSDLWITMLSMIVGATCYAMFVGHATALIQSLDSSRRQYQEKY
mBCNG-2  ---------M-----S-----I-N---H--SEL--F---------------R---E--T-I-L---------------I---------------------
mBCNG-3  ---------M-----H-----I-G---N-----------------------R----G---V-L---------------I---------------------
mBCNG-4
hBCNG-1  ----------------------------------------------------------------------------------------------------
hBCNG-2  ---------M-----RN----I-G---H--SEL--F---------------R---E--T-I-L---------------I---------------------

                                                                                                     500
mBCNG-1  KQVEQYMSFHKLPADMRQKIHDYYEHRYQGKIFDEENILSELNDPLREEIVNFNCRKLVATMPLFANADPNFVTAMLSKLRFEVFQPGDYIIREGAVGKK
mBCNG-2  ---------------F---------------MS--DS--G---G----------------S----------------T--K--------------TI---
mBCNG-3  -------------P-T--R------------M----S--G--SE----------------S-------------S--T-----------------TI---
mBCNG-4
hBCNG-1  ---------------------------------------N------------------------------------------------------------
hBCNG-2  ---------------F---------------M---DS--G---G----------------S----------------T--K--------------TI---
```

FIG. 8B

```
                                            CNBs                                                   ⬇
                                                                                                               600
mBCNG-1   MYFIQHGVAGVITKSSKEMKLTDGSYFGEICLLTKGRRTASVRADTYCRLYSLSVDNFNEVLEEYPMMRRAFETVAIDRLDRIGKKNSILLQKFQKDLNT
mBCNG-2   --------VS-L--GN-----S------------R-----------------------------------------------------T--H-V-H--SS
mBCNG-3   --------VS-L--GN--TR-A------------R-----------------
mBCNG-4                              ------R--------------------H--A----F----------M---R---EACLLC-LWVLAGPHL
hBCNG-1   ----------------------------------------------------------------------------------------------------
hBCNG-2   --------VS-L--GN-----S------------R-------------------------------------------------------H-V-H---S

                                                                                                               700
mBCNG-1   GVFNNQENEILKQIVKHDREMVQAIPPINYPQMTALNCTSSTTTPTSRMRTQSPPVYTATSLSHSNLHSPSPSTQTPQPSAILSPCSYTTAVCSPPIQSP
mBCNG-2
mBCNG-3
mBCNG-4   MSLALVL*
hBCNG-1   -------------------------A--------T--S----------------------------------------------------------V---
hBCNG-2   --------A-IQE---Y------QAELGQRVGFFPPPPPPPQV-SAIATLQ-AAAMSFCPQVA

                                                                                                               800
mBCNG-1   LATRTFHYASPTASQLSLMQQPQQQLPQSQVQQTQTQTQQQQQQQQQQQQQQQQQQQQQQQQQQQQQQQQQQQQQPQTPGSSTPKNEVHKSTQALHNTNL
mBCNG-2
mBCNG-3
mBCNG-4
hBCNG-1   --A------------------QP--QV-QSQPPQTQPQQPSPQ..............................-------------------------
hBCNG-2

                                                                                                               900
mBCNG-1   TKEVRPLSASQPSLPHEVSTLISRPHPTVGESLASIPQPVAAVHSTGLQAGSRSTVPQRVTLFRQMSSGAIPPNRGVPPAPPPPAAVQRESPSVLNTDPD
mBCNG-2
mBCNG-3
mBCNG-4
hBCNG-1   -R----F--W-----------------------------T--PG------G---------F---------------L---L-LITPHPKK
hBCNG-2

mBCNG-1   AEKPRFASNL*
```

He Br Sp Lu Li Mu Ki Te 9.5 —
7.5 —
4.4 —
2.4 —
1.35 — mBCNG-1

He Br Sp Lu Li Mu Ki Te 9.5 —
7.5 —
4.4 —
2.4 —
1.35 — mBCNG-2

He Br Sp Lu Li Mu Ki Te 9.5 —
7.5 —
4.4 —
2.4 —
1.35 — mBCNG-3

He Br Sp Lu Li Mu Ki Te 9.5 —
7.5 —
4.4 —
2.4 —
1.35 — mBCNG-4 hBCNG-1 hBCNG-2 hBCNG-1 hBCNG-2

He Br Pl Lu Li Mu Ki Pa 9.5 —
7.5 —
4.4 —
2.4 —
1.35 — hBCNG-1

He Br Pl Lu Li Mu Ki Pa 9.5 —
7.5 —
4.4 —
2.4 —
1.35 — hBCNG-2

Am Cn CC Hi Br SN Sn Th 9.5 —
7.5 —
4.4 —
2.4 —
1.35 — hBCNG-1

Am Cn CC Hi Br SN Sn Th 9.5 —
7.5 —
4.4 —
2.4 —
1.35 — hBCNG-2

SEQUENCE LISTING

<160> NUMBER OF SEQ ID NOS: 67

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 1
agaggcatag tagccaccag tttcc 25

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 2
ccgctcgagg ccttggtatc ggtgctcata g 31

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 3
gaagcggatg ttaacgatac cagcc 25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 4
gacaagccga caaccttgat tggag 25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 5
gagcaagttc agcctggtta agtcc 25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 6

-continued

```
gtggcttatg agtatttctt ccaggg                                      26


<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 7

tgggaagaga tattccacat gacc                                        24


<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 8

tacgacctgg caagtgcagt gatgcgc                                     27


<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 9

agttcacaat ctcctcacgc agtggccc                                    28


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 10

ctggtggata tatcggatga gccg                                        24


<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 11

cagtgggaag agattttcca catgacc                                     27


<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 12
```

-continued

```
gatcatgctg aaccttgtgc agcaag                                          26


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 13

cacckcrttg aagtggtcca cgct                                            24


<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 14

atgttcggsa gccagaaggc ggtggag                                         27


<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 15

cagctcgaac actggcagta cgac                                            24


<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 16

aacttcaact gccggaagct ggtg                                            24


<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 17

gaaaaagccc acgcgctgac ccag                                            24


<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide PCR Primer

<400> SEQUENCE: 18

caccagcttc cggcagttga agttg                                           25
```

-continued

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 19
gcgaattcaa acccaactcc gcgtccaa 28

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 20
cctgaattca ctgtacggat ggat 24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 21
gtcgtactgc cagtgttcga gctg 24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 22
ggtcaggttg gtgttgtgaa acgc 24

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 23
cagtgggaag agattttcca catgacc 27

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Oligonucleotide PCR Primer

<400> SEQUENCE: 24
gatcatgctg aaccttgtgc agcaag 26

-continued

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
Oligonucleotide PCR Primer

<400> SEQUENCE: 25
cacckcrttg aagtggtcca cgct 24

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence:
Oligonucleotide PCR Primer

<400> SEQUENCE: 26
atgttcggsa gccagaaggc ggtggag 27

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
Oligonucleotide PCR Primer

<400> SEQUENCE: 27
cagctcgaac actggcagta cgac 24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:
Oligonucleotide PCR Primer

<400> SEQUENCE: 28
gagcaggagc gcgtcaagtc ggcg 24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
Oligonucleotide PCR Primer

<400> SEQUENCE: 29
gaagatgtag tccacgggga tgga 24

<210> SEQ ID NO 30
<211> LENGTH: 2732
<212> TYPE: PRT
<213> ORGANISM: Murine

<400> SEQUENCE: 30

Ala Thr Gly Gly Ala Ala Gly Gly Cys Gly Gly Cys Gly Gly Cys Ala
1 5 10 15

Ala Ala Cys Cys Cys Ala Ala Cys Thr Cys Cys Gly Cys Gly Thr Cys
20 25 30

-continued

```
Cys Ala Ala Cys Ala Gly Cys Cys Gly Cys Gly Ala Cys Gly Ala Thr
        35                  40                  45

Gly Gly Cys Ala Ala Cys Ala Gly Cys Gly Thr Cys Thr Thr Cys Cys
    50                  55                  60

Cys Cys Thr Cys Cys Ala Ala Gly Gly Cys Gly Cys Cys Cys Gly Cys
65                  70                  75                  80

Gly Ala Cys Gly Gly Gly Gly Cys Cys Gly Gly Thr Gly Gly Cys Gly
                85                  90                  95

Gly Cys Cys Gly Ala Cys Ala Ala Gly Cys Gly Cys Cys Thr Gly Gly
            100                 105                 110

Gly Gly Ala Cys Cys Cys Cys Gly Cys Cys Gly Ala Gly Gly Gly Gly
        115                 120                 125

Cys Gly Gly Cys Gly Cys Gly Gly Cys Cys Gly Gly Gly Ala Ala Gly
    130                 135                 140

Gly Ala Ala Cys Ala Thr Gly Gly Cys Ala Ala Cys Thr Cys Cys Gly
145                 150                 155                 160

Thr Gly Thr Gly Cys Thr Thr Cys Ala Ala Gly Gly Thr Gly Gly Ala
                165                 170                 175

Cys Gly Gly Cys Gly Gly Cys Gly Gly Ala Gly Gly Ala Gly Ala Gly
            180                 185                 190

Gly Ala Gly Cys Cys Gly Gly Cys Gly Gly Gly Cys Ala Gly Cys Thr
        195                 200                 205

Thr Cys Gly Ala Gly Gly Ala Thr Gly Cys Cys Gly Ala Gly Gly Gly
    210                 215                 220

Gly Cys Cys Cys Cys Gly Gly Cys Gly Gly Cys Ala Gly Thr Ala Thr
225                 230                 235                 240

Gly Gly Thr Thr Thr Cys Ala Thr Gly Cys Ala Gly Ala Gly Gly Cys
                245                 250                 255

Ala Gly Thr Thr Cys Ala Cys Cys Thr Cys Cys Ala Thr Gly Cys Thr
            260                 265                 270

Gly Cys Ala Gly Cys Cys Thr Gly Gly Gly Gly Thr Cys Ala Ala Cys
        275                 280                 285

Ala Ala Ala Thr Thr Cys Thr Cys Cys Cys Thr Cys Cys Gly Cys Ala
    290                 295                 300

Thr Gly Thr Thr Thr Gly Gly Gly Ala Gly Cys Cys Ala Gly Ala Ala
305                 310                 315                 320

Gly Gly Cys Gly Gly Thr Gly Gly Ala Gly Ala Ala Gly Gly Ala Gly
                325                 330                 335

Cys Ala Gly Gly Ala Ala Ala Gly Gly Gly Thr Thr Ala Ala Ala Ala
            340                 345                 350

Cys Thr Gly Cys Ala Gly Gly Cys Thr Thr Cys Thr Gly Gly Ala Thr
        355                 360                 365

Thr Ala Thr Cys Cys Ala Thr Cys Cys Gly Thr Ala Cys Ala Gly Thr
    370                 375                 380

Gly Ala Cys Thr Thr Cys Ala Gly Gly Thr Thr Thr Thr Ala Thr Thr
385                 390                 395                 400

Gly Gly Gly Ala Thr Thr Thr Ala Ala Thr Cys Ala Thr Gly Cys Thr
                405                 410                 415

Thr Ala Thr Ala Ala Thr Gly Ala Thr Gly Gly Thr Thr Gly Gly Ala
            420                 425                 430

Ala Ala Thr Thr Thr Gly Gly Thr Cys Ala Thr Cys Ala Thr Ala Cys
        435                 440                 445

Cys Ala Gly Thr Thr Gly Gly Ala Ala Thr Cys Ala Cys Gly Thr Thr
```

-continued

```
    450                 455                 460

Cys Thr Thr Cys Ala Cys Ala Gly Ala Gly Cys Ala Gly Ala Cys Gly
465                 470                 475                 480

Ala Cys Ala Ala Cys Ala Cys Cys Gly Thr Gly Gly Ala Thr Thr Ala
                485                 490                 495

Thr Thr Thr Thr Cys Ala Ala Cys Gly Thr Gly Gly Cys Ala Thr Cys
            500                 505                 510

Cys Gly Ala Thr Ala Cys Thr Gly Thr Thr Thr Thr Cys Cys Thr Gly
        515                 520                 525

Thr Thr Gly Gly Ala Cys Thr Thr Ala Ala Thr Cys Ala Thr Gly Ala
    530                 535                 540

Ala Thr Thr Thr Thr Ala Gly Gly Ala Cys Thr Gly Gly Gly Ala Cys
545                 550                 555                 560

Thr Gly Thr Cys Ala Ala Thr Gly Ala Ala Gly Ala Cys Ala Gly Cys
                565                 570                 575

Thr Cys Gly Gly Ala Ala Ala Thr Cys Ala Thr Cys Cys Thr Gly Gly
            580                 585                 590

Ala Cys Cys Cys Thr Ala Ala Ala Gly Thr Gly Ala Thr Cys Ala Ala
        595                 600                 605

Gly Ala Thr Gly Ala Ala Thr Thr Ala Thr Thr Thr Ala Ala Ala Ala
    610                 615                 620

Ala Gly Cys Thr Gly Gly Thr Thr Thr Gly Thr Gly Gly Thr Gly Gly
625                 630                 635                 640

Ala Cys Thr Thr Cys Ala Thr Cys Thr Cys Ala Thr Cys Gly Ala Thr
                645                 650                 655

Cys Cys Cys Gly Gly Thr Gly Gly Ala Thr Thr Ala Thr Ala Thr Cys
            660                 665                 670

Thr Thr Thr Cys Thr Cys Ala Thr Thr Gly Thr Ala Gly Ala Gly Ala
        675                 680                 685

Ala Ala Gly Gly Gly Ala Thr Gly Gly Ala Cys Thr Cys Ala Gly Ala
    690                 695                 700

Ala Gly Thr Thr Thr Ala Cys Ala Ala Gly Ala Cys Ala Gly Cys Cys
705                 710                 715                 720

Ala Gly Ala Gly Cys Ala Cys Thr Thr Cys Gly Thr Ala Thr Cys Gly
                725                 730                 735

Thr Gly Ala Gly Gly Thr Thr Thr Ala Cys Ala Ala Ala Ala Ala Thr
            740                 745                 750

Thr Cys Thr Cys Ala Gly Thr Cys Thr Cys Thr Thr Gly Cys Gly Gly
        755                 760                 765

Thr Thr Ala Thr Thr Ala Cys Gly Cys Cys Thr Thr Thr Cys Ala Ala
    770                 775                 780

Gly Gly Thr Thr Ala Ala Thr Cys Ala Gly Ala Thr Ala Cys Ala Thr
785                 790                 795                 800

Ala Cys Ala Cys Cys Ala Gly Thr Gly Gly Gly Ala Ala Gly Ala Gly
                805                 810                 815

Ala Thr Ala Thr Thr Cys Cys Ala Cys Ala Thr Gly Ala Cys Cys Thr
            820                 825                 830

Ala Thr Gly Ala Cys Cys Thr Cys Gly Cys Cys Ala Gly Thr Gly Cys
        835                 840                 845

Thr Gly Thr Gly Gly Thr Gly Ala Gly Gly Ala Thr Cys Thr Thr Cys
    850                 855                 860

Ala Ala Cys Cys Thr Cys Ala Thr Thr Gly Gly Cys Ala Thr Gly Ala
865                 870                 875                 880
```

-continued

```
Thr Gly Cys Thr Gly Cys Thr Thr Cys Thr Gly Thr Gly Cys Cys Ala
                885                 890                 895

Cys Thr Gly Gly Gly Ala Thr Gly Gly Cys Thr Gly Thr Cys Thr Thr
            900                 905                 910

Cys Ala Gly Thr Thr Cys Cys Thr Gly Gly Thr Thr Cys Cys Cys Cys
        915                 920                 925

Thr Gly Cys Thr Gly Cys Ala Gly Gly Ala Cys Thr Thr Cys Cys Cys
    930                 935                 940

Ala Cys Cys Ala Gly Ala Thr Thr Gly Cys Thr Gly Gly Gly Thr Thr
945                 950                 955                 960

Thr Cys Thr Cys Thr Gly Ala Ala Thr Gly Ala Ala Ala Thr Gly Gly
                965                 970                 975

Thr Thr Ala Ala Thr Gly Ala Thr Thr Cys Cys Thr Gly Gly Gly Gly
            980                 985                 990

Ala Ala Ala Ala Cys Ala Ala Thr Ala Thr Thr Cys Cys Thr Ala Cys
        995                 1000                1005

Gly Cys Ala Cys Thr Cys Thr Thr Cys Ala Ala Ala Gly Cys Thr Ala
    1010                1015                1020

Thr Gly Ala Gly Thr Cys Ala Cys Ala Thr Gly Cys Thr Gly Thr Gly
1025                1030                1035                1040

Cys Ala Thr Thr Gly Gly Thr Thr Ala Thr Gly Gly Cys Gly Cys Cys
                1045                1050                1055

Cys Ala Ala Gly Cys Cys Cys Cys Thr Gly Thr Cys Ala Gly Cys Ala
            1060                1065                1070

Thr Gly Thr Cys Thr Gly Ala Cys Cys Thr Cys Thr Gly Gly Ala Thr
        1075                1080                1085

Thr Ala Cys Cys Ala Thr Gly Cys Thr Gly Ala Gly Cys Ala Thr Gly
    1090                1095                1100

Ala Thr Thr Gly Thr Gly Gly Gly Cys Gly Cys Cys Ala Cys Cys Thr
1105                1110                1115                1120

Gly Cys Thr Ala Cys Gly Cys Ala Ala Thr Gly Thr Thr Thr Gly Thr
                1125                1130                1135

Thr Gly Gly Cys Cys Ala Thr Gly Cys Cys Ala Cys Ala Gly Cys Thr
            1140                1145                1150

Thr Thr Gly Ala Thr Cys Cys Ala Gly Thr Cys Thr Thr Thr Gly Gly
        1155                1160                1165

Ala Cys Thr Cys Thr Thr Cys Ala Ala Gly Gly Ala Gly Gly Cys Ala
    1170                1175                1180

Gly Thr Ala Thr Cys Ala Ala Gly Ala Gly Ala Ala Gly Thr Ala Thr
1185                1190                1195                1200

Ala Ala Gly Cys Ala Ala Gly Thr Ala Gly Ala Gly Cys Ala Ala Thr
                1205                1210                1215

Ala Cys Ala Thr Gly Thr Cys Ala Thr Thr Cys Cys Ala Cys Ala Ala
            1220                1225                1230

Gly Thr Thr Ala Cys Cys Ala Gly Cys Thr Gly Ala Cys Ala Thr Gly
        1235                1240                1245

Cys Gly Cys Cys Ala Gly Ala Ala Gly Ala Thr Ala Cys Ala Thr Gly
    1250                1255                1260

Ala Thr Thr Ala Cys Thr Ala Thr Gly Ala Gly Cys Ala Cys Cys Gly
1265                1270                1275                1280

Ala Thr Ala Cys Cys Ala Ala Gly Gly Cys Ala Ala Gly Ala Thr Cys
                1285                1290                1295
```

-continued

```
Thr Thr Cys Gly Ala Thr Gly Ala Ala Gly Ala Ala Ala Ala Thr Ala
            1300                1305                1310

Thr Thr Cys Thr Cys Ala Gly Thr Gly Ala Gly Cys Thr Thr Ala Ala
        1315                1320                1325

Thr Gly Ala Thr Cys Cys Thr Cys Thr Gly Ala Gly Ala Gly Ala Gly
    1330                1335                1340

Gly Ala Ala Ala Thr Ala Gly Thr Cys Ala Ala Cys Thr Thr Cys Ala
1345                1350                1355                1360

Ala Cys Thr Gly Cys Cys Gly Gly Ala Ala Ala Cys Thr Gly Gly Thr
                1365                1370                1375

Gly Gly Cys Thr Ala Cys Thr Ala Thr Gly Cys Cys Thr Cys Thr Thr
            1380                1385                1390

Thr Thr Thr Gly Cys Thr Ala Ala Cys Gly Cys Cys Gly Ala Thr Cys
        1395                1400                1405

Cys Cys Ala Ala Thr Thr Thr Cys Gly Thr Gly Ala Cys Gly Gly Cys
    1410                1415                1420

Cys Ala Thr Gly Cys Thr Gly Ala Gly Cys Ala Ala Gly Cys Thr Gly
1425                1430                1435                1440

Ala Gly Ala Thr Thr Thr Gly Ala Gly Gly Thr Gly Thr Thr Cys Cys
                1445                1450                1455

Ala Gly Cys Cys Cys Gly Gly Ala Gly Ala Cys Thr Ala Thr Ala Thr
            1460                1465                1470

Cys Ala Thr Thr Cys Gly Ala Gly Ala Ala Gly Gly Ala Gly Cys Thr
        1475                1480                1485

Gly Thr Gly Gly Gly Gly Ala Ala Gly Ala Ala Ala Ala Thr Gly Thr
    1490                1495                1500

Ala Thr Thr Thr Cys Ala Thr Cys Cys Ala Gly Cys Ala Cys Gly Gly
1505                1510                1515                1520

Thr Gly Thr Thr Gly Cys Thr Gly Gly Cys Gly Thr Thr Ala Thr Cys
                1525                1530                1535

Ala Cys Cys Ala Ala Gly Thr Cys Cys Ala Gly Thr Ala Ala Ala Gly
            1540                1545                1550

Ala Ala Ala Thr Gly Ala Ala Gly Cys Thr Gly Ala Cys Ala Gly Ala
        1555                1560                1565

Thr Gly Gly Cys Thr Cys Thr Thr Ala Cys Thr Thr Cys Gly Gly Ala
    1570                1575                1580

Gly Ala Gly Ala Thr Ala Thr Gly Cys Cys Thr Gly Cys Thr Gly Ala
1585                1590                1595                1600

Cys Cys Ala Ala Gly Gly Gly Cys Cys Gly Gly Cys Gly Cys Ala Cys
                1605                1610                1615

Thr Gly Cys Cys Ala Gly Thr Gly Thr Cys Cys Gly Ala Gly Cys Thr
            1620                1625                1630

Gly Ala Thr Ala Cys Cys Thr Ala Cys Thr Gly Thr Cys Gly Thr Cys
        1635                1640                1645

Thr Thr Thr Ala Cys Thr Cys Cys Cys Thr Thr Thr Cys Gly Gly Thr
    1650                1655                1660

Gly Gly Ala Cys Ala Ala Thr Thr Thr Cys Ala Ala Thr Gly Ala Gly
1665                1670                1675                1680

Gly Thr Cys Thr Thr Gly Gly Ala Gly Gly Ala Ala Thr Ala Thr Cys
                1685                1690                1695

Cys Ala Ala Thr Gly Ala Thr Gly Ala Gly Ala Ala Gly Ala Gly Cys
            1700                1705                1710

Cys Thr Thr Thr Gly Ala Gly Ala Cys Ala Gly Thr Thr Gly Cys Thr
```

-continued

```
        1715                1720                1725

Ala Thr Thr Gly Ala Cys Cys Gly Ala Cys Thr Cys Gly Ala Thr Cys
    1730                1735                1740

Gly Gly Ala Thr Ala Gly Gly Cys Ala Ala Gly Ala Ala Ala Ala Ala
1745                1750                1755                1760

Cys Thr Cys Thr Ala Thr Thr Cys Thr Cys Cys Thr Gly Cys Ala Gly
                1765                1770                1775

Ala Ala Gly Thr Thr Cys Cys Ala Gly Ala Ala Gly Gly Ala Thr Cys
            1780                1785                1790

Thr Ala Ala Ala Cys Ala Cys Thr Gly Gly Thr Gly Thr Thr Thr Thr
        1795                1800                1805

Cys Ala Ala Cys Ala Ala Cys Cys Ala Gly Gly Ala Gly Ala Ala Cys
    1810                1815                1820

Gly Ala Gly Ala Thr Cys Cys Thr Gly Ala Ala Gly Cys Ala Gly Ala
1825                1830                1835                1840

Thr Cys Gly Thr Gly Ala Ala Gly Cys Ala Thr Gly Ala Cys Cys Gly
                1845                1850                1855

Ala Gly Ala Gly Ala Thr Gly Gly Thr Ala Cys Ala Ala Gly Cys Thr
            1860                1865                1870

Ala Thr Cys Cys Cys Thr Cys Cys Ala Ala Thr Cys Ala Ala Cys Thr
        1875                1880                1885

Ala Thr Cys Cys Thr Cys Ala Ala Ala Thr Gly Ala Cys Ala Gly Cys
    1890                1895                1900

Cys Cys Thr Cys Ala Ala Cys Thr Gly Cys Ala Cys Ala Thr Cys Thr
1905                1910                1915                1920

Thr Cys Ala Ala Cys Cys Ala Cys Cys Ala Cys Cys Cys Cys Ala Ala
                1925                1930                1935

Cys Cys Thr Cys Cys Gly Cys Ala Thr Gly Ala Gly Gly Ala Cys
            1940                1945                1950

Cys Cys Ala Ala Thr Cys Thr Cys Cys Gly Cys Cys Ala Gly Thr Cys
        1955                1960                1965

Thr Ala Cys Ala Cys Cys Gly Cys Ala Ala Cys Cys Ala Gly Cys Cys
    1970                1975                1980

Thr Gly Thr Cys Thr Cys Ala Cys Ala Gly Cys Ala Ala Thr Cys Thr
1985                1990                1995                2000

Gly Cys Ala Cys Thr Cys Ala Cys Cys Cys Ala Gly Thr Cys Cys Cys
                2005                2010                2015

Ala Gly Cys Ala Cys Ala Cys Ala Gly Ala Cys Gly Cys Cys Cys Cys
            2020                2025                2030

Ala Ala Cys Cys Cys Thr Cys Ala Gly Cys Cys Ala Thr Cys Cys Thr
        2035                2040                2045

Thr Cys Ala Cys Cys Cys Thr Gly Cys Thr Cys Cys Thr Ala Thr Ala
    2050                2055                2060

Cys Cys Ala Cys Ala Gly Cys Ala Gly Thr Cys Thr Gly Cys Ala Gly
2065                2070                2075                2080

Thr Cys Cys Thr Cys Cys Thr Ala Thr Ala Cys Ala Gly Ala Gly Cys
                2085                2090                2095

Cys Cys Cys Cys Thr Gly Gly Cys Cys Ala Cys Ala Cys Gly Ala Ala
            2100                2105                2110

Cys Thr Thr Thr Cys Cys Ala Thr Thr Ala Thr Gly Cys Cys Thr Cys
        2115                2120                2125

Thr Cys Cys Cys Ala Cys Thr Gly Cys Gly Thr Cys Cys Cys Ala Gly
    2130                2135                2140
```

-continued

```
Cys Thr Gly Thr Cys Ala Cys Thr Cys Ala Thr Gly Cys Ala Gly Cys
2145                2150                2155                2160

Ala Gly Cys Cys Thr Cys Ala Gly Cys Ala Gly Cys Ala Ala Cys Thr
                2165                2170                2175

Ala Cys Cys Gly Cys Ala Gly Thr Cys Cys Cys Ala Gly Gly Thr Ala
            2180                2185                2190

Cys Ala Gly Cys Ala Gly Ala Cys Thr Cys Ala Gly Ala Cys Thr Cys
        2195                2200                2205

Ala Gly Ala Cys Thr Cys Ala Gly Cys Ala Gly Cys Ala Gly Cys Ala
    2210                2215                2220

Gly Cys Ala Gly Cys Ala Ala Cys Ala Gly Cys Ala Gly Cys Ala Gly
2225                2230                2235                2240

Cys Ala Gly Cys Ala Gly Cys Ala Gly Cys Ala Gly Cys Ala Ala Cys
                2245                2250                2255

Ala Gly Cys Ala Ala Cys Ala Ala Cys Ala Gly Cys Ala Gly Cys Ala
            2260                2265                2270

Gly Cys Ala Gly Cys Ala Gly Cys Ala Gly Cys Ala Gly Cys Ala Gly
        2275                2280                2285

Cys Ala Gly Cys Ala Gly Cys Ala Gly Cys Ala Gly Cys Ala Gly Cys
    2290                2295                2300

Ala Gly Cys Ala Gly Cys Ala Gly Cys Ala Gly Cys Ala Gly Cys Ala
2305                2310                2315                2320

Gly Cys Ala Gly Cys Cys Ala Cys Ala Gly Ala Cys Ala Cys Cys Thr
                2325                2330                2335

Gly Gly Thr Ala Gly Cys Thr Cys Cys Ala Cys Ala Cys Cys Gly Ala
            2340                2345                2350

Ala Ala Ala Ala Thr Gly Ala Ala Gly Thr Gly Cys Ala Cys Ala Ala
        2355                2360                2365

Gly Ala Gly Cys Ala Cys Ala Cys Ala Ala Gly Cys Cys Cys Thr Thr
    2370                2375                2380

Cys Ala Thr Ala Ala Cys Ala Cys Cys Ala Ala Cys Cys Thr Gly Ala
2385                2390                2395                2400

Cys Cys Ala Ala Ala Gly Ala Ala Gly Thr Cys Ala Gly Gly Cys Cys
                2405                2410                2415

Cys Cys Thr Thr Thr Cys Cys Gly Cys Cys Thr Cys Gly Cys Ala Gly
            2420                2425                2430

Cys Cys Thr Thr Cys Thr Cys Thr Gly Cys Cys Cys Cys Ala Thr Gly
        2435                2440                2445

Ala Gly Gly Thr Cys Thr Cys Cys Ala Cys Thr Thr Thr Gly Ala Thr
    2450                2455                2460

Cys Thr Cys Cys Ala Gly Ala Cys Cys Thr Cys Ala Thr Cys Cys Cys
2465                2470                2475                2480

Ala Cys Thr Gly Thr Gly Gly Gly Cys Gly Ala Ala Thr Cys Cys Cys
                2485                2490                2495

Thr Gly Gly Cys Cys Thr Cys Thr Ala Thr Cys Cys Cys Thr Cys Ala
            2500                2505                2510

Ala Cys Cys Cys Gly Thr Gly Gly Cys Ala Gly Cys Ala Gly Thr Cys
        2515                2520                2525

Cys Ala Cys Ala Gly Cys Ala Cys Thr Gly Gly Cys Cys Thr Thr Cys
    2530                2535                2540

Ala Gly Gly Cys Ala Gly Gly Gly Ala Gly Cys Ala Gly Gly Ala Gly
2545                2550                2555                2560
```

-continued

Cys Ala Cys Ala Gly Thr Gly Cys Cys Ala Cys Ala Ala Cys Gly Thr
2565 2570 2575

Gly Thr Cys Ala Cys Cys Thr Thr Gly Thr Thr Cys Cys Gly Ala Cys
2580 2585 2590

Ala Gly Ala Thr Gly Thr Cys Cys Thr Cys Gly Gly Gly Ala Gly Cys
2595 2600 2605

Cys Ala Thr Cys Cys Cys Cys Cys Cys Cys Ala Ala Cys Cys Gly Ala
2610 2615 2620

Gly Gly Ala Gly Thr Gly Cys Cys Thr Cys Cys Ala Gly Cys Ala Cys
2625 2630 2635 2640

Cys Cys Cys Cys Thr Cys Cys Ala Cys Cys Ala Gly Cys Ala Gly Cys
2645 2650 2655

Thr Gly Thr Gly Cys Ala Gly Ala Gly Ala Gly Ala Gly Thr Cys Thr
2660 2665 2670

Cys Cys Cys Thr Cys Ala Gly Thr Cys Cys Thr Ala Ala Ala Thr Ala
2675 2680 2685

Cys Ala Gly Ala Cys Cys Cys Ala Gly Ala Thr Gly Cys Ala Gly Ala
2690 2695 2700

Ala Ala Ala Ala Cys Cys Cys Cys Gly Thr Thr Thr Thr Gly Cys Thr
2705 2710 2715 2720

Thr Cys Gly Ala Ala Thr Thr Thr Ala Thr Gly Ala
2725 2730

<210> SEQ ID NO 31
<211> LENGTH: 910
<212> TYPE: PRT
<213> ORGANISM: Murine

<400> SEQUENCE: 31

Met Glu Gly Gly Gly Lys Pro Asn Ser Ala Ser Asn Ser Arg Asp Asp
1 5 10 15

Gly Asn Ser Val Phe Pro Ser Lys Ala Pro Ala Thr Gly Pro Val Ala
20 25 30

Ala Asp Lys Arg Leu Gly Thr Pro Pro Arg Gly Gly Ala Ala Gly Lys
35 40 45

Glu His Gly Asn Ser Val Cys Phe Lys Val Asp Gly Gly Gly Gly Glu
50 55 60

Glu Pro Ala Gly Ser Phe Glu Asp Ala Glu Gly Pro Arg Arg Gln Tyr
65 70 75 80

Gly Phe Met Gln Arg Gln Phe Thr Ser Met Leu Gln Pro Gly Val Asn
85 90 95

Lys Phe Ser Leu Arg Met Phe Gly Ser Gln Lys Ala Val Glu Lys Glu
100 105 110

Gln Glu Arg Val Lys Thr Ala Gly Phe Trp Ile Ile His Pro Tyr Ser
115 120 125

Asp Phe Arg Phe Tyr Trp Asp Leu Ile Met Leu Ile Met Met Val Gly
130 135 140

Asn Leu Val Ile Ile Pro Val Gly Ile Thr Phe Phe Thr Glu Gln Thr
145 150 155 160

Thr Thr Pro Trp Ile Ile Phe Asn Val Ala Ser Asp Thr Val Phe Leu
165 170 175

Leu Asp Leu Ile Met Asn Phe Arg Thr Gly Thr Val Asn Glu Asp Ser
180 185 190

Ser Glu Ile Ile Leu Asp Pro Lys Val Ile Lys Met Asn Tyr Leu Lys
195 200 205

-continued

```
Ser Trp Phe Val Val Asp Phe Ile Ser Ser Ile Pro Val Asp Tyr Ile
    210                 215                 220

Phe Leu Ile Val Glu Lys Gly Met Asp Ser Glu Val Tyr Lys Thr Ala
225                 230                 235                 240

Arg Ala Leu Arg Ile Val Arg Phe Thr Lys Ile Leu Ser Leu Leu Arg
                245                 250                 255

Leu Leu Arg Leu Ser Arg Leu Ile Arg Tyr Ile His Gln Trp Glu Glu
            260                 265                 270

Ile Phe His Met Thr Tyr Asp Leu Ala Ser Ala Val Val Arg Ile Phe
        275                 280                 285

Asn Leu Ile Gly Met Met Leu Leu Leu Cys His Trp Asp Gly Cys Leu
    290                 295                 300

Gln Phe Leu Val Pro Leu Leu Gln Asp Phe Pro Pro Asp Cys Trp Val
305                 310                 315                 320

Ser Leu Asn Glu Met Val Asn Asp Ser Trp Gly Lys Gln Tyr Ser Tyr
                325                 330                 335

Ala Leu Phe Lys Ala Met Ser His Met Leu Cys Ile Gly Tyr Gly Ala
            340                 345                 350

Gln Ala Pro Val Ser Met Ser Asp Leu Trp Ile Thr Met Leu Ser Met
        355                 360                 365

Ile Val Gly Ala Thr Cys Tyr Ala Met Phe Val Gly His Ala Thr Ala
    370                 375                 380

Leu Ile Gln Ser Leu Asp Ser Ser Arg Arg Gln Tyr Gln Glu Lys Tyr
385                 390                 395                 400

Lys Gln Val Glu Gln Tyr Met Ser Phe His Lys Leu Pro Ala Asp Met
                405                 410                 415

Arg Gln Lys Ile His Asp Tyr Tyr Glu His Arg Tyr Gln Gly Lys Ile
            420                 425                 430

Phe Asp Glu Glu Asn Ile Leu Ser Glu Leu Asn Asp Pro Leu Arg Glu
        435                 440                 445

Glu Ile Val Asn Phe Asn Cys Arg Lys Leu Val Ala Thr Met Pro Leu
    450                 455                 460

Phe Ala Asn Ala Asp Pro Asn Phe Val Thr Ala Met Leu Ser Lys Leu
465                 470                 475                 480

Arg Phe Glu Val Phe Gln Pro Gly Asp Tyr Ile Ile Arg Glu Gly Ala
                485                 490                 495

Val Gly Lys Lys Met Tyr Phe Ile Gln His Gly Val Ala Gly Val Ile
            500                 505                 510

Thr Lys Ser Ser Lys Glu Met Lys Leu Thr Asp Gly Ser Tyr Phe Gly
        515                 520                 525

Glu Ile Cys Leu Leu Thr Lys Gly Arg Arg Thr Ala Ser Val Arg Ala
    530                 535                 540

Asp Thr Tyr Cys Arg Leu Tyr Ser Leu Ser Val Asp Asn Phe Asn Glu
545                 550                 555                 560

Val Leu Glu Glu Tyr Pro Met Met Arg Arg Ala Phe Glu Thr Val Ala
                565                 570                 575

Ile Asp Arg Leu Asp Arg Ile Gly Lys Lys Asn Ser Ile Leu Leu Gln
            580                 585                 590

Lys Phe Gln Lys Asp Leu Asn Thr Gly Val Phe Asn Asn Gln Glu Asn
        595                 600                 605

Glu Ile Leu Lys Gln Ile Val Lys His Asp Arg Glu Met Val Gln Ala
    610                 615                 620
```

-continued

```
Ile Pro Pro Ile Asn Tyr Pro Gln Met Thr Ala Leu Asn Cys Thr Ser
625                 630                 635                 640

Ser Thr Thr Thr Pro Thr Ser Arg Met Arg Thr Gln Ser Pro Pro Val
                645                 650                 655

Tyr Thr Ala Thr Ser Leu Ser His Ser Asn Leu His Ser Pro Ser Pro
            660                 665                 670

Ser Thr Gln Thr Pro Gln Pro Ser Ala Ile Leu Ser Pro Cys Ser Tyr
        675                 680                 685

Thr Thr Ala Val Cys Ser Pro Pro Ile Gln Ser Pro Leu Ala Thr Arg
    690                 695                 700

Thr Phe His Tyr Ala Ser Pro Thr Ala Ser Gln Leu Ser Leu Met Gln
705                 710                 715                 720

Gln Pro Gln Gln Gln Leu Pro Gln Ser Gln Val Gln Gln Thr Gln Thr
                725                 730                 735

Gln Thr Gln Gln Gln Gln Gln Gln Gln Gln Gln Gln Gln Gln Gln Gln
            740                 745                 750

Gln Gln Gln Gln Gln Gln Gln Gln Gln Gln Gln Gln Gln Gln Gln Gln
        755                 760                 765

Gln Gln Gln Gln Gln Gln Gln Pro Gln Thr Pro Gly Ser Ser Thr Pro
    770                 775                 780

Lys Asn Glu Val His Lys Ser Thr Gln Ala Leu His Asn Thr Asn Leu
785                 790                 795                 800

Thr Lys Glu Val Arg Pro Leu Ser Ala Ser Gln Pro Ser Leu Pro His
                805                 810                 815

Glu Val Ser Thr Leu Ile Ser Arg Pro His Pro Thr Val Gly Glu Ser
            820                 825                 830

Leu Ala Ser Ile Pro Gln Pro Val Ala Ala Val His Ser Thr Gly Leu
        835                 840                 845

Gln Ala Gly Ser Arg Ser Thr Val Pro Gln Arg Val Thr Leu Phe Arg
    850                 855                 860

Gln Met Ser Ser Gly Ala Ile Pro Pro Asn Arg Gly Val Pro Pro Ala
865                 870                 875                 880

Pro Pro Pro Pro Ala Ala Val Gln Arg Glu Ser Pro Ser Val Leu Asn
                885                 890                 895

Thr Asp Pro Asp Ala Glu Lys Pro Arg Phe Ala Ser Asn Leu
            900                 905                 910


<210> SEQ ID NO 32
<211> LENGTH: 1512
<212> TYPE: DNA
<213> ORGANISM: Murine

<400> SEQUENCE: 32

aagttctccc tgcggatgtt cggcagccag aaggccgtgg agcgcgagca ggaacgcgtg      60

aagtcggcgg gggcctggat catccacccc tacagcgact tcaggttcta ctgggacttc     120

accatgctgt tgttcatggt gggaaatctc attatcattc ccgtgggcat cactttcttc     180

aaggacgaga ccaccgcgcc ctggatcgtc ttcaacgtgg tctcggacac tttcttcctc     240

atggacttgg tgttgaactt ccgcaccggc attgttattg aggacaacac ggagatcatc     300

ctggaccccg agaagataaa gaagaagtac ttgcgtacgt ggttcgtggt ggacttcgtg     360

tcatccatcc cggtggacta catcttcctc atagtggaga agggaatcga ctccgaggtc     420

tacaagacag cgcgtgctct gcgcatcgtg cgcttcacca agatcctcag tctgctgcgg     480

ctgctgcggc tatcacggct catccgatat atccaccagt gggaagagat tttccacatg     540
```

-continued

```
acctacgacc tggcaagtgc agtgatgcgc atctgtaacc tgatcagcat gatgctactg    600
ctctgccact gggacggttg cctgcagttc ctggtgccca tgctgcaaga cttccccagc    660
gactgctggg tgtccatcaa caacatggtg aaccactcgt ggagcgagct ctactcgttc    720
gcgctcttca aggccatgag ccacatgctg tgcatcggct acgggcggca ggcgcccgag    780
agcatgacag acatctggct gaccatgctc agcatgatcg taggcgccac ctgctatgcc    840
atgttcattg ggcacgccac tgcgctcatc cagtccctgg attcgtcacg gcgccaatac    900
caggagaagt acaagcaagt agagcaatac atgtccttcc acaaactgcc cgctgacttc    960
cgccagaaga tccacgatta ctatgaacac cggtaccaag ggaagatgtc tgatgaggac   1020
agcatccttg gggaactcaa cgggccactg cgtgaggaga ttgtgaactt caactgccgg   1080
aagctggtgg cttccatgcc gctgtttgcc aatgcagacc ccaatttcgt cacagccatg   1140
ctgacaaagc tcaaatttga ggtcttccag cctggagatt acatcatccg agaggggacc   1200
atcgggaaga agatgtactt catccagcat ggggtggtga gcgtgctcac caagggcaac   1260
aaggagatga agctgtcgga tggctcctat ttcggggaga tctgcttgct cacgaggggc   1320
cggcgtacgg ccagcgtgcg agctgacacc tactgtcgcc tctactcact gagtgtggac   1380
aatttcaacg aggtgctgga ggaatacccc atgatgcggc gtgcctttga gactgtggct   1440
attgaccggc tagatcgcat aggcaagaag aactccacct tgctgcacaa ggttcagcat   1500
gatctcagct cc                                                       1512
```

<210> SEQ ID NO 33
<211> LENGTH: 504
<212> TYPE: PRT
<213> ORGANISM: Murine

<400> SEQUENCE: 33

```
Lys Phe Ser Leu Arg Met Phe Gly Ser Gln Lys Ala Val Glu Arg Glu
  1               5                  10                  15

Gln Glu Arg Val Lys Ser Ala Gly Ala Trp Ile Ile His Pro Tyr Ser
             20                  25                  30

Asp Phe Arg Phe Tyr Trp Asp Phe Thr Met Leu Leu Phe Met Val Gly
         35                  40                  45

Asn Leu Ile Ile Ile Pro Val Gly Ile Thr Phe Phe Lys Asp Glu Thr
     50                  55                  60

Thr Ala Pro Trp Ile Val Phe Asn Val Val Ser Asp Thr Phe Phe Leu
 65                  70                  75                  80

Met Asp Leu Val Leu Asn Phe Arg Thr Gly Ile Val Ile Glu Asp Asn
                 85                  90                  95

Thr Glu Ile Ile Leu Asp Pro Glu Lys Ile Lys Lys Lys Tyr Leu Arg
            100                 105                 110

Thr Trp Phe Val Val Asp Phe Val Ser Ser Ile Pro Val Asp Tyr Ile
        115                 120                 125

Phe Leu Ile Val Glu Lys Gly Ile Asp Ser Glu Val Tyr Lys Thr Ala
    130                 135                 140

Arg Ala Leu Arg Ile Val Arg Phe Thr Lys Ile Leu Ser Leu Leu Arg
145                 150                 155                 160

Leu Leu Arg Leu Ser Arg Leu Ile Arg Tyr Ile His Gln Trp Glu Glu
                165                 170                 175

Ile Phe His Met Thr Tyr Asp Leu Ala Ser Ala Val Met Arg Ile Cys
            180                 185                 190
```

-continued

```
Asn Leu Ile Ser Met Met Leu Leu Leu Cys His Trp Asp Gly Cys Leu
      195                 200                 205

Gln Phe Leu Val Pro Met Leu Gln Asp Phe Pro Ser Asp Cys Trp Val
    210                 215                 220

Ser Ile Asn Asn Met Val Asn His Ser Trp Ser Glu Leu Tyr Ser Phe
225                 230                 235                 240

Ala Leu Phe Lys Ala Met Ser His Met Leu Cys Ile Gly Tyr Gly Arg
                245                 250                 255

Gln Ala Pro Glu Ser Met Thr Asp Ile Trp Leu Thr Met Leu Ser Met
            260                 265                 270

Ile Val Gly Ala Thr Cys Tyr Ala Met Phe Ile Gly His Ala Thr Ala
        275                 280                 285

Leu Ile Gln Ser Leu Asp Ser Ser Arg Arg Gln Tyr Gln Glu Lys Tyr
    290                 295                 300

Lys Gln Val Glu Gln Tyr Met Ser Phe His Lys Leu Pro Ala Asp Phe
305                 310                 315                 320

Arg Gln Lys Ile His Asp Tyr Tyr Glu His Arg Tyr Gln Gly Lys Met
                325                 330                 335

Ser Asp Glu Asp Ser Ile Leu Gly Glu Leu Asn Gly Pro Leu Arg Glu
            340                 345                 350

Glu Ile Val Asn Phe Asn Cys Arg Lys Leu Val Ala Ser Met Pro Leu
        355                 360                 365

Phe Ala Asn Ala Asp Pro Asn Phe Val Thr Ala Met Leu Thr Lys Leu
    370                 375                 380

Lys Phe Glu Val Phe Gln Pro Gly Asp Tyr Ile Ile Arg Glu Gly Thr
385                 390                 395                 400

Ile Gly Lys Lys Met Tyr Phe Ile Gln His Gly Val Val Ser Val Leu
                405                 410                 415

Thr Lys Gly Asn Lys Glu Met Lys Leu Ser Asp Gly Ser Tyr Phe Gly
            420                 425                 430

Glu Ile Cys Leu Leu Thr Arg Gly Arg Arg Thr Ala Ser Val Arg Ala
        435                 440                 445

Asp Thr Tyr Cys Arg Leu Tyr Ser Leu Ser Val Asp Asn Phe Asn Glu
    450                 455                 460

Val Leu Glu Glu Tyr Pro Met Met Arg Arg Ala Phe Glu Thr Val Ala
465                 470                 475                 480

Ile Asp Arg Leu Asp Arg Ile Gly Lys Lys Asn Ser Thr Leu Leu His
                485                 490                 495

Lys Val Gln His Asp Leu Ser Ser
            500
```

```
<210> SEQ ID NO 34
<211> LENGTH: 1518
<212> TYPE: DNA
<213> ORGANISM: Murine

<400> SEQUENCE: 34

tgcgagcagc cctcggcgga caccgctatc aaagtggagg gaggcgcggc cgccatcgac      60

catatcctcc ccgaggccga ggtgcgcctg ggccaaagcg gcttcatgca gcgccagttc     120

ggtgccatgc tgcaacctgg ggtcaacaaa ttctccctaa ggatgttcgg cagccagaaa     180

gcggtggagc gcgagcagga gagggttaag tcagcagggt tttggattat ccacccctac     240

agtgacttca gattttactg ggacctgacg atgctgttgc tgatggtggg gaatctgatc     300

atcatacccg tgggcatcac cttcttcaag gatgagaaca ccacaccctg gatcgtcttc     360
```

-continued

```
aatgtggtgt cagacacatt cttcctcatt gacttggtcc tcaacttccg cacggggatc     420

gtggtggagg acaacacaga aatcatcctt gacccgcaga ggatcaagat gaagtacctg     480

aaaagctggt ttgtggtaga tttcatctcc tccatacctg tcgaatacat tttccttata     540

gtggagactc gcattgactc ggaggtttac aaaaccgcta gggctgtgcg cattgtccgt     600

ttcactaaga tcctcagcct cctgcgcctc ttgaggcttt cccgcctcat tcgatacatt     660

catcagtggg aagagatttt ccacatgacc tatgacctgg ccagcgccgt ggtacgcatc     720

gtgaacctca ttggcatgat gcttctgctg tgtcactggg atggctgcct gcagttccta     780

gtgcccatgc tgcaggactt cccccatgac tgctgggtgt ccatcaatgg catggtgaat     840

aactcctggg ggaagcagta ttcctacgcc ctcttcaagg ccatgagcca catgctgtgc     900

attgggtatg gacggcaggc acccgtaggc atgtctgacg tctggctcac catgctcagc     960

atgatcgtgg gggccacctg ctatgccatg ttcatcggcc acgccactgc cctcatccag    1020

tcgctagact cctcccggcg ccagtaccag gagaagtata aacaggtgga gcagtacatg    1080

tctttccaca agctcccgcc tgacacccga cagcgcatcc atgactacta tgaacaccgt    1140

taccaaggca agatgtttga tgaggaaagc atcctgggtg agttgagtga gccacttcga    1200

gaggagatca tcaactttaa ctgccgaaag ctggtggcat ccatgccact gtttgccaac    1260

gcagatccca actttgtgac atccatgctg accaagttgc gtttcgaggt cttccagcct    1320

ggggattaca tcatccgcga aggcaccatc ggcaagaaga tgtactttat ccagcacggc    1380

gtggtcagcg tgctcactaa gggcaacaaa gagaccaggc tggctgatgg ctcctatttt    1440

ggagagatct gcttgctgac ccggggtcgg cgcacagcca gcgtcagagc ggatacttat    1500

tnccgcctct actcactg                                                  1518
```

<210> SEQ ID NO 35
<211> LENGTH: 506
<212> TYPE: PRT
<213> ORGANISM: Murine

<400> SEQUENCE: 35

```
Cys Glu Gln Pro Ser Ala Asp Thr Ala Ile Lys Val Glu Gly Gly Ala
  1               5                  10                  15

Ala Ala Ile Asp His Ile Leu Pro Glu Ala Glu Val Arg Leu Gly Gln
             20                  25                  30

Ser Gly Phe Met Gln Arg Gln Phe Gly Ala Met Leu Gln Pro Gly Val
         35                  40                  45

Asn Lys Phe Ser Leu Arg Met Phe Gly Ser Gln Lys Ala Val Glu Arg
     50                  55                  60

Glu Gln Glu Arg Val Lys Ser Ala Gly Phe Trp Ile Ile His Pro Tyr
 65                  70                  75                  80

Ser Asp Phe Arg Phe Tyr Trp Asp Leu Thr Met Leu Leu Leu Met Val
                 85                  90                  95

Gly Asn Leu Ile Ile Ile Pro Val Gly Ile Thr Phe Phe Lys Asp Glu
            100                 105                 110

Asn Thr Thr Pro Trp Ile Val Phe Asn Val Val Ser Asp Thr Phe Phe
        115                 120                 125

Leu Ile Asp Leu Val Leu Asn Phe Arg Thr Gly Ile Val Val Glu Asp
    130                 135                 140

Asn Thr Glu Ile Ile Leu Asp Pro Gln Arg Ile Lys Met Lys Tyr Leu
145                 150                 155                 160
```

-continued

```
Lys Ser Trp Phe Val Val Asp Phe Ile Ser Ser Ile Pro Val Glu Tyr
                165                 170                 175

Ile Phe Leu Ile Val Glu Thr Arg Ile Asp Ser Glu Val Tyr Lys Thr
            180                 185                 190

Ala Arg Ala Val Arg Ile Val Arg Phe Thr Lys Ile Leu Ser Leu Leu
        195                 200                 205

Arg Leu Leu Arg Leu Ser Arg Leu Ile Arg Tyr Ile His Gln Trp Glu
    210                 215                 220

Glu Ile Phe His Met Thr Tyr Asp Leu Ala Ser Ala Val Val Arg Ile
225                 230                 235                 240

Val Asn Leu Ile Gly Met Met Leu Leu Leu Cys His Trp Asp Gly Cys
                245                 250                 255

Leu Gln Phe Leu Val Pro Met Leu Gln Asp Phe Pro His Asp Cys Trp
            260                 265                 270

Val Ser Ile Asn Gly Met Val Asn Asn Ser Trp Gly Lys Gln Tyr Ser
        275                 280                 285

Tyr Ala Leu Phe Lys Ala Met Ser His Met Leu Cys Ile Gly Tyr Gly
    290                 295                 300

Arg Gln Ala Pro Val Gly Met Ser Asp Val Trp Leu Thr Met Leu Ser
305                 310                 315                 320

Met Ile Val Gly Ala Thr Cys Tyr Ala Met Phe Ile Gly His Ala Thr
                325                 330                 335

Ala Leu Ile Gln Ser Leu Asp Ser Ser Arg Arg Gln Tyr Gln Glu Lys
            340                 345                 350

Tyr Lys Gln Val Glu Gln Tyr Met Ser Phe His Lys Leu Pro Pro Asp
        355                 360                 365

Thr Arg Gln Arg Ile His Asp Tyr Tyr Glu His Arg Tyr Gln Gly Lys
    370                 375                 380

Met Phe Asp Glu Glu Ser Ile Leu Gly Glu Leu Ser Glu Pro Leu Arg
385                 390                 395                 400

Glu Glu Ile Ile Asn Phe Asn Cys Arg Lys Leu Val Ala Ser Met Pro
                405                 410                 415

Leu Phe Ala Asn Ala Asp Pro Asn Phe Val Thr Ser Met Leu Thr Lys
            420                 425                 430

Leu Arg Phe Glu Val Phe Gln Pro Gly Asp Tyr Ile Ile Arg Glu Gly
        435                 440                 445

Thr Ile Gly Lys Lys Met Tyr Phe Ile Gln His Gly Val Val Ser Val
    450                 455                 460

Leu Thr Lys Gly Asn Lys Glu Thr Arg Leu Ala Asp Gly Ser Tyr Phe
465                 470                 475                 480

Gly Glu Ile Cys Leu Leu Thr Arg Gly Arg Arg Thr Ala Ser Val Arg
                485                 490                 495

Ala Asp Thr Tyr Xaa Arg Leu Tyr Ser Leu
            500                 505
```

<210> SEQ ID NO 36
<211> LENGTH: 1040
<212> TYPE: DNA
<213> ORGANISM: Murine

<400> SEQUENCE: 36

```
tttttgggtt ttaaaattta ttttattttt aaaagcgtct ccgganantc tagtgcatgg     60

ccaggctaca agctactggg ccagcaactc tgtaggatta ttaatgacaa aaatgcaagg    120

accccatagt tgatggaaac ccagggatga agcagggctg tcccacagac ttaggctttg    180
```

-continued

```
tggagctgtc tgaaaaccca ggctgtggct ttggaagaag tgcagacaac cactgcccag    240
agtgacttaa ggttcataca accatccagc cacctaagca cccctacctt caagcatctt    300
gccagtccca ctttgtgtct gtttagcctg cttttctcct cccaagttag gagtcgggta    360
caccctggga cggagcaata agactggggt tggagttaat gtgtaaaata actgaaaaaa    420
acatctgggg ctggcaaacc tgtttgtctg gaaaacagcc ttccagatgt gcaggtatgg    480
aaacagacag tgcttagagc agtaagggac cttataccag ctaatcgttc attctcccaa    540
gtataaggag gaatctgggg gtgctgggtt agctgctgca ggcctaattg gggggtggaa    600
tgggagctct gagctcttcc ccgctttcgc agagatctgc ctgctgactc gaggtcggag    660
aacagccagt gtaagggctg acacctattg tcgcctctac tcgctcagcg tggaccactt    720
caatgcggtg cttgaggagt tcccaatgat gcgcagggct tttgagacgg tggccatgga    780
ccggcttcgg cgcatcggtg aggcctgttt actctgtctg ctctgggtcc tggctgggcc    840
tcatctcatg agcctagccc tggtgctttg acaccacatc ccagcccacc cagttccagt    900
ccatgcctcc agcaggctgt tagcactgtt gctcactaga cttagcccta gcgagaaatt    960
gccgtggagt gtctccccaa accctcattc cccgtgtcct tctgggtacc agttcttaac   1020
ctcacaattt tttattgata                                               1040
```

<210> SEQ ID NO 37
<211> LENGTH: 79
<212> TYPE: PRT
<213> ORGANISM: Murine

<400> SEQUENCE: 37

```
Glu Ile Cys Leu Leu Thr Arg Gly Arg Arg Thr Ala Ser Val Arg Ala
  1               5                  10                  15

Asp Thr Tyr Cys Arg Leu Tyr Ser Leu Ser Val Asp His Phe Asn Ala
             20                  25                  30

Val Leu Glu Glu Phe Pro Met Met Arg Arg Ala Phe Glu Thr Val Ala
         35                  40                  45

Met Asp Arg Leu Arg Arg Ile Gly Glu Ala Cys Leu Leu Cys Leu Leu
     50                  55                  60

Trp Val Leu Ala Gly Pro His Leu Met Ser Leu Ala Leu Val Leu
 65                  70                  75
```

<210> SEQ ID NO 38
<211> LENGTH: 2246
<212> TYPE: DNA
<213> ORGANISM: Human

<400> SEQUENCE: 38

```
aaggagcagg aaagggttaa aactgcaggc ttctggatta tccaccctta cagtgatttc     60
aggttttact gggatttaat aatgctcata atgatggttg gaaatctagt catcatacca    120
gttggaatca cattctttac agagcaaaca acaacaccat ggattatttt caatgtggca    180
tcagatacag ttttcctatt ggacctgatc atgaatttta ggactgggac tgtcaatgaa    240
gacagttctg aaatcatcct ggaccccaaa gtgatcaaga tgaattattt aaaaagctgg    300
tttgtggttg acttcatctc atccatccca gtggattata tctttcttat tgtagaaaaa    360
ggaatggatt ctgaagttta caagacagcc agggcccttc gcattgtgag gtttacaaaa    420
attctcagtc tcttgcgttt attacgactt tcaaggttaa ttagatacat acatcaatgg    480
gaagagatat tccacatgac atatgatctc gccagtgcag tggtgagaat ttttaatctc    540
```

-continued

```
atcggcatga tgctgctcct gtgccactgg gatggttgtc ttcagttctt agtaccacta      600
ctgcaggact tcccaccaga ttgctgggtg tctttaaatg aaatggttaa tgattcttgg      660
ggaaagcagt attcatacgc actcttcaaa gctatgagtc acatgctgtg cattgggtat      720
ggagcccaag ccccagtcag catgtctgac ctctggatta ccatgctgag catgatcgtc      780
ggggccacct gctatgccat gtttgtcggc catgccaccg ctttaatcca gtctctggat      840
tcttcgaggc ggcagtatca agagaagtat aagcaagtgg aacaatacat gtcattccat      900
aagttaccag ctgatatgcg tcagaagata catgattact atgaacacag ataccaaggc      960
aaaatctttg atgaggaaaa tattctcaat gaactcaatg atcctctgag agaggagata     1020
gtcaacttca actgtcggaa actggtggct acaatgcctt tatttgctaa tgcggatcct     1080
aattttgtga ctgccatgct gagcaagttg agatttgagg tgtttcaacc tggagattat     1140
atcatacgag aaggagccgt gggtaaaaaa atgtatttca ttcaacacgg tgttgctggt     1200
gtcattacaa atccagtaa agaaatgaag ctgacagatg gctcttactt tggagagatt     1260
tgcctgctga ccaaaggacg tcgtactgcc agtgttcgag ctgatacata ttgtcgtctt     1320
tactcacttt ccgtggacaa tttcaacgag gtcctggagg aatatccaat gatgaggaga     1380
gcctttgaga cagttgccat tgaccgacta gatcgaatag gaaagaaaaa ttcaattctt     1440
ctgcaaaagt tccagaagga tctgaacact ggtgttttca acaatcagga gaacgaaatc     1500
ctcaagcaga ttgtgaaaca tgacagggag atggtgcagg caatcgctcc catcaattat     1560
cctcaaatga caaccctgaa ttccacatcg tctactacga ccccgacctc ccgcatgagg     1620
acacaatctc caccggtgta cacagcgacc agcctgtctc acagcaacct gcactccccc     1680
agtcccagca cacagacccc ccagccatca gccatcctgt caccctgctc ctacaccacc     1740
gcggtctgca gccctcctgt acagagccct ctggccgctc gaactttcca ctatgcctcc     1800
cccaccgcct cccagctgtc actcatgcaa cagcagccgc agcagcaggt acagcagtcc     1860
cagccgccgc agactcagcc acagcagccg tccccgcagc cacagacacc tggcagctcc     1920
acgccgaaaa atgaagtgca caagagcacg caggcgcttc acaacaccaa cctgacccgg     1980
gaagtcaggc cattttccgc ctggcagccn tcgctgcccc atgaggtgtc cattttgatt     2040
tccagaccca tcccactgtg ggggagtccc tggcctccat ccctcaaccc gtgacggcgg     2100
tccccggaac gggccttcag gcaggggca ggagcactgt cccgcagcgc gtcaccttt       2160
tccgacagat gtngtcggga gccatccccc cgaaccgagg agtccttcca gcaccccttc     2220
cacttatcac accccatcct aaaaaa                                          2246
```

<210> SEQ ID NO 39
<211> LENGTH: 749
<212> TYPE: PRT
<213> ORGANISM: Human

<400> SEQUENCE: 39

Lys Glu Gln Glu Arg Val Lys Thr Ala Gly Phe Trp Ile Ile His Pro
 1               5                  10                  15

Tyr Ser Asp Phe Arg Phe Tyr Trp Asp Leu Ile Met Leu Ile Met Met
                20                  25                  30

Val Gly Asn Leu Val Ile Ile Pro Val Gly Ile Thr Phe Phe Thr Glu
            35                  40                  45

Gln Thr Thr Thr Pro Trp Ile Ile Phe Asn Val Ala Ser Asp Thr Val
        50                  55                  60

-continued

```
Phe Leu Leu Asp Leu Ile Met Asn Phe Arg Thr Gly Thr Val Asn Glu
 65                  70                  75                  80

Asp Ser Ser Glu Ile Ile Leu Asp Pro Lys Val Ile Lys Met Asn Tyr
                 85                  90                  95

Leu Lys Ser Trp Phe Val Val Asp Phe Ile Ser Ser Ile Pro Val Asp
            100                 105                 110

Tyr Ile Phe Leu Ile Val Glu Lys Gly Met Asp Ser Glu Val Tyr Lys
        115                 120                 125

Thr Ala Arg Ala Leu Arg Ile Val Arg Phe Thr Lys Ile Leu Ser Leu
    130                 135                 140

Leu Arg Leu Leu Arg Leu Ser Arg Leu Ile Arg Tyr Ile His Gln Trp
145                 150                 155                 160

Glu Glu Ile Phe His Met Thr Tyr Asp Leu Ala Ser Ala Val Val Arg
                165                 170                 175

Ile Phe Asn Leu Ile Gly Met Met Leu Leu Leu Cys His Trp Asp Gly
            180                 185                 190

Cys Leu Gln Phe Leu Val Pro Leu Leu Gln Asp Phe Pro Pro Asp Cys
        195                 200                 205

Trp Val Ser Leu Asn Glu Met Val Asn Asp Ser Trp Gly Lys Gln Tyr
    210                 215                 220

Ser Tyr Ala Leu Phe Lys Ala Met Ser His Met Leu Cys Ile Gly Tyr
225                 230                 235                 240

Gly Ala Gln Ala Pro Val Ser Met Ser Asp Leu Trp Ile Thr Met Leu
                245                 250                 255

Ser Met Ile Val Gly Ala Thr Cys Tyr Ala Met Phe Val Gly His Ala
            260                 265                 270

Thr Ala Leu Ile Gln Ser Leu Asp Ser Ser Arg Arg Gln Tyr Gln Glu
        275                 280                 285

Lys Tyr Lys Gln Val Glu Gln Tyr Met Ser Phe His Lys Leu Pro Ala
    290                 295                 300

Asp Met Arg Gln Lys Ile His Asp Tyr Tyr Glu His Arg Tyr Gln Gly
305                 310                 315                 320

Lys Ile Phe Asp Glu Glu Asn Ile Leu Asn Glu Leu Asn Asp Pro Leu
                325                 330                 335

Arg Glu Glu Ile Val Asn Phe Asn Cys Arg Lys Leu Val Ala Thr Met
            340                 345                 350

Pro Leu Phe Ala Asn Ala Asp Pro Asn Phe Val Thr Ala Met Leu Ser
        355                 360                 365

Lys Leu Arg Phe Glu Val Phe Gln Pro Gly Asp Tyr Ile Ile Arg Glu
    370                 375                 380

Gly Ala Val Gly Lys Lys Met Tyr Phe Ile Gln His Gly Val Ala Gly
385                 390                 395                 400

Val Ile Thr Lys Ser Ser Lys Glu Met Lys Leu Thr Asp Gly Ser Tyr
                405                 410                 415

Phe Gly Glu Ile Cys Leu Leu Thr Lys Gly Arg Arg Thr Ala Ser Val
            420                 425                 430

Arg Ala Asp Thr Tyr Cys Arg Leu Tyr Ser Leu Ser Val Asp Asn Phe
        435                 440                 445

Asn Glu Val Leu Glu Glu Tyr Pro Met Met Arg Arg Ala Phe Glu Thr
    450                 455                 460

Val Ala Ile Asp Arg Leu Asp Arg Ile Gly Lys Lys Asn Ser Ile Leu
465                 470                 475                 480

Leu Gln Lys Phe Gln Lys Asp Leu Asn Thr Gly Val Phe Asn Asn Gln
```

-continued

```
                485                 490                 495

Glu Asn Glu Ile Leu Lys Gln Ile Val Lys His Asp Arg Glu Met Val
            500                 505                 510

Gln Ala Ile Ala Pro Ile Asn Tyr Pro Gln Met Thr Thr Leu Asn Ser
        515                 520                 525

Thr Ser Ser Thr Thr Thr Pro Thr Ser Arg Met Arg Thr Gln Ser Pro
    530                 535                 540

Pro Val Tyr Thr Ala Thr Ser Leu Ser His Ser Asn Leu His Ser Pro
545                 550                 555                 560

Ser Pro Ser Thr Gln Thr Pro Gln Pro Ser Ala Ile Leu Ser Pro Cys
                565                 570                 575

Ser Tyr Thr Thr Ala Val Cys Ser Pro Pro Val Gln Ser Pro Leu Ala
            580                 585                 590

Ala Arg Thr Phe His Tyr Ala Ser Pro Thr Ala Ser Gln Leu Ser Leu
        595                 600                 605

Met Gln Gln Gln Pro Gln Gln Gln Val Gln Gln Ser Gln Pro Pro Gln
    610                 615                 620

Thr Gln Pro Gln Gln Pro Ser Pro Gln Pro Gln Thr Pro Gly Ser Ser
625                 630                 635                 640

Thr Pro Lys Asn Glu Val His Lys Ser Thr Gln Ala Leu His Asn Thr
                645                 650                 655

Asn Leu Thr Arg Glu Val Arg Pro Phe Ser Ala Trp Gln Pro Ser Leu
            660                 665                 670

Pro His Glu Val Ser Ile Leu Ile Ser Arg Pro His Pro Thr Val Gly
        675                 680                 685

Glu Ser Leu Ala Ser Ile Pro Gln Pro Val Thr Ala Val Pro Gly Thr
    690                 695                 700

Gly Leu Gln Ala Gly Gly Arg Ser Thr Val Pro Gln Arg Val Thr Phe
705                 710                 715                 720

Phe Arg Gln Met Xaa Ser Gly Ala Ile Pro Pro Asn Arg Gly Val Leu
                725                 730                 735

Pro Ala Pro Leu Pro Leu Ile Thr Pro His Pro Lys Lys
            740                 745


<210> SEQ ID NO 40
<211> LENGTH: 1792
<212> TYPE: DNA
<213> ORGANISM: Human

<400> SEQUENCE: 40

gcgaggaggc gggcccggcg ggggagccgc gcggcagcca ggccagcttc atgcagcgcc     60

agttcggcgc gctcctgcag ccgggcgtca acaagttctc gctgcggatg ttcggcagcc    120

agaaggccgt ggagcgcgag caggagcgcg tcaagtcggc gggggcctgg atcatccacc    180

cgtacagcga cttcaggttc tactgggact tcaccatgct gctgttcatg gtgggaaacc    240

tcatcatcat cccagtgggc atcaccttct tcaaggatga gaccactgcc ccgtggatcg    300

tgttcaacgt ggtctcggac accttcttcc tcatggacct ggtgttgaac ttccgcaccg    360

gcattgtgat cgaggacaac acggagatca tcctggaccc cgagaagatc aagaanaagt    420

atctgcgcac gtggttcgtg gtggtcttcg tgtcctccat ccccgtggac tacatcttcc    480

ttatcgtgga gaagggcatt gactccgagg tctacaagac ggcacgcgcc ctgcgcatcg    540

tgcgcttcac caaaatcctc agcctcctgc ggctgctgcg cctctcacgc ctgatccgct    600

acatccatca gtgggaggag atcttccaca tgacctatga cctggccagc gcggtgatga    660
```

-continued

```
ggatctgcaa tctcatcagc atgatgctgc tgctctgcca ctgggacggc tgcctgcagt    720

tcctggtgcc tatgctgcag gacttcccgc gcaactgctg ggtgtccatc aatggcatgg    780

tgaaccactc gtggagtgaa ctgtactcct tcgcactctt caaggccatg agccacatgc    840

tgtgcatcgg gtacggccgg caggcgcccg aaagcatgac ggacatctgg ctgaccatgc    900

tcagcatgat tgtgggtgcc acctgctacg ccatgttcat cggccacgcc actgccctca    960

tccagtcgct ggactcctcg cggcgccagt accaggagaa gtacaagcag gtggagcagt   1020

acatgtcctt ccacaagctg ccagctgact tccgccagaa gatccacgac tactatgaac   1080

accgttacca gggcaagatg tttgacgagg acagcatcct gggcgagctc aacgggcccc   1140

tgcgggagga gatcgtcaac ttcaactgcc ggaagctggt ggcctccatg ccgctgttcg   1200

ccaacgccga ccccaacttc gtcacggcca tgctgaccaa gctcaagttc gaggtcttcc   1260

agccgggtga ctacatcatc cgcgaaggca ccatcgggaa gaagatgtac ttcatccagc   1320

acggcgtggt cagcgtgctc actaagggca acaaggagat gaagctgtcc gatggctcct   1380

acttcgggga gatctgcctg ctcacccggg gccgccgcac ggcganccgtg cgggctgaca   1440

cctactgccg cctctattcc ctgagcgtgg acaacttcaa cgaagtgctg gaggagtacc   1500

ccatgatgcg gcgcgctttc gagacggtgg ccatcgaccg cctggaccgc atcggcaaga   1560

agaattccat cctcctgcac aaggtgcagc atgacctcaa ctcgggcgta ttcaacaacc   1620

aggagaacgc catcatccag gagatcgtca agtacgaccg cgagatggtg cagcaggccg   1680

agctgggtca gcgcgtgggc tttttcccgc cgccgccgcc gccgccgcag gtcacttcgg   1740

ccatcgccac gctgcagcag gcggcggcca tgagcttctg cccgcaggtg gc            1792
```

<210> SEQ ID NO 41
<211> LENGTH: 597
<212> TYPE: PRT
<213> ORGANISM: Human

<400> SEQUENCE: 41

```
Glu Glu Ala Gly Pro Ala Gly Glu Pro Arg Gly Ser Gln Ala Ser Phe
  1               5                  10                  15

Met Gln Arg Gln Phe Gly Ala Leu Leu Gln Pro Gly Val Asn Lys Phe
             20                  25                  30

Ser Leu Arg Met Phe Gly Ser Gln Lys Ala Val Glu Arg Glu Gln Glu
         35                  40                  45

Arg Val Lys Ser Ala Gly Ala Trp Ile Ile His Pro Tyr Ser Asp Phe
     50                  55                  60

Arg Phe Tyr Trp Asp Phe Thr Met Leu Leu Phe Met Val Gly Asn Leu
 65                  70                  75                  80

Ile Ile Ile Pro Val Gly Ile Thr Phe Phe Lys Asp Glu Thr Thr Ala
                 85                  90                  95

Pro Trp Ile Val Phe Asn Val Val Ser Asp Thr Phe Phe Leu Met Asp
            100                 105                 110

Leu Val Leu Asn Phe Arg Thr Gly Ile Val Ile Glu Asp Asn Thr Glu
        115                 120                 125

Ile Ile Leu Asp Pro Glu Lys Ile Lys Xaa Lys Tyr Leu Arg Thr Trp
    130                 135                 140

Phe Val Val Val Phe Val Ser Ser Ile Pro Val Asp Tyr Ile Phe Leu
145                 150                 155                 160

Ile Val Glu Lys Gly Ile Asp Ser Glu Val Tyr Lys Thr Ala Arg Ala
                165                 170                 175
```

-continued

```
Leu Arg Ile Val Arg Phe Thr Lys Ile Leu Ser Leu Leu Arg Leu Leu
            180                 185                 190

Arg Leu Ser Arg Leu Ile Arg Tyr Ile His Gln Trp Glu Glu Ile Phe
        195                 200                 205

His Met Thr Tyr Asp Leu Ala Ser Ala Val Met Arg Ile Cys Asn Leu
    210                 215                 220

Ile Ser Met Met Leu Leu Leu Cys His Trp Asp Gly Cys Leu Gln Phe
225                 230                 235                 240

Leu Val Pro Met Leu Gln Asp Phe Pro Arg Asn Cys Trp Val Ser Ile
                245                 250                 255

Asn Gly Met Val Asn His Ser Trp Ser Glu Leu Tyr Ser Phe Ala Leu
            260                 265                 270

Phe Lys Ala Met Ser His Met Leu Cys Ile Gly Tyr Gly Arg Gln Ala
        275                 280                 285

Pro Glu Ser Met Thr Asp Ile Trp Leu Thr Met Leu Ser Met Ile Val
    290                 295                 300

Gly Ala Thr Cys Tyr Ala Met Phe Ile Gly His Ala Thr Ala Leu Ile
305                 310                 315                 320

Gln Ser Leu Asp Ser Ser Arg Arg Gln Tyr Gln Glu Lys Tyr Lys Gln
                325                 330                 335

Val Glu Gln Tyr Met Ser Phe His Lys Leu Pro Ala Asp Phe Arg Gln
            340                 345                 350

Lys Ile His Asp Tyr Tyr Glu His Arg Tyr Gln Gly Lys Met Phe Asp
        355                 360                 365

Glu Asp Ser Ile Leu Gly Glu Leu Asn Gly Pro Leu Arg Glu Glu Ile
    370                 375                 380

Val Asn Phe Asn Cys Arg Lys Leu Val Ala Ser Met Pro Leu Phe Ala
385                 390                 395                 400

Asn Ala Asp Pro Asn Phe Val Thr Ala Met Leu Thr Lys Leu Lys Phe
                405                 410                 415

Glu Val Phe Gln Pro Gly Asp Tyr Ile Ile Arg Glu Gly Thr Ile Gly
            420                 425                 430

Lys Lys Met Tyr Phe Ile Gln His Gly Val Val Ser Val Leu Thr Lys
        435                 440                 445

Gly Asn Lys Glu Met Lys Leu Ser Asp Gly Ser Tyr Phe Gly Glu Ile
    450                 455                 460

Cys Leu Leu Thr Arg Gly Arg Arg Thr Ala Xaa Val Arg Ala Asp Thr
465                 470                 475                 480

Tyr Cys Arg Leu Tyr Ser Leu Ser Val Asp Asn Phe Asn Glu Val Leu
                485                 490                 495

Glu Glu Tyr Pro Met Met Arg Arg Ala Phe Glu Thr Val Ala Ile Asp
            500                 505                 510

Arg Leu Asp Arg Ile Gly Lys Lys Asn Ser Ile Leu Leu His Lys Val
        515                 520                 525

Gln His Asp Leu Asn Ser Gly Val Phe Asn Asn Gln Glu Asn Ala Ile
    530                 535                 540

Ile Gln Glu Ile Val Lys Tyr Asp Arg Glu Met Val Gln Gln Ala Glu
545                 550                 555                 560

Leu Gly Gln Arg Val Gly Phe Phe Pro Pro Pro Pro Pro Pro Pro Gln
                565                 570                 575

Val Thr Ser Ala Ile Ala Thr Leu Gln Gln Ala Ala Ala Met Ser Phe
            580                 585                 590
```

-continued

```
Cys Pro Gln Val Ala
        595


<210> SEQ ID NO 42
<211> LENGTH: 25
<212> TYPE: PRT
<213> ORGANISM: Murine

<400> SEQUENCE: 42

Tyr Ser Tyr Ala Leu Phe Lys Ala Met Ser His Met Leu Cys Ile Gly
  1               5                  10                  15

Tyr Gly Ala Gln Ala Pro Val Ser Met
             20                  25


<210> SEQ ID NO 43
<211> LENGTH: 25
<212> TYPE: PRT
<213> ORGANISM: Murine

<400> SEQUENCE: 43

Ile Pro Asp Ala Phe Trp Trp Ala Val Val Thr Met Thr Thr Val Gly
  1               5                  10                  15

Tyr Gly Asp Met Thr Pro Val Gly Val
             20                  25


<210> SEQ ID NO 44
<211> LENGTH: 25
<212> TYPE: PRT
<213> ORGANISM: Murine

<400> SEQUENCE: 44

Ile Pro Leu Gly Leu Trp Trp Ala Leu Val Thr Met Thr Thr Val Gly
  1               5                  10                  15

Tyr Gly Asp Met Ala Pro Lys Thr Tyr
             20                  25


<210> SEQ ID NO 45
<211> LENGTH: 25
<212> TYPE: PRT
<213> ORGANISM: Murine

<400> SEQUENCE: 45

Tyr Trp Thr Cys Val Tyr Phe Leu Ile Val Thr Met Ser Thr Val Gly
  1               5                  10                  15

Tyr Gly Asp Val Tyr Cys Glu Ile Val
             20                  25


<210> SEQ ID NO 46
<211> LENGTH: 25
<212> TYPE: PRT
<213> ORGANISM: Murine

<400> SEQUENCE: 46

Tyr Val Thr Ser Met Tyr Trp Ser Ile Thr Thr Leu Thr Thr Val Gly
  1               5                  10                  15

Tyr Gly Asp Leu His Pro Val Asn Thr
             20                  25


<210> SEQ ID NO 47
<211> LENGTH: 25
<212> TYPE: PRT
<213> ORGANISM: Drosophilia Melanogaster
```

-continued

<400> SEQUENCE: 47

Tyr Val Thr Ala Leu Tyr Phe Thr Met Thr Cys Met Thr Ser Val Gly
1 5 10 15

Phe Gly Asn Val Ala Ala Glu Thr Asp
20 25

<210> SEQ ID NO 48
<211> LENGTH: 25
<212> TYPE: PRT
<213> ORGANISM: Murine

<400> SEQUENCE: 48

Tyr Ile Ser Ser Leu Tyr Phe Thr Met Tyr Ser Leu Thr Ser Val Gly
1 5 10 15

Phe Gly Asn Ile Ala Pro Ser Thr Asp
20 25

<210> SEQ ID NO 49
<211> LENGTH: 25
<212> TYPE: PRT
<213> ORGANISM: Human

<400> SEQUENCE: 49

Tyr Val Thr Ala Leu Tyr Phe Thr Phe Ser Ser Leu Tyr Ser Val Gly
1 5 10 15

Phe Gly Asn Val Ser Pro Asn Thr Asn
20 25

<210> SEQ ID NO 50
<211> LENGTH: 23
<212> TYPE: PRT
<213> ORGANISM: Bovine

<400> SEQUENCE: 50

Tyr Val Tyr Ser Leu Tyr Trp Ser Thr Leu Thr Leu Thr Thr Ile Gly
1 5 10 15

Glu Thr Pro Pro Pro Val Arg
20

<210> SEQ ID NO 51
<211> LENGTH: 24
<212> TYPE: PRT
<213> ORGANISM: Human

<400> SEQUENCE: 51

Tyr Ile Arg Cys Tyr Tyr Phe Ala Val Lys Thr Leu Ile Thr Ile Gly
1 5 10 15

Gly Leu Pro Asp Pro Lys Thr Leu
20

<210> SEQ ID NO 52
<211> LENGTH: 48
<212> TYPE: PRT
<213> ORGANISM: Murine

<400> SEQUENCE: 52

Phe Val Thr Ala Met Leu Ser Lys Leu Arg Phe Glu Val Phe Gln Pro
1 5 10 15

Gly Asp Tyr Ile Ile Arg Glu Gly Ala Val Gly Lys Lys Met Tyr Phe
20 25 30

Ile Gln His Gly Val Ala Gly Val Ile Thr Lys Ser Ser Lys Glu Met

-continued 35 40 45

<210> SEQ ID NO 53
<211> LENGTH: 48
<212> TYPE: PRT
<213> ORGANISM: rat

<400> SEQUENCE: 53

Leu Leu Val Glu Leu Val Leu Lys Leu Arg Pro Gln Val Phe Ser Pro
1 5 10 15

Gly Asp Tyr Ile Cys Arg Lys Gly Asp Ile Gly Lys Glu Met Tyr Ile
20 25 30

Ile Lys Glu Gly Lys Leu Ala Val Val Ala Asp Asp Gly Val Thr Gln
35 40 45

<210> SEQ ID NO 54
<211> LENGTH: 50
<212> TYPE: PRT
<213> ORGANISM: bovine

<400> SEQUENCE: 54

Ile Leu Ser Lys Leu Ala Asp Val Leu Glu Glu Thr His Tyr Glu Asn
1 5 10 15

Gly Glu Tyr Ile Ile Arg Gln Gly Ala Arg Gly Asp Thr Phe Phe Ile
20 25 30

Ile Ser Lys Gly Lys Val Asn Val Thr Arg Glu Asp Ser Pro Asn Glu
35 40 45

Asp Pro
50

<210> SEQ ID NO 55
<211> LENGTH: 50
<212> TYPE: PRT
<213> ORGANISM: Bovine

<400> SEQUENCE: 55

Glu Arg Leu Thr Val Ala Asp Ala Leu Glu Pro Val Gln Phe Glu Asp
1 5 10 15

Gly Gln Lys Ile Val Val Gln Gly Glu Pro Gly Asp Glu Phe Phe Ile
20 25 30

Ile Leu Glu Gly Ser Ala Ala Val Ile Gln Arg Arg Ser Glu Asn Glu
35 40 45

Glu Phe
50

<210> SEQ ID NO 56
<211> LENGTH: 48
<212> TYPE: PRT
<213> ORGANISM: E. Coli

<400> SEQUENCE: 56

Thr Leu Glu Trp Phe Leu Ser His Cys His Ile His Lys Tyr Pro Ser
1 5 10 15

Lys Ser Thr Leu Ile His Gln Gly Glu Lys Ala Glu Thr Leu Tyr Tyr
20 25 30

Ile Val Lys Gly Ser Val Ala Val Leu Ile Lys Glu Glu Gly Lys Glu
35 40 45

<210> SEQ ID NO 57
<211> LENGTH: 33

-continued

<212> TYPE: PRT
<213> ORGANISM: Murine

<400> SEQUENCE: 57

Lys Thr Ala Arg Ala Leu Arg Ile Val Arg Phe Thr Lys Ile Leu Ser
1 5 10 15

Leu Leu Arg Leu Leu Arg Leu Ser Arg Leu Ile Arg Tyr Ile His Gln
20 25 30

Trp

<210> SEQ ID NO 58
<211> LENGTH: 33
<212> TYPE: PRT
<213> ORGANISM: Murine

<400> SEQUENCE: 58

Asn Gln Ala Met Ser Leu Ala Ile Leu Arg Val Ile Arg Leu Val Arg
1 5 10 15

Val Phe Arg Ile Phe Lys Leu Ser Arg His Ser Lys Gly Leu Gln Ile
20 25 30

Leu

<210> SEQ ID NO 59
<211> LENGTH: 33
<212> TYPE: PRT
<213> ORGANISM: Bovine

<400> SEQUENCE: 59

Lys Phe Gly Trp Asn Tyr Pro Glu Ile Arg Leu Asn Arg Leu Leu Arg
1 5 10 15

Ile Ser Arg Met Phe Glu Phe Phe Gln Arg Thr Glu Thr Arg Thr Asn
20 25 30

Ile

<210> SEQ ID NO 60
<211> LENGTH: 60
<212> TYPE: PRT
<213> ORGANISM: Murine

<400> SEQUENCE: 60

Pro Asn Phe Val Thr Ala Met Leu Ser Lys Leu Arg Phe Glu Val Phe
1 5 10 15

Gln Pro Gly Asp Tyr Ile Ile Arg Glu Gly Ala Val Gly Lys Lys Met
20 25 30

Tyr Phe Ile Gln His Gly Val Ala Gly Val Ile Thr Lys Ser Ser Lys
35 40 45

Glu Met Lys Leu Thr Asp Gly Ser Tyr Phe Gly Glu
50 55 60

<210> SEQ ID NO 61
<211> LENGTH: 65
<212> TYPE: PRT
<213> ORGANISM: E. Coli

<400> SEQUENCE: 61

Asp Pro Thr Leu Glu Trp Phe Leu Ser His Cys His Ile His Lys Tyr
1 5 10 15

Pro Ser Lys Ser Thr Leu Ile His Gln Gly Glu Lys Ala Glu Thr Leu
20 25 30

-continued

```
Tyr Tyr Ile Val Lys Gly Ser Val Ala Val Leu Ile Lys Asp Glu Glu
        35                  40                  45

Gly Lys Glu Met Ile Leu Ser Tyr Leu Asn Gln Gly Asp Phe Ile Gly
    50                  55                  60

Glu
65


<210> SEQ ID NO 62
<211> LENGTH: 61
<212> TYPE: PRT
<213> ORGANISM: Bovine

<400> SEQUENCE: 62

Asp Asn Glu Arg Ser Asp Ile Phe Asp Ala Met Phe Pro Val Ser Phe
 1               5                  10                  15

Ile Ala Gly Glu Thr Val Ile Gln Gln Gly Asp Glu Gly Asp Asn Phe
            20                  25                  30

Tyr Val Ile Asp Gln Gly Glu Met Asp Val Tyr Val Asn Asn Asn Glu
        35                  40                  45

Trp Ala Thr Ser Val Gly Glu Gly Gly Ser Phe Gly Glu
    50                  55                  60


<210> SEQ ID NO 63
<211> LENGTH: 66
<212> TYPE: PRT
<213> ORGANISM: Bovine

<400> SEQUENCE: 63

Lys Trp Glu Arg Leu Thr Val Ala Asp Ala Leu Glu Pro Val Gln Phe
 1               5                  10                  15

Glu Asp Gly Gln Lys Ile Val Val Gln Gly Glu Pro Gly Asp Glu Phe
            20                  25                  30

Phe Ile Ile Leu Glu Gly Ser Ala Ala Val Leu Gln Arg Arg Ser Glu
        35                  40                  45

Asn Glu Glu Phe Val Glu Val Gly Arg Leu Gly Pro Ser Asp Tyr Phe
    50                  55                  60

Gly Glu
65


<210> SEQ ID NO 64
<211> LENGTH: 62
<212> TYPE: PRT
<213> ORGANISM: Bovine

<400> SEQUENCE: 64

Ala Gly Leu Leu Val Glu Leu Val Ile Lys Leu Gln Pro Gln Val Tyr
 1               5                  10                  15

Ser Pro Gly Asp Tyr Ile Cys Lys Lys Gly Asp Ile Gly Arg Glu Met
            20                  25                  30

Tyr Ile Ile Lys Glu Gly Lys Leu Ala Val Val Ala Asp Asp Gly Ile
        35                  40                  45

Thr Gln Phe Val Val Leu Ser Asp Gly Ser Tyr Phe Gly Glu
    50                  55                  60


<210> SEQ ID NO 65
<211> LENGTH: 61
<212> TYPE: PRT
<213> ORGANISM: Rat

<400> SEQUENCE: 65
```

-continued

Ala Gly Leu Leu Val Glu Leu Leu Lys Leu Arg Pro Gln Val Tyr Ser
1 5 10 15

Pro Gly Asp Tyr Ile Cys Arg Lys Gly Asp Ile Gly Lys Glu Met Tyr
20 25 30

Ile Ile Lys Glu Gly Gln Leu Ala Val Val Ala Asp Asp Gly Val Thr
35 40 45

Gln Phe Ala Leu Leu Thr Ala Gly Gly Cys Phe Gly Glu
50 55 60

<210> SEQ ID NO 66
<211> LENGTH: 60
<212> TYPE: PRT
<213> ORGANISM: Drosophilia Melaogastar

<400> SEQUENCE: 66

Asp Gly Cys Leu Arg Ala Leu Ala Met His Phe Met Met Ser His Ser
1 5 10 15

Ala Pro Gly Asp Leu Leu Tyr His Thr Gly Glu Ser Ile Asp Ser Leu
20 25 30

Cys Phe Ile Val Thr Gly Ser Leu Glu Val Ile Gln Asp Asp Glu Val
35 40 45

Val Ala Ile Leu Gly Lys Gly Asp Val Phe Gly Asp
50 55 60

<210> SEQ ID NO 67
<211> LENGTH: 64
<212> TYPE: PRT
<213> ORGANISM: Arabidopsis Thaliana

<400> SEQUENCE: 67

Arg Asn Phe Leu Phe Gln Leu Val Ser Asp Ile Asp Ala Glu Tyr Phe
1 5 10 15

Pro Pro Lys Glu Asp Ile Ile Leu Gln Asn Glu Ala Pro Thr Asp Leu
20 25 30

Tyr Ile Leu Val Ser Gly Ala Val Asp Phe Thr Val Tyr Val Asp Gly
35 40 45

His Asp Gln Phe Gln Gly Lys Ala Val Ile Gly Glu Thr Phe Gly Glu
50 55 60

BRAIN AND HEART CYCLIC NUCLEOTIDE GATED ION CHANNEL COMPOUNDS AND USES THEREOF

This application is a continuation-in-part of U.S. Ser. No. 08/997,685, filed Dec. 23, 1997, now U.S. Pat. No. 6,551,821 the content of which is hereby incorporated into this application by reference.

Throughout this application, various publications are referenced by author and date. Full citations for these publications may be found listed alphabetically at the end of the specification immediately preceding the Sequence Listing and the claims. The disclosures of these publications in their entireties are hereby incorporated by reference into this application in order to more fully describe the state of the art.

BACKGROUND OF THE INVENTION

Introduction

Ion channels are a diverse group of proteins that regulate the flow of ions across cellular membranes. In the nervous system, ion channel activity has evolved into a rapid and accurate system for intercellular communication. The electrical excitability characteristics of each neuron is in part determined by the set of channels it expresses. However, cells are also able to regulate the activity of individual channels in response to physiological or developmental events, and there is growing evidence that ion channels can be the site of integration of multiple electrical and biochemical pathways.

In vivo, ion channels appear to be multimeric proteins that are comprised of several distinct gene families, coding for channels with distinct structural and functional properties.

Within a gene family, the potential for heterogeneity arising from the combinatorial assembly of different pore-forming and auxiliary subunits (Greene, et al., 1995). Channel properties can be modulated by second messenger cascades and can directly bind intracellular proteins such as kinases suggesting that this may be an important way to efficiently target the signaling cascade to its effector molecule. The electrical characteristics of each neuron is, in part, determined by the set of ion channels that it expresses. However, cells are also able to regulate the activity of individual channels in response to physiological or developmental events; pore-forming (α) subunits can interact with a variety of intracellular proteins, including auxiliary (β) subunits, cytoskeleton-associated proteins and protein kinases (Greene, et al., 1995). In addition to auxiliary (β) subunits, pore-forming subunits can interact with a variety of intracellular proteins and second messenger molecules themselves including G-proteins, cytoskeleton-associated proteins and protein-kinases (Adelman, et al., 1995).

Several classes of ion channels bind directly, and are regulated by, second messenger molecules such as cyclic nucleotides (Zagotta, et al., 1996; Bruggemann, et al., 1993, and Hoshi, et al., 1995) or $Ca^{+2}$ (Adelman, et al., 1992; Kohler, et al., 1996). Channels with this property may be key elements in the control of neuronal signaling, as they directly couple biochemical cascades with electrical activity. Cyclic nucleotide-gated channels (CNG) play a distinct role both in visual and olfactory signal transduction; their recent identification in the hippocampus and other regions of the brain, where cAMP and cGMP are known to mediate different forms of synaptic plasticity (Krapivinisky, et al., 1995; Frey, et al., 1993; Bolshakov, et al., 1997; and Arancio, et al., 1995), suggests that CNG-channels may also contribute to the regulation of excitability in central neurons (Kingston, et al., 1996 and Bradley, et al., 1997).

The first structural gene for a $K^+$ channel to be isolated was the gene encoded by the Shaker (Sh) locus in Drosophila melanogaster (Strong, et al., 1993; Papazian, et al., 1987). Its sequence is the prototype of a large and still expanding family of related genes (Kamb, et al., 1987; Warmke, et al., 1994). The properties of a number of well characterized $K^+$ currents, that still await a molecular definition, predicts that other members of this family are yet to be identified (Atkinson, et al., 1991).

Although the initial members of the $K^+$ channel superfamily were cloned by chromosomal localization of alleles responsible for functional defects (Sh, eag and slo from Drosophila; (Papazian, et al., 1987; Kamb, et al., 1987; Warmke, et al., 1991; Atkinson, et al., 1991) or following the purification of a relatively abundant protein such as the cGMP-channel from bovine retina (Liman, et al., 1994), the most widely used strategy for cloning new members of the $K^+$ channel superfamily is by homology to these sequences. Unfortunately, this approach is not well suited for identifying more divergent sequences and potentially new branches in the phylogenetic tree of the $K^+$ channel superfamily. Expression cloning in *Xenopus* oocytes can circumvent this problem; this implies a pre-existing or readily detectable physiological characterization of the channel.

SUMMARY OF THE INVENTION

The present invention provides an isolated nucleic acid encoding a BCNG protein or a portion thereof. The present invention further provides an isolated nucleic acid encoding a BCNG-related protein or a portion thereof. Further, the present invention provides a vector, which comprises cDNA encoding mBCNG-1 (ATCC Designation No. 209781). In addition, the present invention further provides a vector, which comprises cDNA encoding hBCNG-1 (ATCC Designation No. 209827). The present invention also provides an isolated BCNG protein. Further, the present invention also provides an isolated BCNG-related protein.

The present invention additionally provides a composition comprising a nucleic acid encoding a BCNG protein or a portion thereof, or a BCNG-related protein or a portion thereof and a carrier. In addition, the present invention further provides a composition comprising a BCNG protein or a portion thereof, or a BCNG-related protein or portion thereof and a carrier.

Additionally, the present invention provides a nucleic acid probe capable of specifically hybridizing with a nucleic acid encoding a BCNG protein or BCNG-related protein.

The present invention provides a method for identifying a nucleic acid in a sample which encodes a BCNG protein or a BCNG-related protein which comprises: (a) contacting the sample with a nucleic acid probe capable of specifically hybridizing with nucleic acid encoding a BCNG protein or a BCNG-related protein under conditions permissive to the formation of a complex between the nucleic acid probe and the nucleic acid encoding the BCNG protein or the BCNG-related protein in the sample; (b) determining the amount of complex formed in step (a); and (c) comparing the amount of complex determined in step (b) with the amount of complex formed using an arbitrary sequence, a greater amount of complex formed with the BCNG-specific probe indicating the presence of a nucleic acid encoding a BCNG protein or a BCNG-related protein in the sample.

Further, the present invention provides a method for testing whether a compound affects the expression of a BCNG protein or a BCNG-related protein which comprises: (a) contacting a sample which expresses a BCNG protein or a BCNG-related protein with a compound; (b) determining the amount of expression of BCNG protein or BCNG-related protein in the sample; and (c) comparing the amount of BCNG protein or BCNG-related protein expression determined in step (b) with the amount determined in the absence of the compound.

In addition, the present invention further provides a method for identifying a compound capable of interacting with a BCNG protein or a BCNG-related protein which comprises: (a) contacting a sample which expresses a BCNG protein or a BCNG-related protein with a compound under conditions permissive to formation of a complex between the compound and the BCNG protein or the BCNG-related protein; (b) determining the amount of complex formed between the compound and the BCNG protein or the BCNG-related protein; (c) comparing the amount of complex formed in step (b) with the amount formed in the absence of the compound, a greater amount of complex formed in the presence of the compound indicating the presence of a compound capable of interacting with a BCNG protein or a BCNG-related protein.

Also, the present invention provides a method for identifing a compound capable of modulating BCNG protein or BCNG-related protein activity which comprises: (a) contacting a sample which expresses a BCNG protein or a BCNG-related protein with a compound; (b) determining the amount of activity of the BCNG protein or BCNG-related protein in the sample; and (c) comparing the amount of activity of the BCNG protein or the BCNG-related protein determined in step (b) with the amount determined in the absence of the compound, an increase or decrease in activity indicating the presence of a compound capable of modulating the activity of the BCNG protein or the BCNG-related protein.

Further, the present invention also provides a method of treating a condition in a subject which comprises administering to the subject an amount of the provided compound, effective to treat the condition.

Finally, the present invention provides a pharmaceutical composition which comprises the provided compound and a pharmaceutically acceptable carrier.

BRIEF DESCRIPTION OF THE FIGURES

FIGS. 1A–1D. Primary structure of mBCNG-1. FIG. 1A. Deduced amino acid sequence (Seq.ID.No.:30) encoded by the mBCNG-1 cDNA. The seven hydrophobic domains, homologous to the six transmembrane domains (S1–S6) and the pore (P) of $K^+$ channels, are indicated ( ). The putative cyclic-nucleotide binding site (CNBs) is marked by an ( - - - ), C-terminal prolines ( . . . ) the consensus N-glycosylation site with presumptive extracellular localization (*) are also marked. FIG. 1B. Kyte and Doolittle hydropathy plot of the predicted amino acid sequence of mBCNG-1. The profile was generated by the Kyte and Doolittle method with a window size of 7 amino acids. The numbers on the top line indicate the position in the mBCNG-1 sequence. Hydrophobic regions corresponding to S1 through S6 and the P region lie below the zero line while the N-glycosylation site (*) is in a hydrophilic region between S5 and P. Numbering (top line) indicate position in the mBCNG-1 sequence. Profile generated with a window size of 7 residues. FIG. 1C (Seq.ID.Nos.:42–51). Multiple alignment of the putative P region of mBCNG-1 with the P regions of Drosophila Eag (DEAG), mouse Eag (MEAG), human Erg (HERG), α-subunit of bovine retinal CNG-channel (BRET-1), and β-subunit of human retinal CNG-channel (HRET-2). Arrowheads mark the residues 344 and 352 (see Example 1). FIG. 1D (Seq.ID.Nos.:52–56). Alignment of the (CNBs) of BCNG-1 with the corresponding site in the rat olfactory CNG-channel (ROLF-1), bovine cGMP-dependent protein kinase (PKG), bovine cAMP-dependent protein kinase (PKA), and catabolite activator protein of *E.coli* (CAP). Continuous lines mark α-helical (α) and β-strand (β) elements of the secondary structure elements of CAP, while asterisks indicate specific amino acids that appear to lie close to the cAMP molecule in the CAP crystal structure.

FIG. 2A. Western blot analysis of BCNG-1 protein in a mouse brain extract. Ten μg of a total brain SDS-extract was loaded per strip then probed with αq1 (1) or αq2 (3) antiserum or, strip 2 with αq1 (2) or αq2 (4) antiserum preadsorbed with the GST-d5 fusion protein. The arrow marks the position of the specific signal, of corresponding to the native mBCNG-1 protein. FIG. 2B. Western blot using the αq1 antiserum against: total brain extract (1), total brain extract pre-treated with N-glycosidase F (2) and in vitro translated mBCNG-1 protein (3). Positions of molecular weight standards are shown on the left. Also shown, Western blot containing 10 μg of proteins from each of the indicated brain tissues which was tested with antisera against mBCNG-1 and showing widespread expression of the mBCNG-1 protein in mouse brain. FIG. 2C. indicates reactivity with αq1. FIG. 2D. indicates reactivity with αq2.

FIGS. 5C–5D. mBCNG-1 immunoreactivity in the hippocampus. In FIG. 5C, the arrow shows the position of the hippocampal fissure; areas $CA_1$, $CA_3$ and dentate gyrus (DG) are labeled. FIG. 5D shows a detail of the *Stratum pyramidale* of area $CA_3$. FIGS. 5E–5F. mBCNG-1 immunoreactivity in the cerebellum. (FIG. 5A, FIG. 5C, FIG. 5E: 60X; FIG. 5B, FIG. 5D, FIG. 5F: 100X) magnification).

FIGS. 7A–7B. Predicted structure of mBCNG-1 (Santoro et al., 1997) with six transmembrane domains (S1–S6), pore region (P), cyclic nucleotide binding site (CNBs) and long C-terminal tail, including a polyglutamine stretch (Q). The predicted sequences encoded by the partial cDNA clones of three other mouse and two human BCNG genes are shown in a tentative alignment to mBCNG-1. Lines with double-headed arrows above the sequences indicate if the fragment was obtained from a cDNA library (λgt10 or pJG4–5), RT-PCR reaction, or EST database. Dashed lines with double-headed arrows underneath the sequences indicate the position of probes used herein (see Examples 1–5 in Experimental Details section). Hashed box in the 5' region of mBCNG-4 indicates the position of the probable intron in the M28-EST clone. FIG. 7C. Percent sequence similarity among the mouse and human BCNG genes. The alignments were performed by comparing only the core region of the proteins, corresponding to amino acids 111–419 (numbering according to mBCNG-1, see FIG. 8), and including transmembrane domains S1–S6. The mBCNG-4 sequence was not included in this alignment. However, limited alignment within the available cyclic nucleotide binding domain sequence of mBCNG-4 (aa 529–592, numbering according to mBCNG-1, see FIG. 8) shows a 79% similarity to mBCNG-1.

FIGS. 8A–8B. Mouse and human BCNG protein alignments. Tentative alignment of the predicted amino acid sequences for the four mouse (mBCNG-1, 2, 3 and 4) and two human genes (hBCNG-1 and 2). The proposed structural features of the protein (putative transmembrane regions, pore region and cyclic nucleotide binding site) are indicated (see also FIG. 5). (-) indicates residues identical to mBCNG-1; divergent residues are otherwise reported. (.) indicates a gap (or deletion) in the aligned sequences. (*) at end of sequence indicates stop codon. (*) above position 327 marks N-glycosylation site of mBCNG-1. The arrow marks the single consensus PKA phosphorylation site present in BCNG-1 and BCNG-2 (Seq.ID.Nos.:30–40).

FIGS. 10A–10B. Multiple human tissue Northern blot, containing 2 mg of polyA+ RNA from each of the following tissues: heart (He), brain (Br), placenta (Pl), lung (Lu) liver (Li), skeletal muscle (Mu), kidney (Ki) and pancreas (Pa), was hybridized to DNA fragments corresponding to the indicated BCNG genes. FIGS. 10C–10D. The same fragments were used to probe a human Brain Multiple Tissue blot, containg 2 μg of polyA+ RNA from each of the following tissues: amigdala (Am), caudate nucleus (Cn), corpus callosum (CC), hippocampus (Hi), total brain (Br), substantia nigra (SN), subthalamic nucleus (Sn) and thalamus (Th). Molecular size markers are indicated on the left.

FIG. 13A. Sequence alignment of functional cyclic nucleotide binding sites from catabolite activating protein (CAP, Aiba et al., 1982; Cossart & Gicquel, 1982), A and B sites of recombinant bovine R1α (PKAa and PKAb, Titani et al., 1984), bovine retinal channel α subunit (bRET1, Kaupp et al.,1989) and the catfish olfactory α subunit (fOLF1, Goulding et al., 1992) along with the putative cyclic nucleotide binding sites of drosophila Ether-a-gogo (dEAG, Warmke et al., 1991), Arabidopsis Thaliana K transport protein (KAT1, Anderson et al., 1992) and mBCNG-1 (Seq.ID.No.:61) (described herein) The six residues that are totally conserved across all of the binding sites whose functional competence has been unequivocally confirmed are marked by asterisks. The conserved arginine that forms an ionic bond with the cyclic nucleotide is indicated by an arrow labeled R559. The residue in the third (C) α-helix that has been shown to influence coupling of activation to cAMP versus cGMP binding is indicated by an arrow labeled D604 (the cGMP selective substitution in bRET1) (Seq.ID.Nos.:60–67). FIG. 13B. Schematic representation of the cyclic nucleotide binding site of bRET1 showing the critical interactions between the binding site and the cyclic nucleotide. This model of the binding pocket is based on the crystal structure of CAP and bovine R1α. The cGMP is shown bound in an extended—or anti-form with the cyclized phosphate making an ionic bond with Arginine559 (bRET1 numbering) and the purine ring forming favorable contacts with D604 in this cGMP selective channel.

FIG. 15A. Shows that Ih activation upon hyperpolarization following an action potential. As this is a non-selective cationic current, it carries an inward current at these potentials which leads to the depolarization of the cell back towards the threshold for firing of the next action potential. FIG. 15B. Shows the action of sympathetic and vagal stimulation on the activity of cardiocytes from the sinoatrial node—the pacemaker area of the heart. Norepinephrine (NE) leads to a shift in the activation of Ih towards more depolarized potentials which accelerates the return to the action potential firing threshold, and hence, leads to an acceleration of the firing rate. In contrast, acetylcholine (ACh) shifts the activation of Ih to more hyperpolarized potentials. Thus, the current will turn on later during the repolarization phase delaying the return to threshold—the firing rate of the cell will thus be slowed. These changes in the activation properties of Ih are thought to be due to changes in the concentration of cAMP with ACh lowering the concentration and NE increasing the concentration which has been shown to alter the activation properties of Ih. ("Principles of Neural Science" by Kandel, Schwartz and Jessell 1991).

FIG. 16A. Currents elicited by 3 s hyperpolarizations from a holding potential of −40 mV to potentials ranging from −60 to −130 mV in 5 mV increments. FIG. 16B. Relation between steady-state current at end of hyperpolarizing step and patch voltage. FIG. 16C. Tail currents recorded upon return to −40 mV following hyperpolarizations to various test voltages. Records shown on an expanded time scale to emphasize tail currents. FIG. 16D. Mean relation between tail current amplitude and voltage during hyperpolarizing step. For each patch, tail current data were normalized to the maximal tail current amplitude obtained from a fit of the Boltzmann equation (see Example 4, Experimental Details section). Normalized tail currents were then averaged for 5 patches. Mean V½=−100.0 mV, slope=5.8 mV. FIG. 16E. Activation time course of mBCNG-1 currents. Data were sampled at 5 kHz and the currents during voltage steps between −105 to −130 mV were fitted by single exponential functions (smooth lines), after allowing for an initial lag.

FIG. 16F. Relationship between mean time constants of activation and voltage. In the above experiments, the extracellular solution was KCl/NaCl-CaCl2, and the intracellular solution was KCl/NaCl-EGTA (See, Example 4, Experimental Procedures).

FIG. 17A. Tail currents obtained upon depolarizing steps to various test potentials following a 0.3 sec step to −130 mV to activate the mBCNG-1 current. Test potentials ranged from −60 to +20 mV in 5 mV increments (indicated next to alternate current traces) The extracellular solution was NaCl-EGTA while the intracellular solution was Kcl-EGTA. FIG. 17B. Similar tail current protocol used to measure reversal potential after switching to the low Cl, KAspartate-EGTA solution in the bath. FIG. 17C. Tail current amplitude as a function of membrane voltage during tail. Open symbols represent the current amplitudes determined with the KCl-EGTA solution in the bath (o, initial measurement, $E_{rev}$=−32.8±2.5, n=3; □, following washout of the KAspartate-EGTA solution, $E_{rev}$=−31.2±1.6, n=3). The filled circles represent the measurements made in the presence of the K-Aspartate solution ($E_{rev}$=−28.2±1.6, n=4). In all three panels, the zero current level is indicated by a horizontal dashed line.

In FIGS. 18A–18C, the current at the holding potential (−40 mV) and in response to a hyperpolarization to −130 mV are superimposed. FIGS. 18A and 18B. mBCNG-1 current records from an outside-out patch. Currents at the holding potential (−40 mV) and in response to a step to −130 mV are superimposed. The sequential records were obtained when the extracellular surface was exposed to the KCl/NaCl-CaCl2 solution (control), or solutions in which 2 mM CsCl iso-osmotically replaced NaCl or 1 mM BaCl2 replaced the CaCl2. The intracellular solution was Kcl/NaCl-EGTA. FIG. 18C. Dose response relationship for the inhibition of mBCNG-1 current by Cs. Data are the mean from 6 patches (not all determined at each concentration). The solid line shows a fit of the Hill equation, $I/Imax=1/\{1+(IC_{50}/[CS])^n\}$, where [Cs] is the Cs concentration, $IC_{50}$ is the half maximal inhibitory concentration of Cs, n is the Hill coefficient, I is the current in the presence of Cs and Imax is the uninhibited current. The fit yields an $IC_{50}$ of 201 μM and a Hill coefficient of 1.08.

FIG. 19A. mBCNG-1 current record from an inside-out patch in response to hyperpolarization to −100 mV in the absence or presence of 1 AM cAMP in the intracellular solution (KC1-EGTA). The extracellular solution was Kcl-CaCl2. FIG. 19B. Records from another patch in the absence and presence of 30 μM cAMP (same solutions as in A). FIG. 19C. (Left panel) Tail current activation curves in the absence and presence of 1 μM cAMP for the patch shown in panel A. Data were analyzed and plotted as described in FIG. 1D. Curves fit by Boltzmann relation with following parameters: 0 μM cAMP: $V_{1/2}$=−100 mV, slope=5.4 mV and $I_{tail,max}$=−33.8 pA; 1 μM cAMP: $V_{1/2}$=−98 mV, slope=5.3 and $I_{tail,max}$=−33.7 pA. (Right panel) Mean tail current activation curves for patches in absence (solid circles) and presence (open circles) of cAMP. Data averaged from 5 patches. cAMP concentrations range from 1–3000 μM, for cAMP, $V_{1/2}$=−98.3 mV, slope=6 mV.

FIGS. 20 A–C. mBCNG-2 is expressed in the sinoatrial node of the heart.

DETAILED DESCRIPTION OF THE INVENTION

Figure 1B:
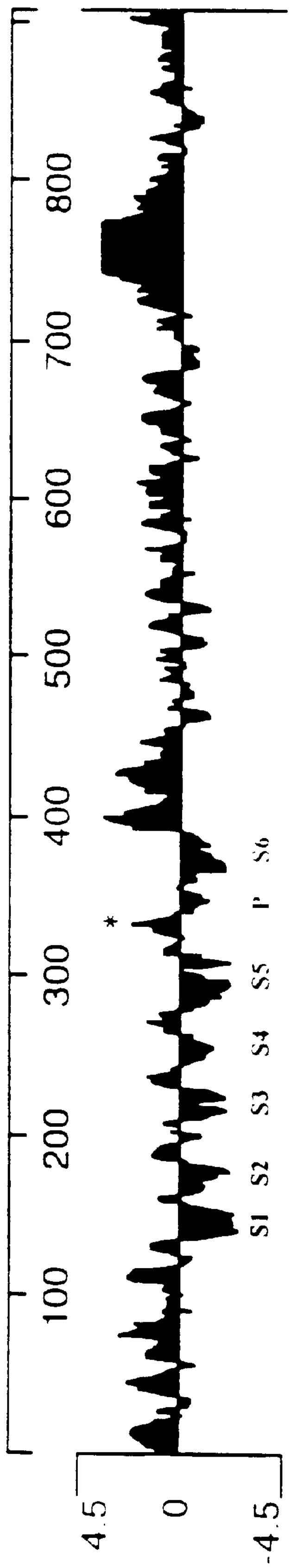

The present invention provides an isolated nucleic acid encoding a BCNG protein or a portion thereof. The present invention further provides an isolated nucleic acid encoding a BCNG-related protein or a portion thereof.

In an embodiment of this invention, the BCNG protein is encoded by the sequence shown in mBCNG-1 (ATCC DesignationNo.:1), mBCNG-2 (Seq.ID.No.:5), mBCNG-3 (Seq.ID.No.:9), mBCNG-4 (Seq.ID.No.:11), hBCNG-1 (ATCC Designation No. 209827) (Seq.ID.No.:3) or hBCNG-2 (Seq.ID.No.:7). According to an embodiment of this invention, the nucleic acid is DNA or RNA. In an embodiment of the present invention, the nucleic acid is cDNA. According to an embodiment of this invention, the cDNA has the nucleotide sequence shown in SEQ. ID. No.: 1 for mBCNG-1 (ATCC Accession No. 209781), SEQ. ID. No.: 3 for hBCNG-1, SEQ. ID. No.: 5 for mBCNG-2, SEQ. ID. No.: 7 for hBCNG-2, SEQ. ID. No.: 9 for mBCNG-3, or SEQ. ID. No.:11 for mBCNG-4. An embodiment of the present invention is a vector comprising the nucleic acid. According to an embodiment of this invention, the vector comprises viral or plasmid DNA. An embodiment of this invention comprises the nucleic acid and regulatory elements. One embodiment of this invention is a host vector system which comprises the provided expression vector in a suitable host.

Further, the present invention provides a vector, which comprises cDNA encoding mBCNG-1 (ATCC Designation No. 209781). In addition, the present invention further provides a vector, which comprises cDNA encoding hBCNG-1 (ATCC Designation No. 209827).

In an embodiment of this invention, the suitable host is a bacterial cell, a eukaryotic cell, a mammalian cell or an insect cell.

The present invention also provides an isolated BCNG protein. Further, the present invention also provides an isolated BCNG-related protein.

In one embodiment of this invention, the BCNG protein has the amino acid sequence shown in Seq.ID.No.:2 for mBCNG-1 (FIGS. 8A–8B), Seq.ID.No.:6 for mBCNG-2 (FIGS. 8A–8B), Seq.ID.No.:10 for mBCNG-3 (FIGS. 8A–8B), Seq.ID.No.12 for mBCNG-4 (FIGS. 8A–8B), Seq.ID.No.:4 for hBCNG-1 (FIGS. 8A–8B), or Seq.ID.No.:8 for hBCNG-2 (FIGS. 8A–8B). According to another embodiment of this invention, the BCNG-related protein has an amino acid sequence with substantial homology to the amino acid sequence shown in Seq.ID.No.:2 mBCNG-1 (FIGS. 8A–8B), Seq.ID.No.:6 for mBCNG-2 (FIGS. 8A–8B), Seq.ID.No.:10 for mBCNG-3 (FIGS. 8A–8B), Seq.ID.No.12 for mBCNG-4 (FIGS. 8A–8B), Seq.ID.No.:4 for hBCNG-1 (FIGS. 8A–8B), or Seq.ID.No.:8 for hBCNG-2 (FIGS. 8A–8B).

The present invention additionally provides a composition comprising a nucleic acid, encoding a BCNG protein or a portion thereof or a BCNG-related protein or a portion thereof and a carrier. In an embodiment of the present invention the nucleic acid comprises substantially the same coding sequence as the coding sequence shown in SEQ. ID. No.: 1 for mBCNG-1, SEQ. ID. No.: 3 for hBCNG-1, SEQ. ID. No.: 5 for mBCNG-2, SEQ. ID. No.: 7 for hBCNG-2, SEQ. ID. No.: 9 for mBCNG-3, SEQ. ID. No.:11 for mBCNG-4 or a portion of such coding sequence.

In addition, the present invention further provides a composition comprising a BCNG protein or portion thereof or a BCNG-related protein or portion thereof and a carrier.

In an embodiment of this invention the BCNG protein comprises the amino acid sequence shown in Seq.ID.No.:2 mBCNG-1 (FIGS. 8A–8B), Seq.ID.No.:6 for mBCNG-2 (FIGS. 8A–8B), Seq.ID.No.:10 for mBCNG-3 (FIGS. 8A–8B), Seq.ID.No.12 for mBCNG-4 (FIGS. 8A–8B), Seq.ID.No.:4 for hBCNG-1 (FIGS. 8A–8B), Seq.ID.No.:8 for hBCNG-2 (FIGS. 8A–8B).

Additionally, the present invention provides a nucleic acid probe capable of specifically hybridizing with a nucleic acid encoding a BCNG protein or BCNG-related protein. One embodiment of this invention is a nucleic acid probe capable of specifically hybridizing with the provided nucleic acid. According to an embodiment of this invention the probe is capable of specifically hybridizing with the nucleic acid sequence shown in Seq.ID.No:13, Seq.ID.No:14, Seq.ID.No:15, Seq.ID.No:16, Seq.ID.No:17, Seq.ID.No:18, Seq.ID.No:19, Seq.ID.No:20, Seq.ID.No:21, Seq.ID.No:21, Seq.ID.No:22, Seq.ID.No:23, Seq.ID.No:24, Seq.ID.No:25, Seq.ID.No:26, Seq.ID.No:27, Seq.ID.No:28, Seq.ID.No:29, Seq.ID.No:30, Seq.ID.No:31, Seq.ID.No:32, Seq.ID.No:33, or Seq.ID.No:34.

The present invention provides a method for identifying a nucleic acid in a sample which encodes a BCNG protein or a BCNG-related protein which comprises: (a) contacting the sample with a nucleic acid probe capable of specifically hybridizing with nucleic acid encoding a BCNG protein or a BCNG-related protein under conditions permissive to the formation of a complex between the nucleic acid probe and the nucleic acid encoding the BCNG protein or the BCNG-related protein in the sample; (b) determining the amount of complex formed in step (a); and (c) comparing the amount of complex determined in step (b) with the amount of complex formed using an arbitrary sequence, a greater amount of complex formed with the BCNG-specific probe indicating the presence of a nucleic acid encoding a BCNG protein or a BCNG-related protein in the sample.

In one embodiment of this invention, step (a) further comprises amplifying the nucleic acid molecule encoding the BCNG protein or the BCNG-related protein. According to an embodiment of this invention, the amplification comprises contacting the nucleic acid molecule from the sample with at least one amplification primer capable of specifically hybridizing to mBCNG-1 (Seq.ID.No.:1), mBCNG-2 (Seq.ID.No.:5), mBCNG-3 (Seq.ID.No.:9), mBCNG-4 (Seq.ID.No.:11), hBCNG-1 (Seq.ID.No.:3) or hBCNG-2 (Seq.ID.No.:7) under conditions suitable for polymerase chain reaction. In an embodiment of this invention, the amplified nucleic acid molecule encoding the BCNG protein or the BCNG-related protein is detected by size fractionation. One embodiment of this invention further comprises isolating the complex by size fractionation. According to an embodiment of this invention, the nucleic acid probe is labeled with a detectable marker. In an embodiment of this invention, the detectable marker is a radiolabeled molecule, a fluorescent molecule, an enzyme, a ligand, or a magnetic bead. According to an embodiment of this invention, the probe comprises the nucleotide sequence shown in Seq.ID.No:13, Seq.ID.No:14, Seq.ID.No:15, Seq.ID.No:16, Seq.ID.No:17, Seq.ID.No:18, Seq.ID.No:19, Seq.ID.No:20, Seq.ID.No:21, Seq.ID.No:21, Seq.ID.No:22, Seq.ID.No:23, Seq.ID.No:24, Seq.ID.No:25, Seq.ID.No:26, Seq.ID.No:27, Seq.ID.No:28, Seq.ID.No:29, Seq.ID.No:30, Seq.ID.No:31, Seq.ID.No:32, Seq.ID.No:33, or Seq.ID.No:34. In an embodiment of the present invention, the nucleic acid probe is capable of specifically hybridizing to nucleic acid encoding mBCNG-1 (Seq.ID.No.:1), mBCNG-2 (Seq.ID.No.:5), mBCNG-3 (Seq.ID.No.:9), mBCNG-4 (Seq.ID.No.:11), hBCNG-1 (Seq.ID.No.:3) or hBCNG-2 (Seq.ID.No.:7). The present invention also provides an isolated nucleic acid, previously unknown, identified by the provided amplification method. In one embodiment, the sample comprises cells or cell extract or cell lysate or a tissue sample or a biological fluid sample.

Further, the present invention provides a method for testing whether a compound modulates the expression of a BCNG protein or a BCNG-related protein which comprises: (a) contacting a sample which expresses a BCNG protein or a BCNG-related protein with a compound; (b) determining the amount of expression of BCNG protein or BCNG-related protein in the sample; and (c) comparing the amount of BCNG protein or BCNG-related protein expression determined in step (b) with the amount determined in the absence of the compound thereby determining whether the compound modulates BCNG protein expression or BCNG-related protein expression. The present invention provides such a method for screening a large number of compounds to determine whether one or more of the compounds modulates the activity of a BCNG protein or a BCNG-related protein or modulates the expression of the nucleic acid encoding either the BCNG protein or the BCNG-related protein.

In addition, the present invention further provides a method for identifying a compound capable of interacting with a BCNG protein or a BCNG-related protein which comprises: (a) contacting a sample which expresses a BCNG protein or a BCNG-related protein with a compound under conditions permissive to formation of a complex between the compound and the BCNG protein or the BCNG-related protein; (b) determining the amount of complex formed between the compound and the BCNG protein or the BCNG-related protein; (c) comparing the amount of complex formed in step (b) with the amount formed in the absence of the compound, a greater amount of complex formed in the presence of the compound indicating the presence of a compound capable of interacting with a BCNG protein or a BCNG-related protein.

Also, the present invention provides a method for identifing a compound capable of modulating BCNG protein or BCNG-related protein activity which comprises: (a) contacting a sample which expresses a BCNG protein or a BCNG-related protein with a compound; (b) determining the amount of activity of the BCNG protein or BCNG-related protein in the sample; and (c) comparing the amount of activity of the BCNG protein or the BCNG-related protein determined in step (b) with the amount determined in the absence of the compound, an increase or decrease in activity indicating the presence of a compound capable of modulating the activity of the BCNG protein or the BCNG-related protein.

The present invention also provides for compounds or compositions which are identified through the compound screening methods described herein, as capable of modulating the activity or expression of BCNG protein or BCNG related protein.

An embodiment of this invention is step (a) comprising first introducing the nucleic acid encoding a BCNG protein or a BCNG-related protein into an expression system and causing the expression system to express the nucleic acid under conditions whereby a BCNG protein or a BCNG-related protein is produced. Another embodiment of this invention is wherein step (b) comprises measuring the channel electrical current or intracellular calcium level in the presence of the compound. In yet another embodiment of this invention, the expression system comprises a cultured host cell.

In an embodiment of this invention, the BCNG protein comprises the amino acid sequence of mBCNG-1 (Seq.ID.No.:2), mBCNG-2 (Seq.ID.No.:6), mBCNG-3 (Seq.ID.No.:10), mBCNG-4 (Seq.ID.No.:12), hBCNG-1 (Seq.ID.No.:4) or hBCNG-2 (Seq.ID.No.:8) or a portion thereof. In one embodiment of the present invention, the sample comprises a cell, cell lysate or cell-free translation. In another embodiment, the cell is a cardiac cell, a kidney cell, a hepatic cell, an airway epithelial cell, a muscle cell, a neuronal cell, a glial cell, a microglial cell, an endothelial cell, a mononuclear cell, a tumor cell, a mammalian cell, an insect cell, or a *Xenopus* oocyte.

The present invention further provides a compound, previously unknown, identified by the screening methods herein. According to one embodiment, the compound is a peptide, a peptidomimetic, a nucleic acid, a polymer, or a small molecule. The small molecule may be an organic or an inorganic molecule. The small molecule may have a molecular weight less than that of a BCNG protein. According to an embodiment of the present invention, the compound is bound to a solid support. In one embodiment of the present invention, the BCNG protein or the BCNG-related protein is ion channel protein or a protein which is a subunit of an ion channel subunit protein. In one embodiment the BCNG-related protein is a component which is needed to create a pacemaker current in and among cells. In an embodiment of the present invention, the compound is an agonist or antagonist of ion channel activity.

According to an embodiment of the present invention, the modulation is increased ion flow rate or decreased ion flow rate. According to another embodiment, the modulation is increased ion permissivity or decreased ion permissivity.

The present invention also further provides a method of modulating BCNG protein activity or BCNG-related protein activity in a sample, comprising contacting the sample with the provided compound.

Further, the present invention also provides a method of treating a condition in a subject which comprises administering to the subject an amount of the provided compound, effective to treat the condition. The condition comprises an abnormal condition. The abnormal condition may be a loss of memory, a cardiac condition, a hepatic condition, a problem with cellular secretions, a pancreatic condition, a pacemaker condition in brain, or a pacemaker condition in non-neuronal cells.

The present invention additionally provides a pharmaceutical composition which comprises the provided compound and a pharmaceutically acceptable carrier. In an embodiment of this invention, the carrier is a diluent, an aerosol, a topical carrier, an aqueous solution, a nonaqueous solution or a solid carrier.

The present invention also additionally provides a method for treating a condition in a subject which comprises administering to the subject an amount of the provided pharmaceutical composition, effective to treat the condition in the subject.

In an embodiment of the present invention, the condition is a neurological, renal, pulmonary, hepatic, or cardiovascular condition. According to an embodiment of this invention, the condition is epilepsy, Alzheimer's Disease, Parkinson's Disease, long QT syndrome, sick sinus syndrome, age-related memory loss, cystic fibrosis, sudden death syndrome, hyperalgesia, ventricular or atrial arrhythmias, familial sinus node disease or a pacemaker rhythm dysfunction. In a further embodiment of this invention, the subject is a human. Certain additional methods for treating diseases in a subject are discussed hereinbelow. Long QT disease is a cardiac disease wherein action potentials last longer than they normally should. Sick sinus disease is an acquired disease (e.g. after atrial fibrilation) wherein the sinus node does not function normally.

The present invention additionally also provides an antibody which binds specifically to a BCNG protein or a BCNG-related protein. The present invention further provides a cell capable of producing the antibody. The present invention also provides a method of identifying a BCNG protein or a BCNG related protein in a sample comprising: a) contacting the sample with an antibody under conditions permissive to the formation of a complex between the antibody and the protein; b) determining the amount of complex formed; and c) comparing the amount of complex formed in step (b) with the amount of complex formed in the absence of the antibody, the presence of an increased amount of complex formed in the presence of the antibody indicating identification of the protein in the sample.

As used herein, the term "BCNG protein" encompasses a protein having an amino acid sequence substantially similar to or identical to mBCNG-1, mBCNG-2, mBCNG-3, mBCNG-4, hBCNG-1 or hBCNG-2. An example of a BCNG protein is mBCNG-1, mBCNG-2, mBCNG-3, mBCNG-4, hBCNG-1 or hBCNG-2. A BCNG protein may be a homolog of mBCNG-1, mBCNG-2, mBCNG-3, mBCNG-4, hBCNG-1 or hBCNG-2 in a species other than mouse or human. Alternatively a BCNG protein may be another member of the family of BCNG proteins in mouse, human or other mammalian or non-mammalian species. A BCNG protein may function as an integral component or subunit of an ion channel. A BCNG protein may be an accessory protein or a non-functional protein associated with an ion channel.

The term "BCNG-related protein" encompasses a protein having substantial homology to at least one functional domain of a BCNG protein as described herein. (See, Example 3, FIG. 11 and FIG. 13). For example, the hydrophobic core is one such domain (See, Example 3, subsection "The Hydrophobic Core"). Another example of a functional domain is the S4 voltage-sensing domain (See, Example 3, subsection "The S4 voltage-sensing domain). Still another example of a functional domain is the cyclic nucleotide binding site (See, Example 3, subsection "The cyclic nucleotide binding site). Yet another example is the pore domaine ((See, Example 3, subsection "The pore"). A BCNG-related protein may thus function as an integral component or subunit of an ion channel. A BCNG-related protein may be an accessory protein or a non-functional protein associated with an ion channel. A BCNG-related protein is defined by a sequence or structural homology with a BCNG protein or portion thereof. Thus, a BCNG protein is a BCNG-related protein, but a BCNG-related protein is not limited to BCNG proteins.

The amino acid sequence of mBCNG-1 is presented as Seq.ID.No.:2. This sequence has been deposited in the GenBank database and accorded the GenBank Accession Number:AF028737.

A BCNG protein exhibits substantial sequence similarity to mBCNG-1. A BCNG-related protein exhibits substantial homology or functional relatedness to mBCNG-1. Substantial sequence homology includes consideration to conserved amino acid substitutions as understood by one of skill in the art. Functional relatedness may be gleaned from domains or regions of sequence having similarity, separated by regions with no apparent homology.

The present invention provides a composition comprising a BCNG protein or portion thereof, a BCNG-related protein or portion thereof, a nucleic acid encoding a BCNG protein or portion thereof, a nucleic acid encoding a BCNG related protein or portion thereof, an antibody to a BCNG protein or portion thereof, an antibody to a BCNG related protein or portion thereof, an nucleic acid with a sequence antisense to a portion of either a BCNG protein or a BCNG related protein or any other described compounds of the present invention. The composition may further comprise a carrier. The carrier may be a pharmaceutically acceptable carrier.

As used herein, a "portion thereof" is a sequence (e.g. am amino acid sequence or a nucleotide sequence) which comprises less than the entire sequence. For example, in reference to Seq.ID.No.: 2, amino acids 35–45 represent a portion thereof.

As used herein, the term "specifically hybridize" means that a nucleic acid probe hybridizes to a nucleic acid sequence having substantial homology with that of the probe. The sequence need not be identical or unique. However, the sequence must indicate a structural or functional relationship between the sequences as is understood in the art.

Hybridization can distinguish between closely-related and distantly-related members of a gene family. Reaction conditions can be adjusted to optimize hybridization of one species and minimize hybridization of others.

For a poorly-matched hybrid, the hybridization is lower and the hybridization curve is displaced towards lower temperatures. When the ratio of rate constants (discrimination ratio) for cross-hybridization and for self-hybridization is plotted against temperature of reaction, a sigmoidal curve is obtained. At low temperatures, the ratio is high while at higher temperatures (approaching $T_m$–20° C. for perfectly-matched hybrids), the ratio approaches zero. The relationship is useful in that it predicts that it should be easier to distinguish between distantly related sequences by incubating at low temperatures while it should be easier to distinguish closely related sequences by hybridizing at high temperatures.

In order, to distinguish between the distantly-related members of a family of sequences, hybridization should take place at a more permissive (relaxed) criterion. To detect closely-related members, the hybridization should be at a stringent criterion. A single compromise criterion will not be effective because, different members of the family probably have different discrimination versus temperature curves. Hybridization at a relaxed criterion followed by washing under progressively more stringent conditions may be useful for detecting distantly-related members of a family, but is not suitable for identifying closely-related members. This is probably because hybridization and washing depend on different parameters. Hybridization depends on the nucleation frequency while washing depends on the thermal stability ($T_m$) of the hybrids. Thus, a stringent hybridization followed by a stringent wash is better for detecting closely-related members of a family than permissive hybridization and a stringent wash.

The degree of hybridization depends on the degree of complementarity, the length of the nucleic acid molecules being hybridized, and the stringency of the conditions in a reaction mixture. Stringency conditions are affected by a variety of factors including, but not limited to temperature, salt concentration, concentration of the nucleic acids, length of the nucleic acids, sequence of the nucleic acids and viscosity of the reaction mixture. More stringent conditions require greater complementarity between the nucleic acids in order to achieve effective hybridization.

A preferred method of hybridization is blot hybridization. See Sambrook et al. 1989 *Molecular Cloning: A Laboratory Manual* 2nd Ed. for additional details regarding blot hybridization.

As used herein, a nucleic acid probe is a nucleic acid which specifically hybridizes to a particular nucleic acid sequence. The probe may be bound nonspecifically to a solid matrix. The nucleic acid probe may be DNA or RNA and can be labeled with a detectable marker. Such labeling techniques methods include, but are not limited to, radiolabeling, digoxygenin-labeling, and biotin-labeling. A well-known method of labeling DNA is $^{32}$p using DNA polymerase, Klenow enzyme or polynucleotide kinase. In addition, there are known non-radioactive techniques for signal amplification including methods for attaching chemical moieties to pyrimidine and purine rings (Dale, R. N. K. et al., 1973 *Proc. Natl. Acad. Sci. USA* 70:2238–42), methods which allow detection by chemiluminescence (Barton, S. K. et al., 1992 *J. Am. Chem. Soc.* 114:8736–40) and methods utilizing biotinylated nucleic acid probes (Johnson, T. K. et al., 1983 *Anal. Biochem.* 133:125–131; Erickson, P.

F. et al., 1982 *J. Immunol. Methods* 51:241–49; Matthaei, F. S. et al., 1986 *Anal. Biochem.* 157-123-28) and methods which allow detection by fluorescence using commercially available products. Non-radioactive labeling kits are also commercially available.

Nucleic acid amplification is described in Mullis, U.S. Pat. No. 4,683,202, which is incorporated herein by reference.

In a polymerase chain reaction (PCR), an amplification reaction uses a template nucleic acid contained in a sample can use one or more probe ("primer") sequences and inducing agents.

Suitable enzymes to effect amplification, specifically extension include, for example, *E.coli* DNA polymerase I, thermostable *Taq* DNA polymerase, Klenow fragment of *E.coli* DNA polymerase I, T4 DNA polymerase, other available DNA polymerases, reverse transcriptase and other enzymes which will facilitate covalent linkage of the nucleotides to polynucleotides which are form amplification products. Oligonucleotide probes (primers) can be synthesized by automated instruments sold by a variety of manufacturers or can be commercially prepared.

Solid matrices are available to the skilled artisan. A solid matrix may include polystyrene, polyethylene, polypropylene, polycarbonate, or any solid plastic material in the shape of test tubes, beads, microparticles, dip-sticks, plates or the like. Additionally matrices include, but are not limited to membranes, 96-well microtiter plates, test tubes and Eppendorf tubes. Solid phases also include glass beads, glass test tubes and any other appropriate shape made of glass. A functionalized solid phase such as plastic or glass which has been modified so that the surface carries carboxyl, amino, hydrazide, or aldehyde groups can also be used. In general such matrices comprise any surface wherein a ligand-binding agent can be attached or a surface which itself provides a ligand attachment site.

As used herein, the term "modulation" in reference to modulation of protein activity or ion channel activity refers to the up-regulation or down-regulation of the activity. Up-regulation includes, but is not limited to increased ion flow in the case of an ion channel. Down-regulation includes, but is not limited to decreased ion flow in the case of an ion channel. For example, one form of modulation of activity would be a channel-blocking protein or compound which inhibits ion flow through the channel, decreasing activity. Alternatively, another form of modulation is a channel-opening protein or compound which facilitates flow through the channel, increasing activity. In addition, the nature of the ion flow through a channel may be modulated. For example, proteins or compounds may alter a channel refractive to potassium flow to become permissive to potassium flow in addition to or in place of another ion. The term modulation is also used to describe the increase or decrease of gene expression.

In the practice of any of the methods of the invention or in the preparation of any of the pharmaceutical compositions of the present invention a "therapeutically effective amount" is an amount which is capable of modulating the activity or function of a BCNG-related protein. Accordingly, the effective amount will vary with the subject being treated, as well as the condition to be treated. The methods of administration may include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The carrier includes a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The invention provides nucleic acids comprising cDNA encoding BCNG protein as listed below:

| Plasmid name | ATCC Designation No. | Date of Deposit |
|---|---|---|
| mBCNG-1 | 209781 | Apr. 21, 1998 |
| mBCNG-2a | 209825 | May 1, 1998 |
| mBCNG-2b | 209826 | May 1, 1998 |
| mBCNG-3a | 209824 | May 1, 1998 |
| mBCNG-3b | 209828 | May 1, 1998 |
| hBCNG-1 | 209827 | May 1, 1998 |
| hBCNG-2 | 209787 | May 1, 1998 |

The above-identified plasmids, provided by the present invention, were deposited with The American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

Treatment of Diseases or Conditions in a Subject

The compounds and compositions of the present invention may be administered to a subject to treat a disease or condition which is associated with pacemaker function. The compounds and compositions comprises not only BCNG proteins or BCNG related proteins and nucleic acids encoding the same or portions thereof, but also compounds identified by the screening methods of the present invention. For example, a compound useful in the present invention may be a peptide, a small molecule (organic or inorganic), a peptidomimetic, or other compound as described hereinabove.

For example, the compounds and compositions of the present invention may be useful for treating memory deficits or disorders. Such memory disorders or deficits may involve an abnormal pacemaking function in the cells of the brain and the central nervous system. The memory disorder or deficit may be due to Alzheimer's disease, Parkinsons's Disease, or age-related memory loss.

The present invention provides for a method for treating a sensory disorder in a subject comprising administering to the subject compounds or compositions of the present invention. Such sensory disorders include sensory disorders of the eyes (blindness, loss of vision), of the nose (loss of smell), touch (numbness), and taste (lack of ability to taste).

In another example, the present invention provides for a method for treating a subject suffering from an auditory disorder which comprises administering an amount of the compounds or compositions of the present invention. It is shown hereinbelow that BCNG isoforms are expressed in the tissues of the auditory system in signifcant amounts. It may be possible to change the response characteristics of the cells of the auditory systems by regulation of the BCNG genes in these auditory tissues and cells. Thus, administration of nucleic acids or proteins (for example via a localized virus vector, or via a liposome carrying protein) to the subject would treat such an auditory disorder. The auditory disorder may be deafness or loss of hearing.

In another embodiment, the present invention provides for a method for treating a subject suffering from a respiratory disorder either due to defects in CNS (central nervous system) areas that control respiration or due to defects in the lung, which comprises administering to the subject an amount of a compound or composition of the present invention. Preferably, the compound comprises the BCNG isoform or a compound (e.g. a small molecule) which interacts with the BCNG isoform, which is normally expressed in lung tissue and/or brain nuclei important for respiratory control. The respiratory disorder may be Sudden Infant Death Syndrome, or any difficulty in regular breathing (e.g. shortness of breath). The repiratory disorder may be asthma.

The present invention provides a method for the treatment of dyslexia in a subject which comprises administering to the subject a compound or composition of the present invention in an amount effective to treat the dylexia in the subject. The present invention also provides methods for treatment of attention deficit disorder or learning disabilities. Learning related disorders may result from abnormal functioning (either increased or decreased) of ion channels present in the thalamus. This region of the brain is considered to be involved in wakefulness, attention and arousal. Disorders involving abnormal states of such functions may be treatable using the compounds and pharmacuetical compositions of the present invention.

The present invention provides a method for treating symptoms of drug addiction in a subject which comprises administering to the subject a composition of the present invention to thereby modulate ion channel function in the subject and treat the symptoms of drug addiction in the subject.

The present invention provides a method for regulating the secretions of a cell which normally produces secretions in a subject suffering from abnormal secretions or lack of secretions which comprises administering to the subject a therapeutically effective amount of a compound or composition of the present invention in order to regulate the secretions of the cell. The compound or composition may regulate the resting phase or the secretion phase of the cell so as to regulate when the cell produces secretions. The cell may be a pancreatic cell, a liver cell or a spleen cell.

The present invention provides a method for regulating rebound excitation in non-pacemaking cells.

The BCNG proteins are useful targets for screens for drugs that are effective in the control of pain and hyperalgesia. Pacemaker type channels with properties similar to those of the expressed BCNG-1 protein have been identified in primary afferent sensory neurons, where the channels are activated by prostaglandin E2, a hyperalgesia-inducing agent released during inflammation (Ingram and Williams, 1996). The channels have been proposed to play a role in pain perception and hypersensitivity to painful stimuli. The present invention provides a method for treating pain in a subject which comprises administering to the subject an amount of the composition of the present invention The BCNG channel isoforms expressed in cardiac ventricular muscle, including BCNG-2, are useful targets for screens for drugs that are effective in treating ventricular and/or atrial arrhythmias due to abnormal pacemaker activity in these tissues. Pacemaker channels with abnormal activation properties are detected in non-pacemaking regions of the heart, including ventricle, during heart failure (Cerbai et al., 1994, 1997).

The BCNG gene isoforms expressed in sinoatrial node can provide a useful genetic screen for inherited diseases of cardiac pacemaker function such as familial sinus node disease. Certain familial, inherited cardiac diseases are thought to involve defects in pacemaker channel function in the sinoatrial node (Spellberg, 1971).

The BCNG isoforms expressed in heart will be useful to screen for improved drugs that can limit heart muscle damage during episodes of ischemia. Pacemaker channel blockade with the compound ZD 7288 has been shown to reduce infarct size during myocardial ischemia (Schlack et al., 1998).

The BCNG-1 channel isoforms will be useful as a screen for drugs that alter pancreatic function, including compounds that stimulate or inhibit insulin release. It was demonstrated that the human BCNG-1 protein is expressed in pancreas (Santoro et al., 1998).

The BCNG channel isoforms will be useful to screen drugs that alter function of kidney and liver. BCNG isoforms are expressed in these tissues where they could contribute to hormone release and ion transport functions. Cyclic nucleotide (cGMP)-stimulated activity of a 1 pS channel, similar to the conductance of the pacemaker channel, has been reported for renal epithelial cells (Marunada et al, 1991). Liver cells have been shown to exhibit cation permeable channels coupled to cellular metabolism (Lidofsky et al. 1997).

This invention is illustrated in the Experimental Details section which follows. These sections are set forth to aid in an understanding of the invention but are not intended to, and should not be construed to, limit in any way the invention as set forth in the claims which follow thereafter.

Experimental Details

EXAMPLE 1

Interactive cloning with the SH3 domain of N-src identifies a new brain-specific ion channel protein, with homology to cyclic nucleotide-gated channels By screening for molecules that interact with the neuronal form of Src tyrosine kinase a novel cDNA was isolated that appears to represent a new class of ion channels. The encoded polypeptide, mBCNG-1, is distantly related to proteins in the family of the cyclic nucleotide-gated channels and the voltage-gated channels, Eag and H-erg. mBCNG-1 is expressed exclusively in the brain as a glycosylated protein of approximately 132 kD. Immunohistochemical analysis indicates that mBCNG-1 is preferentially expressed in specific subsets of neurons in the neocortex, hippocampus and cerebellum, in particular pyramidal neurons and basket cells. Within individual neurons, the mBCNG-1 protein is localized to either the dendrites or the axon terminals depending on the cell type.

Southern blot analysis shows that several other BCNG-related sequences are present in the mouse genome, indicating the emergence of an entirely new subfamily of ion channel coding genes. These findings suggest the existence of a novel class of ion channel, which is potentially able to modulate membrane excitability in the brain and which may respond to regulation by cyclic nucleotides.

Defining signal transduction pathways that contribute to the control of synaptic strength in the brain is an important and long-sought goal. In an effort to identify the biochemical targets of Src-family tyrosine kinases in the central nervous system, the yeast two- hybrid system was used to clone proteins that could interact with the SH3 domain of the neural specific form of Src kinase (Brugge, et al., 1985; Martinez, et al., 1987). As a result of this screening a new protein, mBCNG-1 (mouse Brain Cyclic Nucleotide Gated-1) was identified and isolated.

mBCNG-1 has been identified and characterized as an ion channel protein and exhibits sequence homology to voltage-gated potassium channels, CNG channels, and plant inward rectifers. Southern blot analysis suggests that this is the first member of a new family of proteins. mBCNG-1 is expressed exclusively in the brain and is preferentially localized to the processes of subsets of neurons in the neocortex, cerebellar cortex and hippocampus. The specific localization pattern of mBCNG-1 and the potential for a direct interaction with cyclic nucleotides suggest that it may represent a new brain-specific ion channel protein that is an important component in the expression of intercellular and intracellular signaling.

Results

Isolation of mBCNG-1. mBCNG-1, a novel cDNA with homology to CNG-related and Eag-related ion channels was initially isolated and identified by interactive cloning with the N-src SH3 domain in a yeast two-hybrid screen. The src gene expresses an alternatively spliced form (N-src or $pp60^{src-c}(^+)$, which is specific for neuronal cells and has an increased kinase activity (Brugge, et al., 1985). The N-src protein differs from the non-neuronal form (c-src or $pp60^{src-c}$) by an insertion of six amino acids in the region corresponding to the Src homology 3 (SH3) domain of the protein (Martinez et al. 1987). SH3 domains are considered modules for protein—protein interaction (Pawson, et al., 1995). Therefore the yeast two-hybrid screen (Fields, et al., 1989; Zervos, et al., 1993) was used to identify brain specific proteins that would selectively interact with the N-src SH3 domain.

The screening of $5\times10^5$ independent clones with the N-src SH3 bait resulted in the isolation of a single positively reacting fusion product (pJG-d5). This clone encoded a protein that showed a strong interaction with the N-src SH3 domain, but no significant interaction with the c-src, fyn, or abl SH3 domains, indicating a specific recognition of the N-src SH3 domain in the yeast two-hybrid system. The sequence analysis of pJG-d5 indicated that it encodes the C-terminal portion of a larger protein. Overlapping cDNA clones were therefore isolated from a $\lambda$gt10 library and an open reading frame (ORF) was identified that encodes a 910 amino acid polypeptide with a predicted molecular weight of 104 kDa (FIG. 1A). The pJG-d5 insert corresponds to its C-terminal amino acids 404–910.

Figure 1C:
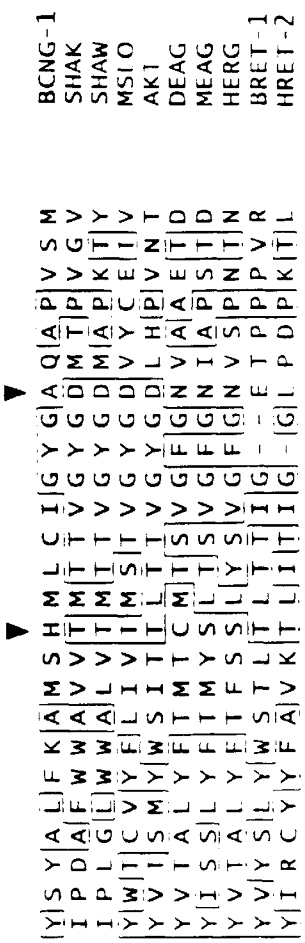
Figure 1D:
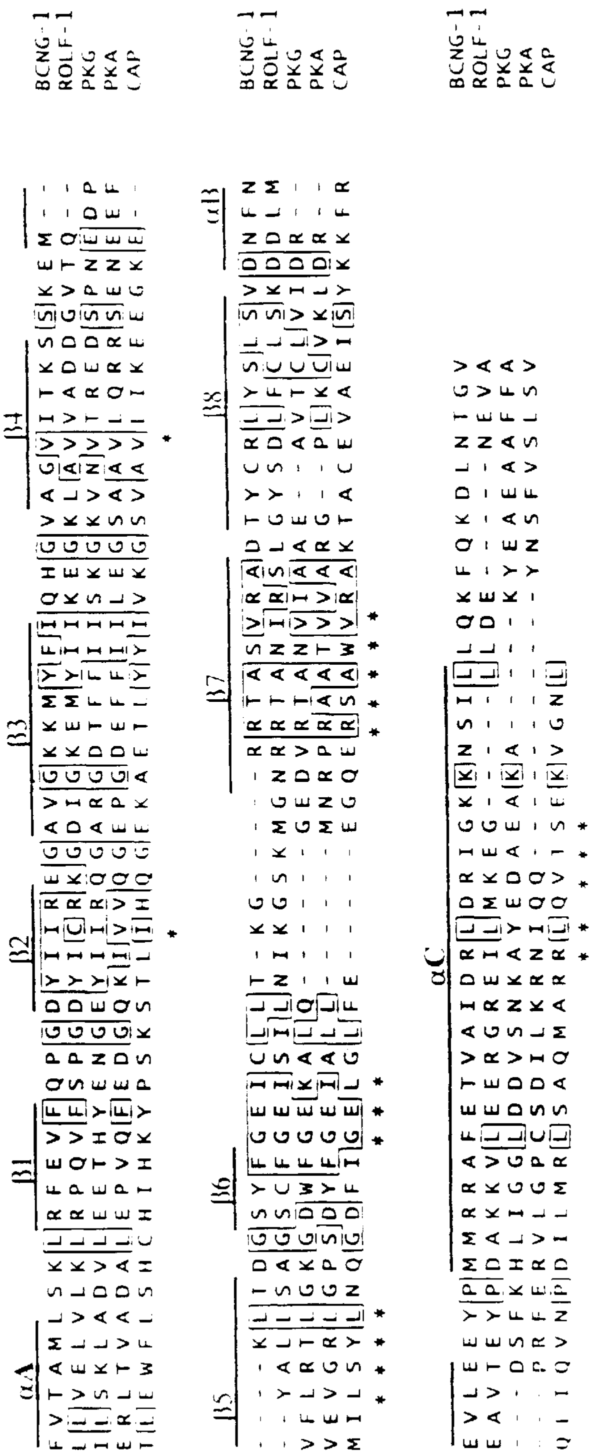

The N-terminal part of the predicted protein contains an hydrophobic core comprising seven hydrophobic domains (FIG. 1B). These domains show significant homology to the six transmembrane domains (S1–S6) and the pore region (P) of voltage activated $K^+$ channels (FIG. 1C). In addition to the hydrophobic core, there is a putative cyclic nucleotide binding site (CNBs) in the C-terminal half of the protein (amino acids 472–602, FIG. 1A and FIG. 1D). This cyclic nucleotide binding site is most closely related to the corresponding region in cyclic-nucleotide gated channels (30% similarity). The amino acids that lie close to the bound cyclic nucleotide in the bacterial catabolite gene activator protein (CAP) are conserved in the N-src interacting protein, suggesting that the CNBs is functional (Weber et al., 1989). On the basis of these features, the newly identified protein was designated mBCNG-1 (mouse Brain Cyclic Nucleotide Gated-1).

Among all the known $K^+$ channel superfamily genes, the core region of mBCNG-1 displays the highest amino acid similarity (22%) to the corresponding region in the mouse Eag protein, whereas the sequence similarity to cyclic nucleotide-gated channels is only 17% in this region (distances were determined by the MegAlign program of DNASTAR). The S4 domain of mBCNG-1 has a total of eight positively charged residues (two groups of four, separated by a serine), which again makes it more similar to voltage activated $K^+$ channels (Sh and eag families) than to cyclic nucleotide-gated channels.

The putative pore forming region of the mBCNG-1 protein (FIG. 1C) is also most closely related to the corresponding region in Shaker and Eag-related channels (30% sequence similarity in either case). However, it contains significant substitutions in two positions that are otherwise highly conserved in voltage activated $K^+$channels: the aspartate residue which follows the GYG triplet is replaced with alanine (position 352) and the serine/threonine residue at −8 from that position is replaced with histidine (position 344). Similar substitutions are found in the β-subunit of the retinal CNG-channel, where the position corresponding to the aspartate is occupied by a leucine and a lysine is found at −8 from that position (Chen, et al., 1993). This suggested that the mBCNG-1 protein might be incapable of conducting current per se, but may act in combination with a second not yet identified polypeptide to form a functional heteromultimeric ion channel.

mBCNG-1 is a 132 kDa Glycoprotein. To characterize the protein encoded by the mBCNG-1 cDNA (ATCC Designation No. 209781) (Seq.ID.No.: 1), antibodies were generated against two separate domains in the predicted cytoplasmic tail: amino acids 594–720 (fusion protein GST-q1; antiserum αq1) and amino acids 777–910 (fusion protein GST-q2; antiserum αq2). Both antisera specifically immunoprecipitated the in vitro translation product of the cloned mBCNG-1 sequence.

Figure 2A:
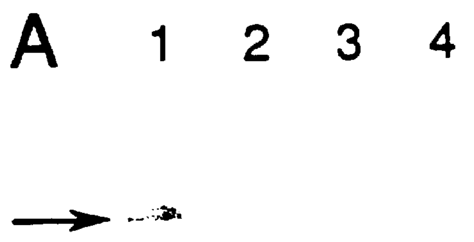
FIGS. 2A–2D. mBCNG-1 is a 132 kDa glycosylated protein.
Figure 2B:
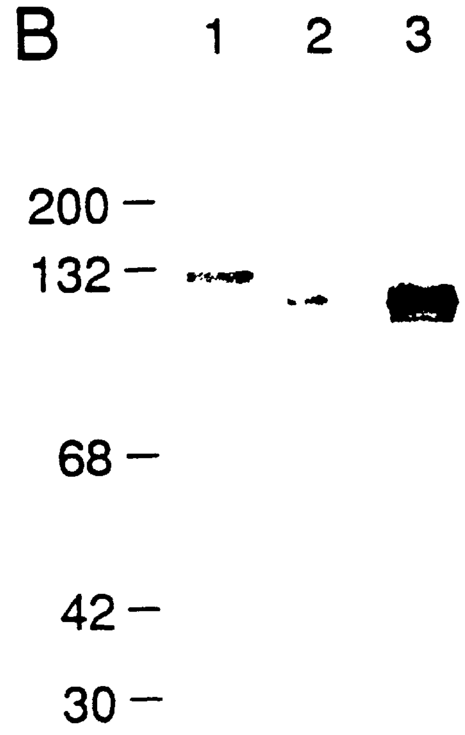
Figure 2D:
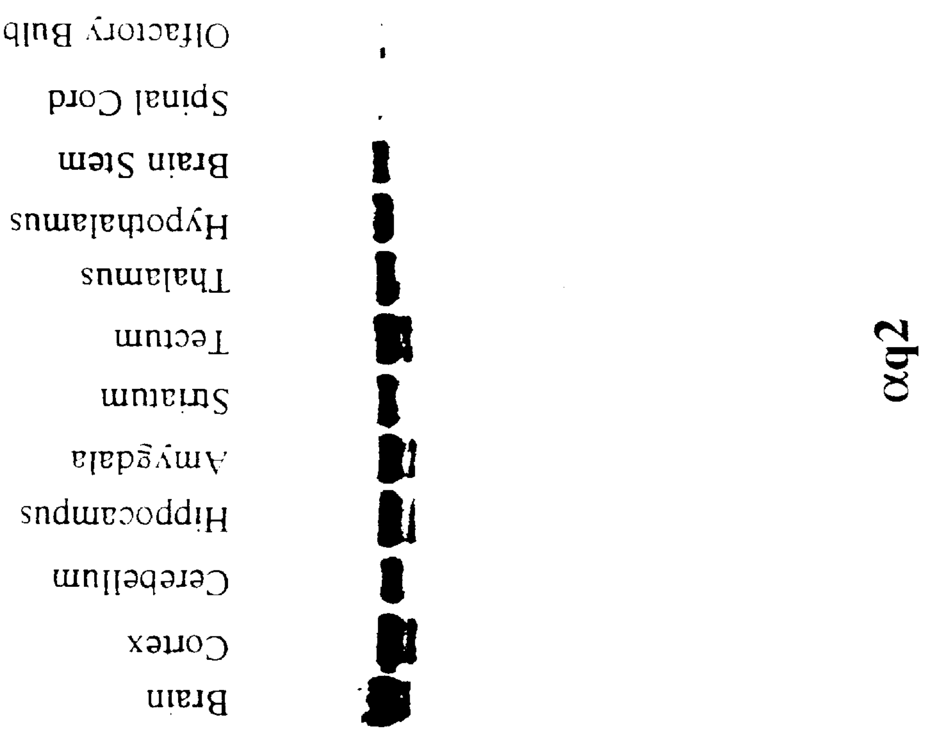
Figure 2C:
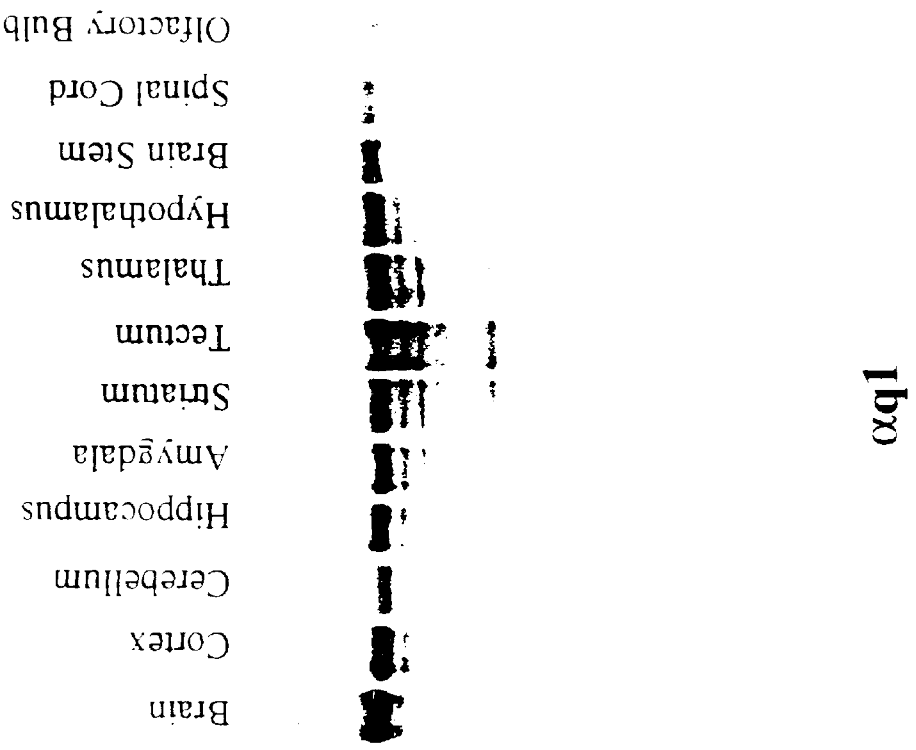

In Western blots of mouse brain extracts, both the αq1 and αq2 antisera recognized a diffuse band with an apparent molecular mass of 132 kDa (FIG. 2A). Complete abolition of the labeling by preadsorbing the antisera with a GST-fusion protein incorporating both antigenic domains (GST-d5, amino acids 404–910) indicates it represents the native mBCNG-1 subunit. Treatment of the brain extract with N-glycosidase F prior to the Western blotting results in a substantial reduction of the molecular weight of the observed band, which now co-migrates with the in vitro translated BCNG-1 product (FIG. 2B).

Figure 3:
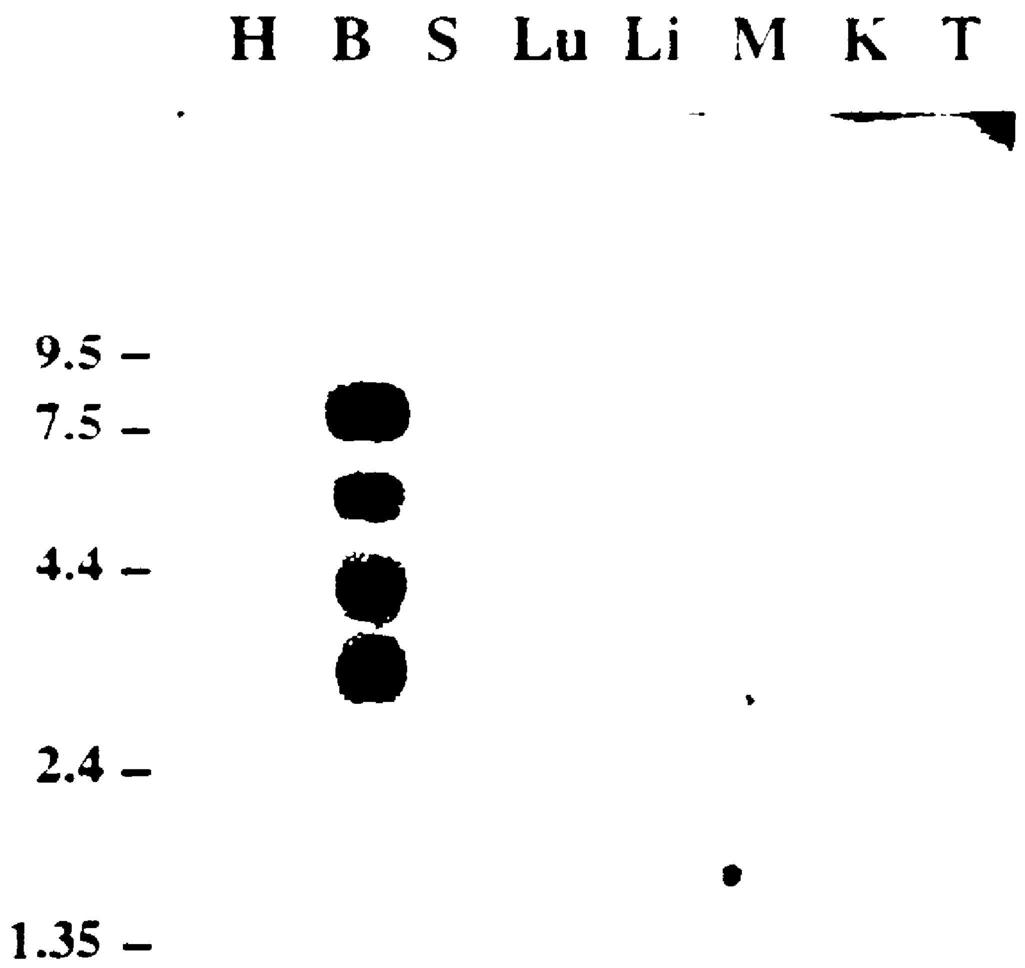
FIG. 3. Northern blot analysis of mBCNG-1 expression in different mouse tissues. Two μg of poly(A)$^+$ RNA from each of each of the following tissues was used: heart (H), brain (B), spleen (S), lung (Lu), liver (Li), skeletal muscle (M), kidney (K) and testis (T) were loaded. The filter was probed with a DNA fragment encoding amino acids 6–131 of the mBCNG-1 sequence. A probe corresponding to amino acids 594–720 recognized the same bands, confirming that the cDNA fragments isolated from the λgt10 and pJG4–5 libraries are from a contiguous mRNA sequence. Positions of molecular weight standards are shown on the left.

Sequence analysis indicates that three N-glycosylation consensus sites are present in the mBCNG-1 protein. Among these, Asn 327 is predicted to lie between transmembrane domain S5 and the pore (P) on the extracellular side of the plasma membrane (FIG. 1A and FIG. 1B). This site corresponds to Asn 327 of the cGMP-gated channel from bovine rod photoreceptors, where it has been demonstrated to be the sole site of glycosylation (Wohlfart et al., 1992). Together, these data suggested that the cloned cDNA sequence encodes the full length product of the mBCNG-1 gene and that mBCNG-1 is a N-linked glycoprotein.

mBCNG-1 is expressed in neurons. Northern blot analysis revealed the presence of multiple mBCNG-1 transcripts in poly$(A)^+$ RNA from the brain, the most abundant species being 3.4, 4.4, 5.8 and 8.2 kb long (FIG. 3). The 3.4 kb transcript corresponds in size to the cloned cDNA. No expression was detected in the heart, spleen, lung, liver, skeletal muscle, kidney or testis. The specific expression of the mBCNG-1 protein was confirmed by Western blot analysis.

The cellular localization of mBCNG-1 within the brain was examined by in situ hybridization (FIG. 4) and by immunohistochemical staining (FIGS. 5A–5F). In both cases, the highest levels of mBCNG-1 expression were detected in the cerebral cortex, in the hippocampus, and in the cerebellum.

Figure 4:
FIG. 4. In situ hybridization analysis of mBCNG-1 expression in the brain. Parasagittal section of a mouse brain probed with an antisense oligonucleotide directed to the mRNA region corresponding to amino acids 648–657 of the mBCNG-1 sequence. Abbreviations: nCtx, neocortex; Hp, hippocampus; Crb, cerebellum; BrSt, brainstem.
Figure 5A:
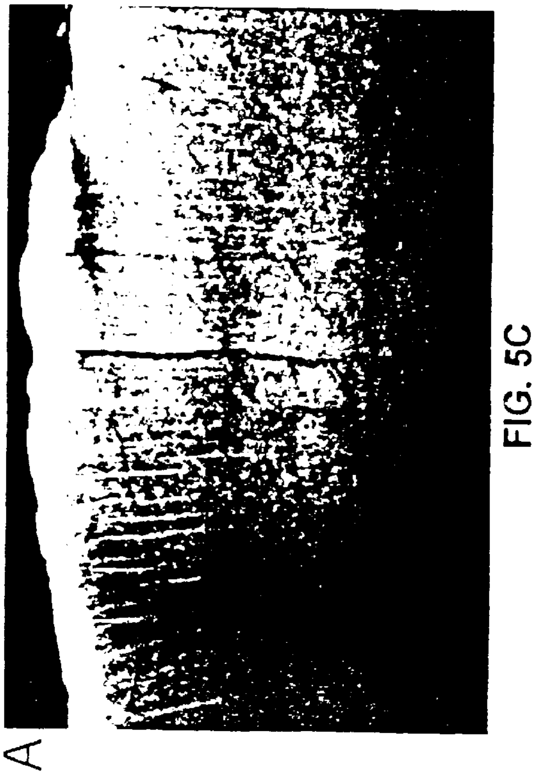
FIGS. 5A–5F: Immunohistochemical analysis of mBCNG-1 expression in the brain. Parasagittal sections of a mouse brain were stained with αq1 and αq2 antisera. The patterns of mBCNG-1 expression detected with the two different antisera were identical, and in both cases the staining was entirely abolished by preadsorbing the sera with the GST-d5 fusion protein. mBCNG-1 immunoreactivity in the cerebral cortex.
Figure 5B:
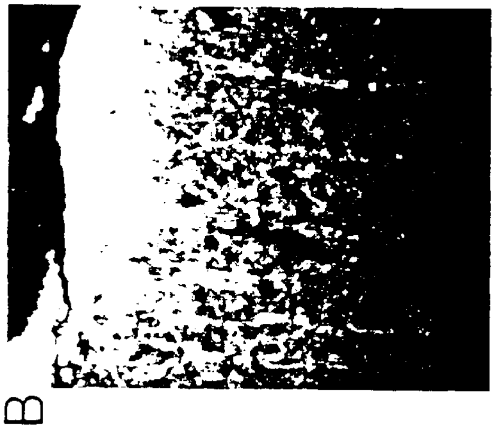

In the cerebral cortex, in situ hybridization shows a strong expression of the mBCNG-1 mRNA layer V pyramidal neuron cell bodies that are distributed in a continuous line along the neocortex (FIG. 4). Immunohistochemical analysis reveals a strict subcellular localization of the mBCNG-1 protein within these cells. Staining of the apical dendrites (FIG. 5A) extends into the terminal branches of these fibers and is particularly intense in layer I, which contains the terminal dendritic plexus of the pyramidal neurons (FIG. 5B).

Figure 5C:
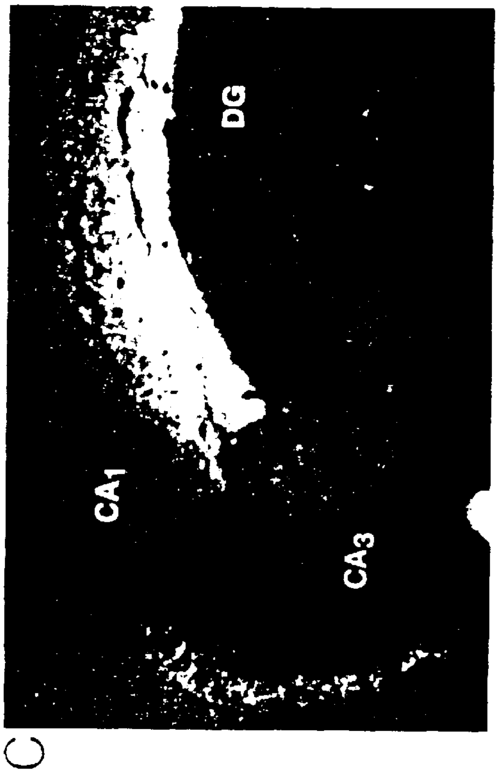
Figure 5D:
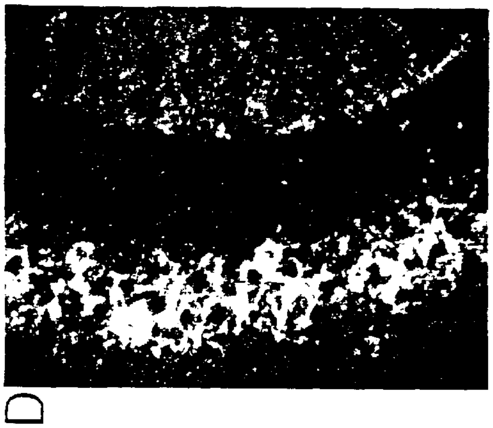

A similar expression pattern can be recognized in the hippocampus. Here, the in situ hybridization shows a strong mBCNG-1 mRNA expression in the pyramidal cell body layer of areas CA1 and CA3 (FIG. 4). The labeling in area CA3 is somewhat less prominent than the labeling in area CA1. At the protein level, the most intense mBCNG-1 immunostaining is observed along the hippocampal fissure, in the layer corresponding to the *Stratum lacunosum-moleculare* (FIG. 5C). This layer contains the terminal branches of the apical dendrites of the pyramidal neurons in area CA1 (Raisman, 1965). Further mBCNG-1 immunoreactivity is detected within the *Stratum pyramidale* of areas CA1 and CA3; the staining, however, is absent from the pyramidal cell bodies but is rather present in the fibers surrounding them (FIG. 5D). These fibers most likely represent the basket cell plexus associated to pyramidal neurons.

Figure 5F:
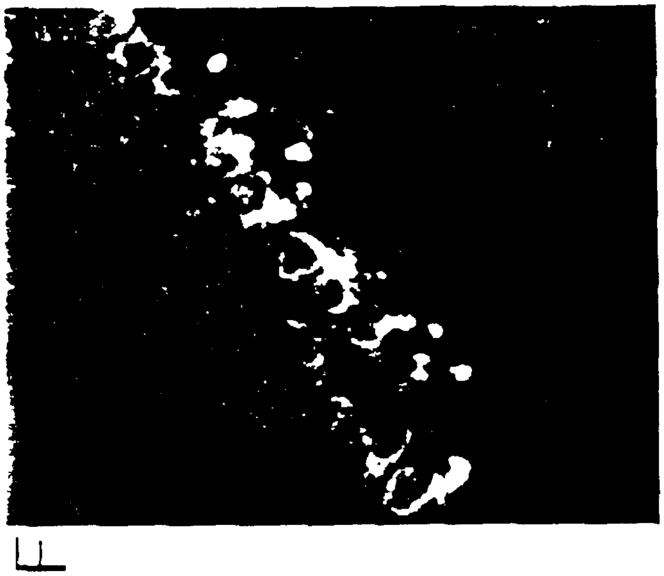
Figure 5E:
Figure 6B:
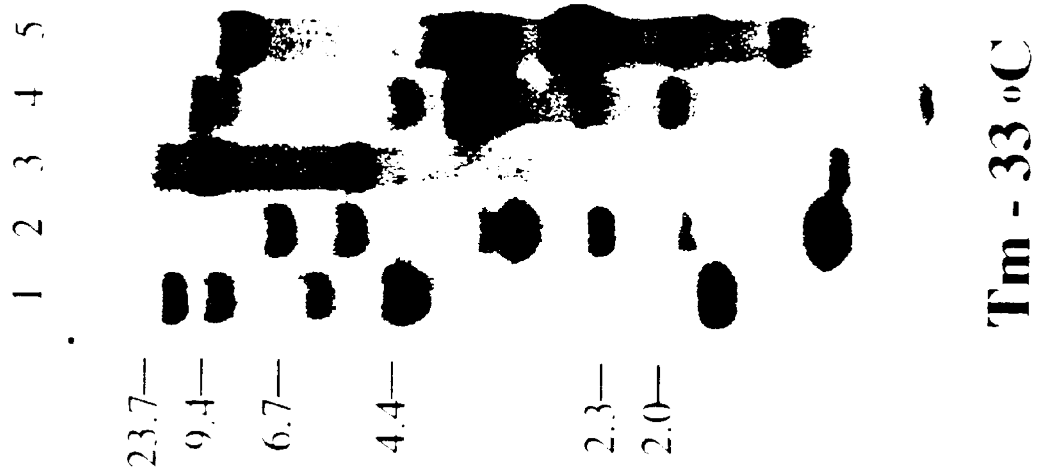
FIGS. 6A–6B. Southern blot analysis of mouse genomic DNA. 4 μg of mouse genomic DNA were loaded onto each lane following digested with Eco RI (1), Hind III (2), Bam HI (3), Pst I (4) or Bgl II (5). The filter was probed with a DNA fragment encoding amino acids 269–462 of the BCNG-1 sequence at high (FIG. 6A) and (FIG. 6B) low stringency. Positions of molecular weight standards are shown on the left.
Figure 6A:

The immunostaining in the cerebellum also shows a pattern characteristic of basket cell expression. In the cerebellar cortex, basket cell nerve endings branch and contact the initial segment of the Purkinje cell axon in a distinct structure known as "pinceau" (Palay, et al., 1974). As shown in FIGS. 5E and 5F, these structures are intensely labeled by the αq1 and αq2 antisera, while the staining excludes the Purkinje cell bodies. Thus, in basket cells, the mBCNG-1 protein appears to be selectively localized to axons and is particularly enriched in the nerve terminals. An intense labeling of some brainstem nuclei is observed by in situ hybridization (FIG. 4) and areas of immunoreactivity were detected in other brain regions, including the olfactory bulb.

mBCNG-1 defines a new subfamily of $K^+$ channel genes. Most of the ion channel sequences characterized so far are members of evolutionarily related multigene families. To investigate whether more sequences related to mBCNG-1 exist, mouse genomic DNA Southern blots were analyzed under various stringency conditions (FIG. 6).

The probe (B1-T) was designed in the hydrophobic core region of mBCNG-1, including transmembrane domains S5, P and S6; the repeat region in the C-terminal portion of the protein was excluded. Reducing the stringency of the hybridization conditions from 80° C. below the melting temperature of the B1-T probe (FIG. 6A) to 33° C. below the melting temperature (FIG. 6B) resulted in the detection of a number of additional hybridization signals in every lane of the blot. None of the known sequences in the $K^+$ channel superfamily has sufficient homology to mBCNG-1 to hybridize under these conditions. This result suggested that mBCNG-1 is the first known member of a larger group of related genes, which represent a new branch in the voltage-gated $K^+$ channel superfamily.

Discussion

Voltage-gated potassium (VGK) channels constitute a large and still expanding superfamily of related genes (Strong, et al., 1993; Warmke and Gonetzky, 1994). The most widely used strategy for cloning new genes in the VGK family has been by homology to a small number of initial members (Sh, eag, and slo from Drosophila (Papazian, et al., 1987; Kamb, et al., 1987; Warmke, et al., 1991; Atkinson, et al., 1991); cGMP-channel from bovine retina (Kaupp, et al., 1989). Unfortunately, this approach is not well suited for identifying more divergent sequences. Expression cloning in *Xenopus* ocytes can circumvent this problem, however, this implies a pre-existing or readily detectable physiological characterization of the channel.

An alternative cloning strategy that requires no a priori knowledge of the structure or activity of the target protein is to screen for $K^+$ channels by means of protein—protein interactions. Using the SH3 domain of N-src as a bait, a protein, mBCNG-1, was obtained that appears to constitute a new branch of the $K^+$ channel superfamily. mBCNG-1 displays the motifs of a voltage-gated $K^+$ channel (six transmembrane spanning domains, a highly basic S4, and a P region) (Strong, et al., 1993, Warmke, et al., 1994 and FIGS. 1A–1D). mBCNG-1, despite its similarity to voltage activated $K^+$ channel superfamily members, with defined by the presence of six transmembrane domains and a pore-like region (Warmke, et al., 1994), shows considerable divergence from all of the other known sequences. Although the cyclic nucleotide binding site of mBCNG-1 is most similar to the site present in CNG channels (30%), the S4 and previous are most closely related to the corresponding regions in Shaker and Eag. Overall, the highest similarity in the hydrophobic core region is to mouse Eag Protein (22%). Thus, mBCNG-1 appears to constitute a new branch of the $K^+$ channel superfamily.

The fusion between an ancestral $K^+$ channel and an ancestral cyclic nucleotide binding site is likely to have occurred prior to the evolutionary separation between plants and animals (Warmke, et al., 1994). Divergence from this common ancestor would have led on one hand to Eag-related channels and plant inward rectifiers (which maintained more of the features of voltage activated $K^+$ channels, while showing a progressive deviation from the original CNBs sequence) and on the other hand to CNG-channels (which show a higher evolutionary constraint on the cyclic nucleotide binding site, while they have lost voltage activation and $K^+$ selectivity). The features of mBCNG-1 suggest that it may have remained closer to the ancestral molecule that represents the evolutionary link between voltage-gated $K^+$ channels and cyclic nucleotide-gated channels.

The emerging pattern for olfactory and retinal CNG-channels and the non-consensus sequence of the putative pore forming region of mBCNG-1 suggests that the lack of detectable electric current following mBCNG-1 expression in xenopus oocytes is due to mBCNG-1 representing a β subunit of a heteromultimeric channel (Chen, et al., 1993; Liman, et al., 1994; Bradley, et al., 1994). Indeed the data show the existence of a number of BCNG-related sequences in the mouse genome, and one or more of these genes could encode additional subunits required for the formation of an active channel.

mBCNG-1 protein is expressed only in the brain and in particular in two of the principal classes of neurons within the cerebral, hippocampal and cerebellar cortexes: pyramidal neurons and basket cells. This distribution would be consistent with an in vivo interaction of mBCNG-1 with N-src, which is also expressed in cerebral and hippocampal pyramidal neurons (Sugrue, et al., 1990). The observed interaction between mBCNG-1 and the N-src SH3 domain is intriguing as is its physiological relevance and the role of the proline-rich region. The possibility that other factors may target the proline-rich region of mBCNG-1 has also to be considered, particularly in view of the recently discovered WW domains (Sudol, et al., 1996; Staub, et al., 1996).

The varied subcellular localization of mBCNG-1 (dendritic in pyramidal cells and axonal in basket cells) suggests that mBCNG-1 could play different roles in different populations of neurons, perhaps by regulating presynaptic or postsynaptic membrane excitability depending on the cell type. A similar distribution has been demonstrated for the $K^+$ channel subunit Kv 1.2 (Sheng, et al., 1994; Wang, et al., 1994). Kv 1.2 forms heteromultimeric $K^+$ channels with several other Shaker type subunits, which have an overlapping yet differential pattern of expression, giving rise to a range of conductances with diversified functional characteristics.

The presence of mBCNG-1 in the dendrites of hippocampal pyramidal cells is particularly intriguing; cAMP has been shown to be important for the establishment of some forms of long-term synaptic potentiation in these cells (Frey, et al., 1993, Bolshakov, et al., 1997; Thomas, et al., 1996). The structural features of mBCNG-1 predict a $K^+$ conducting activity, directly modulated by cyclic nucleotide binding. Interestingly, a current with similar characteristics has been described in the hippocampal pyramidal neurons of area CA. (Pedarzani, et al., 1995), where mBCNG-1 is highly expressed. This current ($I_Q$) is believed to contribute to the noradrenergic modulation of hippocampal activity, by regulating neuronal excitability in response to cAMP levels. mBCNG-1 could participate in the formation of the channels responsible for this type of current.

Experimental Procedures

Yeast two hybrid interaction cloning of mBCNG-1. The two-hybrid screen was performed following published procedures (Zervos, et al., 1993); the reagents used included plasmids pEG202, pJG4–5, pJK103 and *Saccharomyces*

*cerevisiae* strain EGY48 (MATa trp1 ura3 his3 LEU2::pLexAop6-LEU2).

The bait was created by subcloning the SH3 domain of N-src in plasmid pEG202, and contains amino acids 83–147 from the mouse N-src sequence (Martinez, et al., 1987). The cDNA fusion library was constructed in plasmid pJG4–5, using poly(A)$^+$ RNA from the whole brain of an adult C57BL/6 male mouse; the cDNA was synthesized using random hexamers and the GIBCO-BRL SuperScript II synthesis kit, according to the manufacturer's instructions. Only the library constructed from the two fractions with an average cDNA size of >1.5 kb (total of $1\times10^6$ independent clones) was used in the two hybrid screen. Library amplification was done in 0.3% SeaPrep agarose (FMC) to avoid changes in complexity.

For library screening, *Saccharomyces cerevisiae* strain EGY48 was first cotransformed with the bait plasmid pEG202-Nsrc and the reporter plasmid pJK103. The resulting strain was maintained under selection for the HIS3 and URA3 markers, and subsequently transformed with the mouse brain cDNA library in plasmid pJG4–5. This description though is more accurate and should be substituted for the transformation mix was grown for two days in a Ura$^-$ His$^-$ Tr$^-$-glucose medium containing 0.3% SeaPrep agarose (FMC); the cells were then harvested and plated on Ura$^-$ His$^-$ Trp$^-$ Leu$^-$-galactose. Leu$^+$ colonies were screened for β-galactosidase activity using a filter lift assay (Breede and Nasmith, 1985). Positively reacting fusion products were isolated and tested for specificity following retransformation into an independent yeast strain. Fusion product pJGd5 corresponds to the C-terminal part of mBCNG-1 (amino acids 404–910; see FIG. 8).

Full length cloning of mBCNG-1. For the isolation of the 5' end region of the mBCNG-1 cDNA, two rounds of PCR were performed on the pJG4–5 library, using nested oligonucleotides derived from the pJG-d5 sequence. The downstream primer in the first round was: 5'-AGAGGCATAGTAGCCACCAGTTTCC-3' (Seq. ID. No.: 13)(d5.RL, corresponding to amino acids 456–463 of the mBCNG-1 sequence; see FIG. 8). The downstream primer in the second round was: 5'-CCGCTCGAGGCCTTGGTATCGGTGCTCATAG-3' (Seq. ID. No.: 2) (d5.N2), corresponding to amino acids 424–430 of mBCNG-1 and an added XhoI site). The upstream primer was either of two oligonucleotides designed in the pJG4–5 vector sequence: 5'-GAAGCGGATGTTAACGATACCAGCC-3' (Seq. ID. No.: 3) (B42), located 5' to the EcoRI site in the B42 acidic patch, or: 5'-GACAAGCCGACAACCTTGATTGGAG-3' (Seq. ID. No.: 4) (ter), located 3' to the EcoRI site in the ADH terminator.

PCR cycling was performed as follows: 1x(2 minutes, 94° C.); 25x(45 seconds, 94° C.; 30 seconds, 58° C.; 3 minutes, 72° C.); 1x(10 minutes, 72° C.).

The longest amplification product obtained from this series of reactions was a 700 bp DNA fragment, which contained amino acids 204–430 from the mBCNG-1 sequence (See FIG. 8). This fragment was subcloned, repurified and used as a probe to screen a Mouse Brain cDNA library in λgt10 (CLONTECH, cat. no. ML3000a), in high stringency conditions (hybridization overnight at 65° C. in 50% formamide, 5x SSC (1x SSC=0.15 M sodium chloride/0.015 sodium citrate, pH 7), 5x Denhardt's (1x Denhardt's =0.02% Ficoll/0.02% polyvinylpirrolidone/0.02% bovine serum albumin), 0.5% SDS, 100 mg/ml salmon sperm DNA. Washing: 10 minutes, room temperature in 2x SSC/0.1% SDS, followed by twice 30 min at 65° C. in 0.2x SSC/0.1% SDS.

Positively reacting clones were further screened by PCR, using oligonucleotide d5.RL (Seq. ID. No.: 13) as a downstream primer. The upstream primer was either of the two following vector oligonucleotides: 5'-GAGCAAGTTCAGCCTGGTTAAGTCC-3'(Seq. ID. No.: 5) (15'.N2), located 5' to the EcoRI site in the λgt10 sequence, or 5'-GTGGCTTATGAGTATTTCTTCCAGGG-3' (Seq. ID. No.: 6) (13'.N2), located 3' to the EcoRI site. PCR cycling was performed as described above.

The resulting products were subcloned and sequenced. The longest extension contained amino acids 1–463 of the mBCNG-1 sequence (See FIG. 8); the overlapping region of this insert with the insert contained in clone pJG-d5 (amino acids 405–463) includes a Bgl II site, which was used to join the 5' and 3' fragments of the mBCNG-1 cDNA in plasmid pSD64TF for expression studies.

In vitro transcription (MESSAGE MACHINE, Ambion, Austin, Tex.) and translation in vitro Express, Stratagene.

Northern/Southern Blot Hybridization

PCR-generated cDNA fragments corresponding to the indicated amino acids 6–131 (λgt10-derived) 5' sequence) and 594–720 (pJG-5 derived 31 sequence) were used to probe a Multiple Tissue Northern Blot (CLONTECH, 7762-1).

For Southern blots, a Mouse Geno-Blot (CLONTECH, 7650-1) was probed using a PCR generated cDNA fragment (B1-T) corresponding to amino acids 270–463 of the mBCNG-1 sequence, as described (Sambrook, 1989). Blots were hybridized at 65° (5x standard saline citrate 1xSSC=0.15M sodium chloride/0.015 M sodium citrate, pH7 buffer in aqueous solution) and washed as described in figure legends. Washings conditions were as indicated. The melting temperature (TM) for the B1-T probe was calculated according to the formula Tm=81.5° C.+16.6 (logM)+0.41 (% GC)−(675/L), where M is the cation concentration and L is the probe length in base pairs.

Antibody production extracts and Immunochemistry and in situ hybridization. The Glutathione S-transferase (GST)-fusion proteins were created by subcloning the q1 (corresponding to amino acids 594–720 of the mBCNG-1 protein) or q2 (corresponding to amino acids 777–910 of the mBCNG-1 protein) (see FIG. 1A) in plasmid pGEX-lombole (Pharmacia), followed by induction and purification of essentially as described (Frangioni and Neel, 1993). Fusion proteins were eluted in phosphate buffered saline (PBS) and injected into rabbits as a 1:1 suspension with Freund adjuvant (Pierce). Antisera were prepared and tested essentially as described (Grant, et al., 1995).

For Western Blot analysis, mouse brain extracts were separated on a 10% SDS-PAGE and electroblotted to PVDF membranes (Immobilon-P, Millipore) as described (Grant, 1995). Blocking and antibody incubations were done in TBST (10 mM Tris pH 7.5, 150 mM NaCl, 0.1% Tween-20)+2% BSA. The αq1 and αq2 antisera were used at a 1:1000 dilution. Secondary anti-rabbit antibodies coupled to alkaline phosphatase (Bio-Rad) were used at a 1:5000 dilution, and the bands were visualized by incubation in NBT/BCIP (Boehringer Mannheim). Total brain extracts were prepared as described (Grant, 1995). For N-glycosidase treatment, 2% SDS was added to the extract and the proteins denatured by boiling for 10 min; reactions were carried out in 50 mM NaP (pH 7.2), 25 mM EDTA, 0.5% Triton-X100, 0.2% SDS, 1 mg/ml protein and 20 U/ml N-glycosidase F (Boehringer) for 1 hr at 37° C.

For immunohistochemistry, 20 μm cryostat sections of mouse brain (fixed in 4% paraformaldehyde/PBS), quenched in 50 mM $NH_4Cl$/PBS, were blocked (10% goat serum, 0.1% goat serum, 0.1% saponin in PBS) and then exposed to αg1 or αq2 antisera (diluted 1:400 in blocking solution). After washing in PBS+0.1% saponin, sections were incubated with Cy3-conjugated goat anti-rabbit F(ab') 2 fragments (Jackson Immunoreasearch Labs) diluted 1:200 in blocking solution.

In situ hybridization was performed essentially as described (Mayford et al., 1995) using oligonucleotide probes labeled by $3^1$ tailing with using$^{35}$ (S) thio-dATP and terminal transferase (Boehringer Mannheim) to a specific activity of $5\times10^8$ cpm/μg. Hybridizations were carried out at 37° C. Slides were washed at 60° C. in 0.2x SSC and exposed to film for 2 weeks.

EXAMPLE 2

Identification of a Family of BCNG Genes

Introduction

The original sequence in the BCNG family (mBCNG-1) was isolated from a mouse brain cDNA library using yeast two-hybrid interaction cloning with the n-Src tyrosine kinase as a bait as described in Example 1. The DNA and amino acid sequences of this protein are Seq. ID. No.:1 and Seq. ID. No.:2 respectively.

Three additional mouse and two human cDNA clones encoding regions homologous to mBCNG-1 (ATCC Designation No. 209781) were isolated. Partial cDNA clones representing two of the mouse genes ([mBCNG-2 [ATCC Designation Nos. 209825 and 209826] and mBCNG-3 [ATCC Accession Nos. 209824 and 209828]) were isolated while screening for full length mBCNG-1 products, and a fourth mouse gene (mBCNG-4) as well as two human genes (hBCNG-1 [ATCC Designation No. 209827] and hBCNG-2 [ATCC Accession No. 209781]) were identified following an EST database homology search, using the protein sequence of mBCNG-1 (Seq.ID.No.: 2) as a query. Further extensions of the identified cDNA clones were subsequently obtained by library screening or RT-PCR cloning. A schematic representation of the mouse and human BCNG sequences identified is presented in FIGS. 7A- 7B.

The three additional mouse proteins described hereined below are closely related to each other, having a sequence similarity of 84–88%, but are very distantly related to all other known members of the potassium channel superfamily, including Eag-related channels (22% similarity) and cyclic nucleotide-gated channels (17% similarity).

Northern blot analysis showed individual patterns of tissue distribution for each of these clones (see FIG. 9). The expression of mBCNG-1 appears to be restricted to the brain (FIG. 9A), whereas mBCNG-2 (FIG. 9B) and mBCNG-3 (FIG. 9C) are expressed in the brain as well as in the heart. Hybridization signals for mBCNG-3 are also detected in $polyA^+$ RNA from skeletal muscle and lung.

The distinct sequences and tissue distributions of these clones reveals that the BCNG clones represent a family of ion channel proteins, with characteristic voltage sensing and cyclic nucleotide binding motifs, that are predominantly located in heart and brain.

Results

The first fragment of mBCNG-2 (mBCNG2a) was cloned as a product of nested PCR reactions, designed to isolate 5' extensions of mBCNG-1 (Santoro et al., 1997). This fragment appeared to represent a distinct gene product from mBCNG-1 because of sequence differences in the overlapping region of the two PCR products. The differences were mostly third base codon substitutions. This fragment was used to screen a mouse brain XgtlO library; the N-terminal portion of a protein similar to, but distinct from mBCNG-1 was obtained (clone 11-λ1, designated mBCNG-2b). From the same λgt10 library screen, a weakly reacting plaque was also identified, which, upon subcloning and sequencing of the corresponding insert (clone 15-7, designated mBCNG-3a), was shown to represent a third distinct gene of the BCNG family (mBCNG-3). Seq.ID.No.: 5 represents mBCNG-2 DNA sequence while Seq.ID.No.: 6 represents mBCNG-2 amino acid sequence. Seq.ID.No.: 9 represents mBCNG-3 DNA sequence while Seq.ID.No.: 10 represents mBCNG-3 amino acid sequence.

A BLAST search in mouse and human EST databases revealed four EST clones that appear to be fragments of two mouse BCNG genes (M41-EST, M28-EST) and two human BCNG genes (HS7-EST, H61-EST).

The M41-EST sequence appeared to represent the 3' fragment of a BCNG-like gene, overlapping the cyclic nucleotide binding site. An oligonucleotide in this sequence (oligo 41REV [Seq.ID.No.: 24]) and an oligonucleotide in a conserved region of the 5' portion of the BCNG clones (oligo B123 [Seq.ID.No.: 23]), were synthesized and used to obtain RT-PCR products from mouse RNA. Sequencing of the RT-PCR product sections overlapping with the 5' end of the M41-EST clone and with the 3' end of mBCNG-2 cDNA (clone 11-λ1, designated mBCNG-2b) established that M41-EST represents the 3' end region of mBCNG-2.

The M28-EST clone also appeared to contain a fragment of a BCNG-like gene, including the 3' end region of the cyclic nucleotide binding site. A degenerate oligonucleotide based on the M28 sequence was thus designed (oligo 28REV [Seq.ID.No.: 25]) and used together with the B123 oligonucleotide [Seq.ID.No.: 23]in an RT-PCR reaction on mouse RNA. Although the products obtained appear to represent extensions of mBCNG-3, as determined by the overlap with the 3' region of clone 15-7, sequencing reveled a difference in the overlapping region with the M28-EST clone. Thus, M28-EST represents yet another BCNG-like gene, which was designated mBCNG-4. Seq.ID.No.: 11 represents mBCNG-4 DNA sequence while Seq.ID.No.: 12 represents mBCNG-4 amino acid sequence. Complete sequencing of the M28-EST clone revealed that only the 3' end of the clone aligns with the BCNG sequences; the sequence 5' to position 632 is likely to represent an intron, and a stop codon is present at position 869 (see FIG. 1).

Figure 7A:
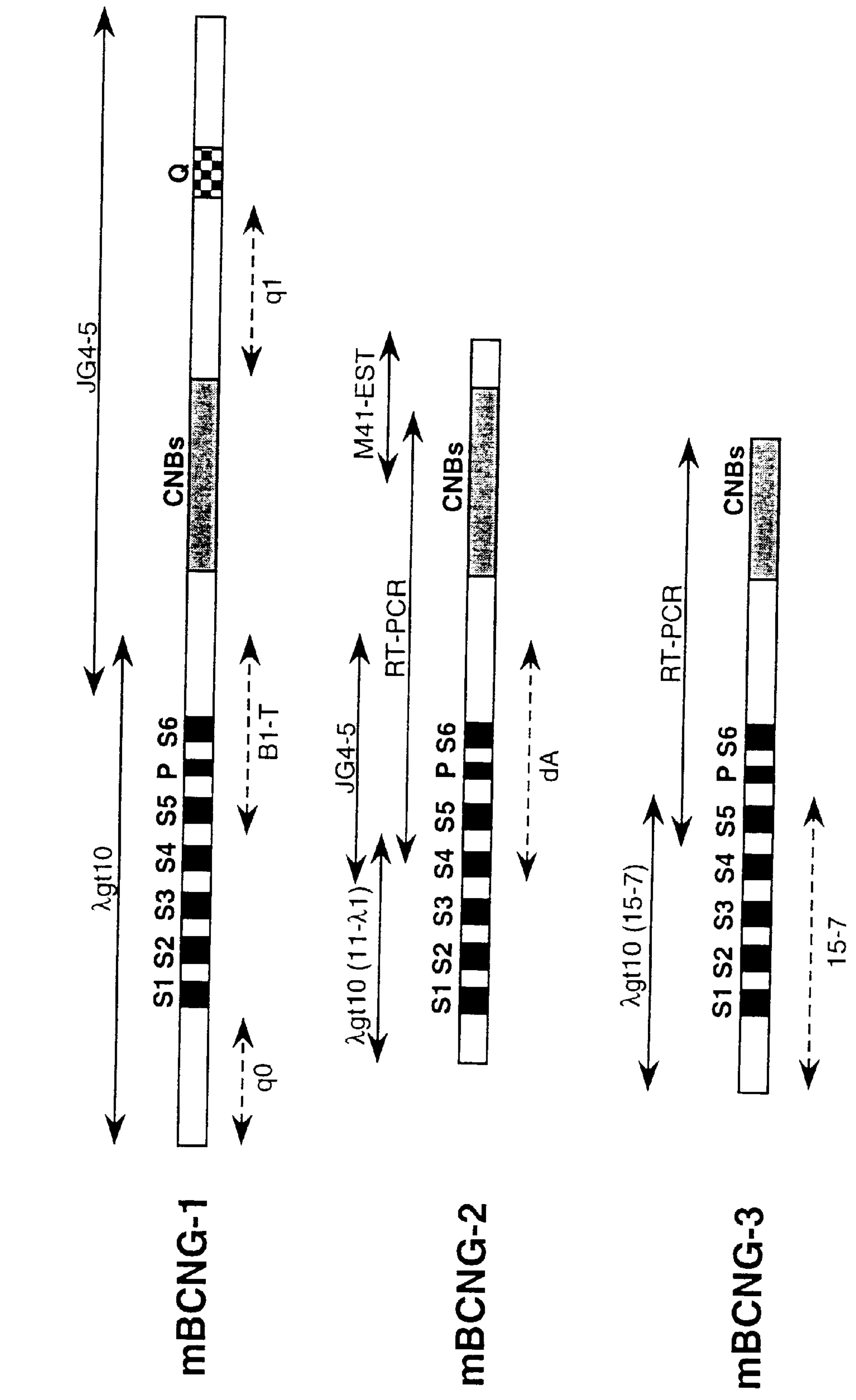
FIGS. 7A–7C. Schematic representation of the mouse and human BCNG clones.
Figures 7B, 7C:
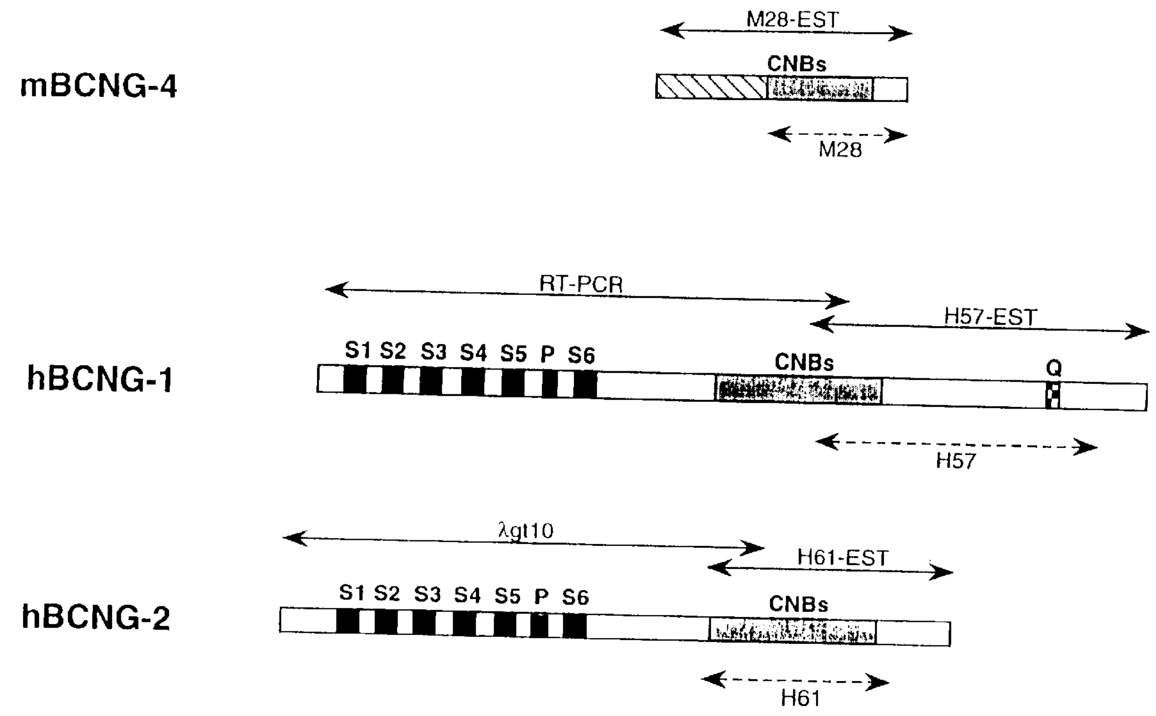

Correspondence between these ESTs and the BCNG gene family is shown schematically in FIGS. 7A–7B and is indicated in Table I. Clones were obtained from the IMAGE consortium. The clones were used in the following way.

TABLE I

EST CLONES IDENTIFIED BY HOMOLOGY TO mBCNG-1

| Trivial Name | Probable Identity | GeneBank Accession number | IMAGE consortium cDNA ID | Genome systems ID |
|---|---|---|---|---|
| M41-EST | 3' of mBCNG-2 | AA023393 | 456380 | |
| M28-EST | 3' of mBCNG-4 | AA238712 | 693959 | cd-22017 |
| H61-EST | 3' of hBCNG-2 | N72770 | 289005 | |
| H57-EST | 3' of hBCNG-1 | H45591 | 176364 | |

Table I lists the trivial names (designated herein), the probable correspondence between these ESTs and the BCNG genes, the GeneBank accession numbers and the clone identification numbers used by the I.M.A.G.E. consortium and Genome systems for these clones.

Predicted Amino Acid Sequence of the Conserved BCNG Channel Family. The deduced, integrated amino acid sequences obtained for the mBCNG-2 (Seq.ID.No.:6), mBCNG-3 (Seq.ID.No.:10) and mBCNG-4 (Seq.ID.No.: 12) encoded proteins are shown in FIGS. 8A–8B, and were aligned to the full length sequence of mBCNG-1 (Seq.ID.No.:2) (Santoro et al., 1997) (GenBank Accession No.: AF028737). All of the identified sequences (except mBCNG-4) contain the motifs of a voltage-gated potassium channel (Jan and Jan, 1997). Thus, they appear to encode for channel subunits with an intracellular amino terminus, six putative transmembrane spanning domains (S1–S6), and a long cytoplasmic carboxy terminus. The S4 domain, which serves as the voltage sensor in other voltage-gated channels, contains 9 positively charged basic residues, more so than any other voltage-gated channel. In addition, the three clones contain a highly conserved pore-forming P region that links the 5S and S6 transmembrane segments. This P loop is homologous to the P regions of voltage-gated K channels and in particular contains the K channel signature sequence triplet, GYG, suggesting that the clones will encode a K selective ion channel (Heginbotham et al., 1994).

The long cytoplasmic tail of the BCNG proteins is predicted to contain a stretch of 120 amino acids that is homologous to the cyclic nucleotide binding (CNB) sites of cAMP- and cGMP-dependent protein kinases and the catabolite activating protein, CAP, a bacterial cAMP binding protein (Shabb and Corbin, 1992). The BCNG cyclic nucleotide-binding domains are most similar to the binding domains of the cyclic nucleotide-gated channels involved in visual and olfactory signal transduction (Zagotta and Siegelbaum, 1996). Although other members of the voltage-gated channel family have been reported to contain CNB sites, these putative sites lack many of the key conserved residues found in functional cyclic nucleotide-binding proteins (Tibbs et al., 1998). Strikingly, these key residues are conserved in the BCNG channel family, suggesting that these binding sites are likely to function.

Certain pacemaker channels can be regulated by PKA phosphorylation, such as the cardiac Purkinje fiber channel (Chang et al., 1991), whereas other pacemaker channels appear to be directly regulated by cAMP, such as the sino-atrial node channel (DiFrancesco and Tortora, 1991). It is interesting that mouse (and human) BCNG-1 and BCNG-2 contain a serine residue in their cytoplasmic carboxy terminus that lies within a consensus site for PKA phosphorylation (FIG. 8B, arrow). mBCNG-4 does not contain this site, providing a potential explanation for the different modulatory properties of channels in different tissues. What is particularly striking about this potential phosphorylation site is that it lies within the C-helix of the cyclic nucleotide binding site, a region that forms a key part of the ligand binding pocket (Weber and Steitz, 1987). Studies on rod and olfactory cyclic nucleotide-gated channels previously showed that the C-helix plays an important role in ligand-selectivity and the efficacy of ligand-gating (Goulding et al., 1994; Varnum et al., 1995). Thus the phosphorylation of this serine residue might influence the efficacy with which cyclic nucleotides modulate the gating of certain pacemaker channels.

The mouse proteins are closely related to each other, having a similarity of 84–86% (FIG. 7C). Notably, mBCNG-2 and mBCNG-3 are more closely related to each other (89% similar) than either is to mBCNG-1. As far as a limited alignment could show (see legend to FIG. 7), mBCNG-4 appears to be the most distantly related protein in the group.

Cloning of Two Human BCNG Genes. The high degree of similarity between H57-EST and mBCNG-1 suggested that this EST likely represented the 3' end region of the human homolog of mBCNG-1 (designated hBCNG-1). Based on this assumption, PCR oligonucleotide primers were synthesized in order to amplify hBCNG-1. (See FIG. 7). One primer consisted of a sequence in the 5' end of the mouse BCNG clones (oligo MB1–3 [Seq.ID.No.: 26]) and the second primer was based on a sequence in the H57-EST (oligo H57.C [Seq.ID.No.: 27]). (See FIG. 7). A single, strong RT-PCR product of the predicted length was obtained using human brain polyA+ RNA. No band was obtained from human heart polyA+ RNA. Upon completion of the sequencing of the original EST clone and of the RT-PCR product, 2247 bp of the hBCNG-1 sequence was obtained (Seq.ID.No.: 3)(see FIG. 7). The predicted amino acid sequence of the encoded hBCNG-1 protein (Seq.ID.No.: 4) is shown in FIG. 8. Remarkably, the 308 amino acid-long core region of the hBCNG-1 protein, extending from the S1 through the S6 transmembrane segments, is 100% similar to mBCNG-1.

The H61-EST sequence showed marked sequence similarity to mBCNG-2 and could, in fact, encode the human homolog of the mBCNG-2 protein. Accordingly, a sequence within the H61-EST clone was used to probe a human brain λt10 cDNA library. (See FIG. 7). Combining the sequences of the H61-EST clone and of the λgt10 clones, 1792 bp of the hBCNG-2 sequence was obtained (Seq.ID.No.: 7) (See FIG. 7). The predicted amino acid sequence of the encoded hBCNG-2 protein is shown in Seq.ID.No.:8. (See FIG. 8). The 308 amino acid-long core region of the hBCNG-2 protein is 98% similar to mBCNG-2 (FIG. 7C).

Tissue Distribution of BCNG mRNA Expression. Northern blot analysis showed individual patterns of tissue distribution for each of the identified clones and a high correspondence in the transcript and localization patterns between homologous mouse and human clones (FIGS. 9 and 10). While the expression of mBCNG-1 appears to be restricted to the brain (FIG. 9, and Santoro et al. 1997), mBCNG-2 and mBCNG-3 are expressed in the brain as well as in the heart (FIG. 9). Hybridization signals for mBCNG-3 are also detected in polyA+ RNA from skeletal muscle and lung. A distinct pattern of tissue distribution is revealed for mBCNG-4, which appears to be mainly expressed in the liver, but is also present in brain, lung and kidney (FIG. 9D).

The homologous mouse and human BCNG genes are likely to be functionally similar since they exhibit very similar patterns of tissue expression as revealed by the Northern blot analysis. FIG. 10 shows that a probe designed within the hBCNG-1 sequence recognized four transcripts in human brain polyA+ RNA. This pattern is very similar to that seen in the Northern blot of mBCNG-1 (FIG. 9 and Santoro et al. 1997). Weak hybridization signals are also detected for hBCNG-1 in human muscle and pancreas. Northern blot analysis using a probe based on the hBCNG-2 sequence showed an expression pattern which is highly consistent with the expression pattern of mBCNG-2 (FIG. 10; compare with FIG. 9). An abundant 3.4 kb transcript is detected in the brain and the same transcript is also present in the heart.

The analysis of the distribution of mBCNG-1 within the mouse brain (Santoro et al. 1997) revealed that the highest expression of mBCNG-1 occurs in the cortex, hippocampus and cerebellum. Moreover, the mBCNG-1 protein is specifically localized to the apical dendrites of pyramidal neurons as well as to the axon terminals of basket cells within these regions. (See, Example 1). Northern blot analysis of the hBCNG-1 MRNA distribution within different brain regions also showed a differential expression of the gene, with the highest levels present in cortical structures (hippocampus and amygdala; FIG. 10). hBCNG-2 shows a more uniform level of high expression in all brain structures, suggesting a more ubiquitous role. In particular, the strong hybridization signal in corpus callosum-derived RNA may indicate expression of hBCNG-2 within glial cells.

Experimental Procedures

Library screening and RT-PCR cloning. Standard manipulations of Escherichia coli, lambda phage and nucleic acids, including recombinant DNA procedures, were performed essentially as described (Sambrook et al. 1989).

Cloning of mBCNG-2. From the nested PCR reactions performed on the pJG4–5 library (see Example 1, Full-length cloning of mBCNG-1) an amplification product was isolated, that had a sequence similar but not identical to the expected mBCNG-1 sequence. It was thus inferred that it represented a different gene, closely related to mBCNG-1, which was designated mBCNG-2. The identified fragment ("dA") encoded amino acids 234–430 from the mBCNG-2 sequence (numbering according to mBCNG-1, see FIG. 8)

Next performed was a series of RT-PCR reactions on polyA$^+$ RNA derived from mouse brain and heart, using oligos: 5'-TGGGAAGAGATATTCCACATGACC-3' (Seq. ID. No.: 7) (7.SEQ1, corresponding to amino acids 270–277 of the mBCNG-1 sequence; see FIG. 8) as an upstream primer, and oligo d5.RL (Seq. ID. No.: 1) as a downstream primer. A 600 bp product was obtained from heart polyA$^+$ RNA, subcloned, sequenced and shown to be identical to mBCNG-2. PCR cycling: 1x (2 minutes, 94° C.); 25x (50 seconds, 94° C.; 40 seconds, 52° C.; 1.5 minute, 72° C.); 1x (10 minutes, 72° C.).

The Clontech Mouse Brain λgt10 library was screened at high stringency (see Example 1, Full-length cloning of mBCNG-1), with a PCR probe derived from the mBCNG-2 sequence (probe "dA") using oligos: 5'-TACGACCTGGCAAGTGCAGTGATGCGC-3' (Seq. ID. No.: 8) (ASEQ2, corresponding to amino acids 278–286 of the mBCNG-2 sequence, numbering according to mBCNG-1; see FIG. 8) as an upstream primer, and 5'-AGTTCACAATCTCCTCACGCAGTGGCCC-3' (Seq. ID. No.: 9) (HRL.2, corresponding to amino acids 444–452 of the mBCNG-2 sequence, numbering according to mBCNG-1; see FIG. 8) as a downstream primer.

Positively reacting clones were further screened by PCR, using oligonucleotide: 5'-CTGGTGGATATATCGGATGAGCCG-3' (Seq. ID. No.: 10) (BE-ASE, corresponding to amino acids 262–269 of the mBCNG-2 sequence, numbering according to mBCNG-1; see FIG. 8) as a downstream primer and either of the two lambda derived oligonucleotides (15'.N2 (Seq. ID. No.: 5) or 13'.N2 (Seq. ID. No.: 6)) as an upstream primer (see Example 1, Full length cloning of mBCNG-1). The clones yielding the longest extension products were subcloned and sequenced, thus obtaining the N-terminal part of the mBCNG-2 sequence up to amino acids 304 (numbering according to mBCNG-1; see FIG. 8).

After obtaining the sequence for EST-M41, a further round of RT-PCR reactions was performed both on mouse brain and heart polyA$^+$ RNA, using oligonucleotides: 5'-CAGTGGGAAGAGATTTTCCACATGACC-3' (Seq. ID. No.: 11) (B123, corresponding to amino acids 269–277 of the BCNG sequences, numbering according to mBCNG-1; see FIG. 8) as an upstream primer, and 5'-GATCATGCTGAACCTTGTGCAGCAAG-3' (Seq. ID. No.: 12) (41REV, corresponding to amino acids 590–598 of the mBCNG-2 sequence, numbering according to mBCNG-1; see FIG. 8) as a downstream primer. Extension products of the expected length were obtained from both RNA preparations, subcloned and sequenced, linking the λgt10 derived 5' fragment and the EST derived 3' fragment of mBCNG-2.

PCR cycling was performed as follows: 1x (2 minutes, 94° C.); 25x (45 seconds, 94° C., 30 seconds, 55° C.); 2 minutes, 72° C.); 1x (10 min, 72° C.)

Cloning of mBCNG-3. From the λgt10 library screen for mBCNG-2 (see above) one positively reacting clone was obtained (#15) which appeared to give a consistently weaker hybridization signal. This insert was amplified with oligonucleotides 15.N2 (Seq. ID. No.: 5) and 13.N2 (Seq. ID. No.: 6), subcloned, sequenced and shown to represent a third BCNG-related sequence, different both from mBCNG-1 and mBCNG-2, which was called mBCNG-3. The identified fragment encoded the N-terminal part of the mBCNG-3 sequence up to amino acid 319 (numbering according to mBCNG-1; see FIG. 8).

After obtaining the sequence for EST-M28, an RT-PCR was performed both on mouse brain and heart polyA$^+$ RNA using oligonucleotide B123 as an upstream primer, and degenerate oligonucleotide: 5'-CACCKCRTTGAAGTGGTCCACGCT-3' (Seq. ID. No.: 13) (28REV, corresponding to amino acids 554–561 of the BCNG sequences, numbering according to mBCNG-1; see FIG. 8) as a downstream primer. Extension products of the expected length were obtained from both RNA preparations, subcloned and sequenced. Both represented extension of the mBCNG-3 sequence, as determined by an overlap with the known 3' end of the λgt10 #15 clone. PCR cycling was performed at: 1x (2 minutes, 94° C.); 25x (45 seconds, 94° C., 30 seconds, 55° C., 2 minutes, 72° C.); 1x (10 minutes, 72° C.).

Cloning of hBCNG-1. After obtaining the sequence for EST-H57, an RT-PCR reaction was performed on human brain polyA$^+$ RNA, using oligonucleotides: 5'-ATGTTCGGSAGCCAGAAGGCGGTGGAG-3' (Seq. ID. No.: 14) (MB1–3, corresponding to amino acids 102–110 of the BCNG sequences, numbering according to mBCNG-1; see FIG. 8) as an upstream primer, and 5'-CAGCTCGAACACTGGCAGTACGAC-3' (Seq. ID. No.: 15) (H57.C, corresponding to amino acids 537–544 of the hBCNG-1 sequence, numbering according to mBCNG-1; see FIG. 8) as a downstream primer. A single extension product of the expected length was obtained, subcloned, sequenced, and shown to represent the 5' extension of the hBCNG-1 clone.

PCR was performed as follows: 1x (2 minutes, 94° C.); 25x (45 seconds, 94° C., 20 seconds, 58° C., 3 minutes, 72° C.); 1x (10 minute, 72° C.).

Cloning of hBCNG-2. After obtaining the sequence for EST-H61, a PCR probe was made using oligonucleotides: 5'-AACTTCAACTGCCGGAAGCTGGTG3' (Seq. ID. No.: 16) (H61.A, corresponding to amino acids 452–459 of the hBCNG-2 sequence, numbering according to mBCNG-1; see FIG. 8) as an upstream primer, and 5'-GAAAAAGCCCACGCGCTGACCCAG3' (Seq. ID. No.: 17) (H61.F, corresponding to aa 627–634 of the hBCNG-2 sequence, numbering according to mBCNG-1; see FIG. 8) as a downstream primer on the EST-H61 DNA. This fragment was used to screen a Human Brain Hippocampus cDNA library in λgt10 (CLONTECH, cat. no. HL 3023a), in high stringency. conditions (see above). Positively reacting clones were further screened by PCR, using oligonucleotide: 5'-CACCAGCTTCCGGCAGTTGAAG TTG3' (Seq. ID. No.: 18)(H61.C, corresponding to amino acids 452–459 of the hBCNG-2 sequence, numbering according to mBCNG-1; see FIG. 8) as a downstream primer and either of oligonucleotides 15'.N2 (Seq. ID. No.: 5) or 13'.N2 (Seq. ID. No.: 6) as an upstream primer. The clones yielding the longest amplification products were subcloned and sequenced, thus obtaining the N-terminal region of the hBCNG-2 sequence up to aa 587 (numbering according to mBCNG-1; see FIG. 8).

Northern blots. For mouse gene expression studies, a Mouse Multiple Tissue Northern Blot (CLONTECH, cat. no. 7762-1) was probed with the following PCR products: For mBCNG-1, probe "q0", obtained using oligos q0.5' (5'GCGAATTCAAACCCAACTCCGCGTCCAA3') (Seq. ID. No.: 19) and q0.3' (5'CCTGAATTCACTGT ACGGATGGAT3') (Seq. ID. No.: 20). Amplification product corresponding to aa 6-131 of the mBCNG-1 sequence (see FIG. 7 and FIG. 8). For mBCNG-2, probe "dA", obtained using oligos ASEQ2/HRL.2 (see above). For mBCNG-3, probe "15-7", obtained using oligos 15.N2/ 13.N2 (see above); amplification performed directly on lambda phage DNA (clone #15). For mBCNG-4, probe "M28" was obtained as a gel-purified EcoRI/BglII restriction fragment (400 bp) from the EST-M28 DNA. Fragment corresponding to amino acids 529–607 of the mBCNG-4 sequence (numbering according to mBCNG-1; see FIG. 8), plus 180 nucleotides of the mBCNG-4 3'UTR (untranslated region; see Seq. ID. No.: 11).

For human gene expression studies, a Human Multiple Tissue Northern Blot (CLONTECH, cat. no. 7760-1) or Human Brain Multiple Tissue Northern Blot (CLONETECH, cat. no. 7750-1) was probed with the following PCR products: For hBCNG-1, probe H57, obtained using oligos H57.A (5'GTCGTACTGCCAGTGTTC GAGCTG3')(Seq. ID. No.: 21) and H57.B (5'GGTCAGGTTGGTGTTGTGAAACGC3') (Seq. ID. No.: 22). Fragment corresponding to aa 537–800 of the hBCNG-1 sequence (numbering according to mBCNG-1; see FIG. 8). For hBCNG-2, probe "H61", obtained using oligos H61.A (Seq. ID. No.: 28) and H61.F (Seq. ID. No.: 17)(see above).

Hybridizations were all performed in ExpressHyb solution for 1 hour, 68° C., as indicated in the manufacturer's Protocol Handbook. Washing was performed as follows: 10 minutes, room temperature in 2x SSC/0.1% SDS, followed by twice 30 minutes, 65° C. in 0.2x SSC/0.1% SDS. Filters were stripped between subsequent hybridizations by boiling for 5 min in 0.5% SDS/$H_2O$.

Sequence alignments and EST database search. Alignments and distance calculations were all performed with MegAlign (DNASTAR) on the indicated peptide sequences.

The EST database search was performed with BLAST (NCBI), using the mBCNG-1 polypeptide sequence (amino acids 1–720, to avoid the glutamine repeat present in the C-terminal region of the protein) and the TBLASTN program.

EXAMPLE 3

Physiological and Pharmacological Significance of Mouse and Human BCNG Channel Genes.

Introduction

The unique structural features and the tissue distribution of the predicted proteins of the BCNG gene family suggested that they encode the pacemaker current (variously called Ih, If or Iq) of the heart and brain. Alternatively, it was suggested that it might be a component of other—perhaps unidentified—ionic current(s) that are important in cardiac renal, hepatic and central nervous system function.

The unique structural features of the predicted BCNG proteins (the unusual ion conducting pore (P) domain, the highly conserved cyclic nucleotide binding (CNB) site and the highly conserved and highly charged S4 voltage sensor) indicated that they may be susceptible to multiple drug intervention strategies that target the pore, the cyclic nucleotide binding site and the voltage-dependent gating apparatus.

Analysis And Predicted Structure and General Features of the BCNG Proteins. The predicted amino acid sequence of the BCNG genes revealed that they are members of the voltage-gated ion channel superfamily. Specifically, the BCNG proteins show similarities to the superfamily of channels that includes the voltage-gated $K^+$ channels (Pongs, et al., 1995) and the cyclic nucleotide-gated channels, non-selective cation channels that are permeable to Na, $K^+$ and Ca (Zagotta and Siegelbaum, 1996). As shown schematically in FIG. 11, the BCNG proteins are predicted to have six transmembrane spanning α-helices with cytoplasmic N and C termini, a highly basic fourth transmembrane domain (S4) and pore (p) region. Each of these motifs are found in the members of the voltage-gated $K^+$ family. In addition, the BCNG proteins have a well conserved cyclic nucleotide binding site in the C-terminus. Although a homologous motif is found in some of the voltage-gated $K^+$ channels, the cyclic nucleotide binding sites in those channels are not well conserved and there is little evidence that the binding sites are functional. Indeed, the cyclic nucleotide binding site of the BCNG channels is most homologous to the sites found in cyclic nucleotide gated channels which use the binding of cyclic nucleotides to drive their activation. Furthermore, while the P loops of the BCNG channels are homologous to those found in voltage activated $K^+$ channels and cyclic nucleotide gated channels, there are several non-conservative changes in the amino acid sequence that are likely to yield ion conduction properties that are unique to the BCNG channels. Thus, the BCNG channels appear distinct from all previously identified channels in a number of ways which suggests that they have distinct physiological and pharmacological properties. These similarities and dissimilarities in the sequences of the voltage-gated $K^+$ channels, cyclic nucleotide-gated channels and the BCNG channels and the predicted consequences for BCNG channel functional properties are discussed more extensively below.

Results

The Hydrophobic Core. The core of BCNG channels is predicted to have six transmembrane (α-helical sequences (S1–S6) and a pore forming P loop. This assignment is homologous to a single subunit of the tetrameric $K^+$ channels (and tetrameric cyclic nucleotide-gated channels) or a single repeat in the pseudo tetrameric Na and Ca channels. This homology suggests that the BCNG channels are members of the voltage-gated $K^+$ channel superfamily (which also includes the voltage-independent but structurally homologous cyclic nucleotide-gated channels). It is likely that BCNG channels are composed of four such polypeptides in a hetero or homomultimeric structure as is seen for the voltage-gated $K^+$ channels and the cyclic nucleotide-gated channels (Chen et al., 1993; Bradley et al., 1994; Liman and Back, 1994; Lin et al., 1996). However, mBCNG-1 shows considerable divergence from all other known $K^+$ channel and cyclic nucleotide-gated channel sequences. As noted above, the highest homology in the hydrophobic core region is to mouse Eag (22% amino acid similarity)—a voltage-gated $K^+$ channel that has a degenerate and probably non-functional cyclic nucleotide binding site Warimke and Gancleky. Over this core region, mBCNG-1 shows 17% identity to the voltage independent cyclic nucleotide-gated channels.

In contrast, the proteins that are predicted to be encoded by the BCNG genes show high homology to each other (>80%, see Examples 1 and 2). Indeed, mouse BCNG-1 and human BCNG-1 are identical over the core region. Similarly, mBCNG-2 and hBCNG-2 are 98% identical over the core region. Thus, the BCNG family of genes appears to constitute a new branch of the $K^+$ channel superfamily which could be regulated by cyclic nucleotide binding. The presence of a gene family with members showing such sequence conservation strongly suggests important biological function.

Figure 12:
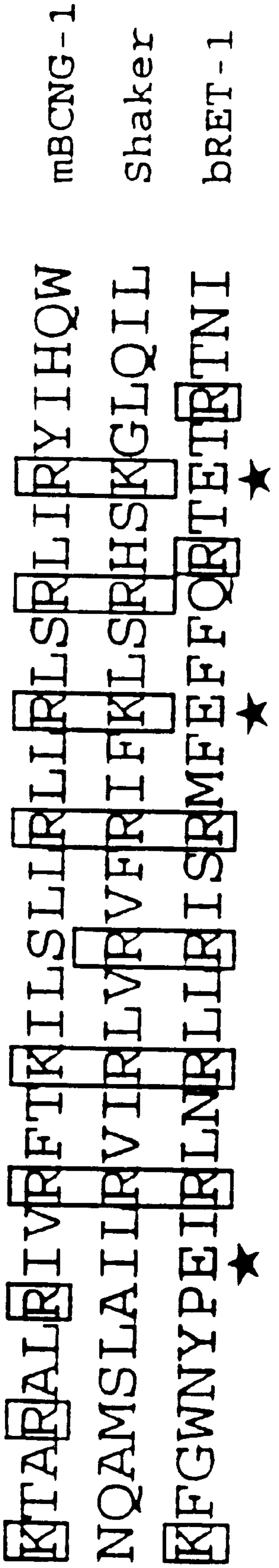
FIG. 12. Alignment of the S4 voltage sensing regions of the prototypical voltage- gated $K^+$channel shaker (Seq.ID.No.:58) and cyclic nucleotide-gated channel bRET1 with the S4 sequence of mBCNG-1 (Seq.ID.No.:51). Boxed residues are positively charged amino acids present in one or more of the S4 sequences. The stars indicate the position of amino acids with negatively charged acidic side chains that are present in the bRET1 sequence (Seq.ID.No.:59).

The S4 voltage-sensing domain. The presence of positively charged arginine and lysine residues at every third position in the fourth transmembrane helix is a signature sequence of voltage-dependent gating (Hille, 1992; Catterall, 1992, see FIG. 12). In contrast, in the voltage-independent cyclic nucleotide-gated channels, the S4 is degenerate with some of the positively charged residues being replaced by negatively charged acidic amino acids or being out of the triad repeat frame. These changes have reduced the net positive charge in the S4 of the cyclic nucleotide-gated channels to 3–4. This introduction of negatively charged residues may underlie the reason that the cyclic nucleotide-gated channels no longer respond to voltage. However, it is also possible that voltage-sensitivity may have been lost as a result of some other structural change in the cyclic nucleotide-gated channels and the divergence in S4 structure is simply a reflection of the loss of evolutionary pressure to retain the positive charges.

The S4 of BCNG channels are most closely related to the corresponding regions in the voltage-gated $K^+$ channels Shaker and eag, albeit poorly (mBCNG-1 is 30% homologous to the S4 of Shaker and eag). Despite an interruption by the inclusion of a serine in place of an arginine in the S4 of BCNG channels, the BCNG sequence contains more positively charged residues than any other member of the voltage-gated $K^+$ channel superfamily (see FIG. 12). The S4 domain of BCNG-1 has up to nine positively charged residues (one group of five and one group of four separated by a serine in place of one other arginine), which again makes it more similar to voltage activated $K^+$ channels (Sh and eag families) than to cyclic nucleotide-gated channels. The retention of such a highly charged S4 strongly suggests that the gating of these channels are voltage-sensitive.

The cyclic nucleotide binding site. Cyclic nucleotides regulate the activity of a diverse family of proteins involved in cellular signaling. These include a transcription factor (the bacterial catabolite activating protein, CAP), the CAMP- and cGMP-dependent protein kinases (PKA and PKG) and the cyclic nucleotide-gated (CNG) ion channels involved in visual and olfactory signal transduction (Shabb and Corbin, 1992; Zagotta and Siegelbaum, 1996). Despite obvious divergence among the effector domains of these proteins, the cyclic nucleotide binding sites appear to share a common architecture. Solution of the crystal structures of CAP (Weber and Steitz, 1987) and a recombinant bovine PKA R1α subunit (Su, et al., 1995) has demonstrated that their cyclic nucleotide binding sites are formed from an α helix (A helix), an eight stranded β-roll, and two more α-helices (B and C), with the C-helix forming the back of the binding pocket. Of the approximately 120 amino acids that comprise one of these cyclic nucleotide binding sites, six are invariant in all CAP, PKA, PKG and cyclic nucleotide gated channels. Thus, it has been suggested that the invariant residues play important—and conserved—roles in the folding and/or function of the CNB sites of these diverse proteins (Shabb and Corbin, 1992; Zagotta and Siegelbaum, 1996; Weber and Steitz, 1987; Su, et al., 1995; Kumar and Weber, 1992; Scott, et al., 1996). Indeed, the crystal structure of CAP (Weber and Steitz, 1987) and the regulatory subunit of recombinant bovine R1α (Su, et al., 1995) reveals that the glycines are at turns within the β-roll while the glutamate and the arginine form bonds with the ribose-phosphate of the nucleotide.

Figure 11:
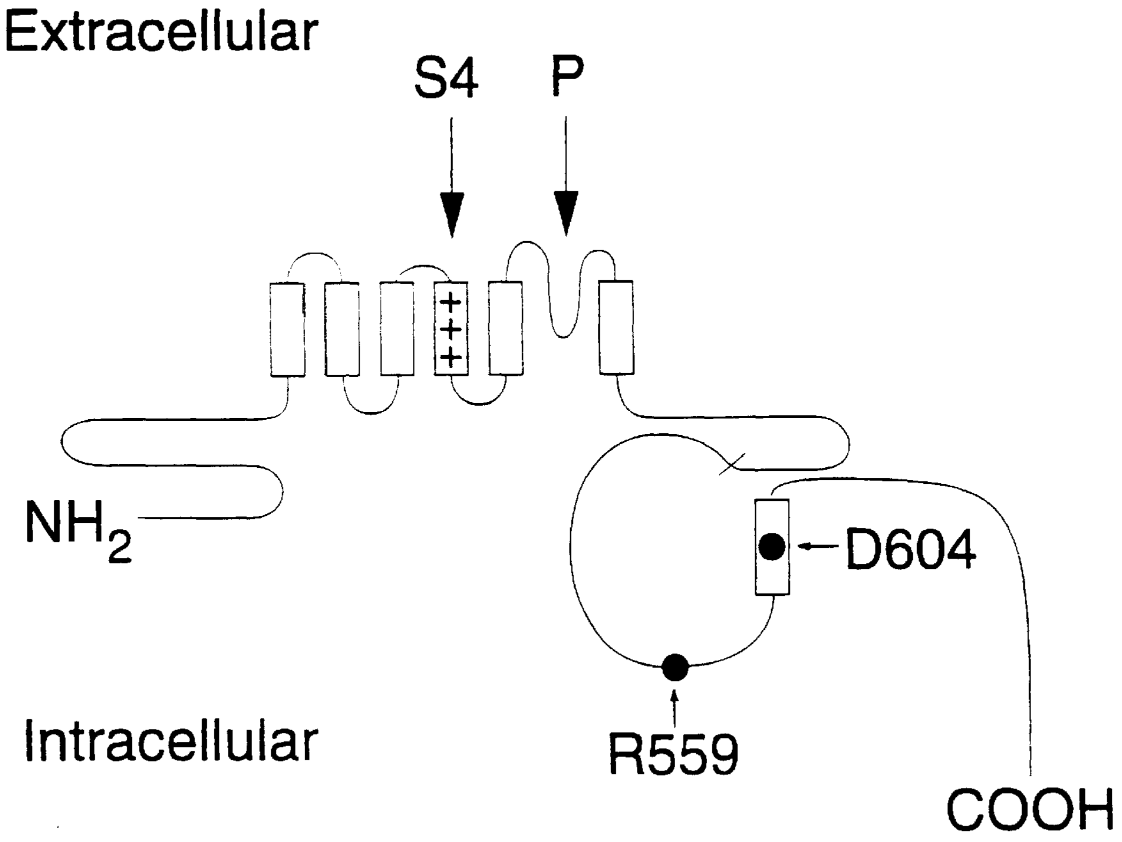
FIG. 11. Schematic representation of the general architecture of the BCNG channel proteins based on homology to the voltage-gated $K^+$channels and the cyclic nucleotide-gated channels.

Interestingly, only three of these residues—two glycines and the arginine—appear to be conserved among the more distantly related voltage-gated channels which bear the CNB site motif but whose gating may NOT be modulated significantly by direct binding of cyclic nucleotide (KAT1 (Hoshi, 1995) and drosophila EAG (dEAG) (Bruggeman, et al., 1993) (see FIG. 11).

Thus in the plant channel, KAT1, the first glycine is mutated to an asparagine and the alanine is changed to a threonine. In dEAG the glutamate in changed to an aspartate. Furthermore, the alignment of dEAG to the highly conserved RXA sequence in β-7 is uncertain. Often, the SAA sequence within the dEAG β-7 is aligned with the RXA consensus sequence which suggests that the arginine is lost and replaced with a serine. RAL is aligned with the RXA consensus sequence which would indicate that the arginine is retained but the alanine is replaced with a leucine. Regardless of which alignment is considered, it is clear that the binding site sequence of KAT1, dEAG and related channels all show deviations from the consensus motif for a functional cyclic nucleotide binding site. In keeping with this structural divergence, there is only one report that any cloned EAG is being sensitive to direct cyclic nucleotide binding (Bruggermann et al., 1993). However, this result has not been confirmed and it is now thought to be an artifact. There is some evidence that the gating of the plant channel KAT1, may be weakly sensitive to cyclic nucleotide modulation (Hoshi, 1995).

Figure 13A:
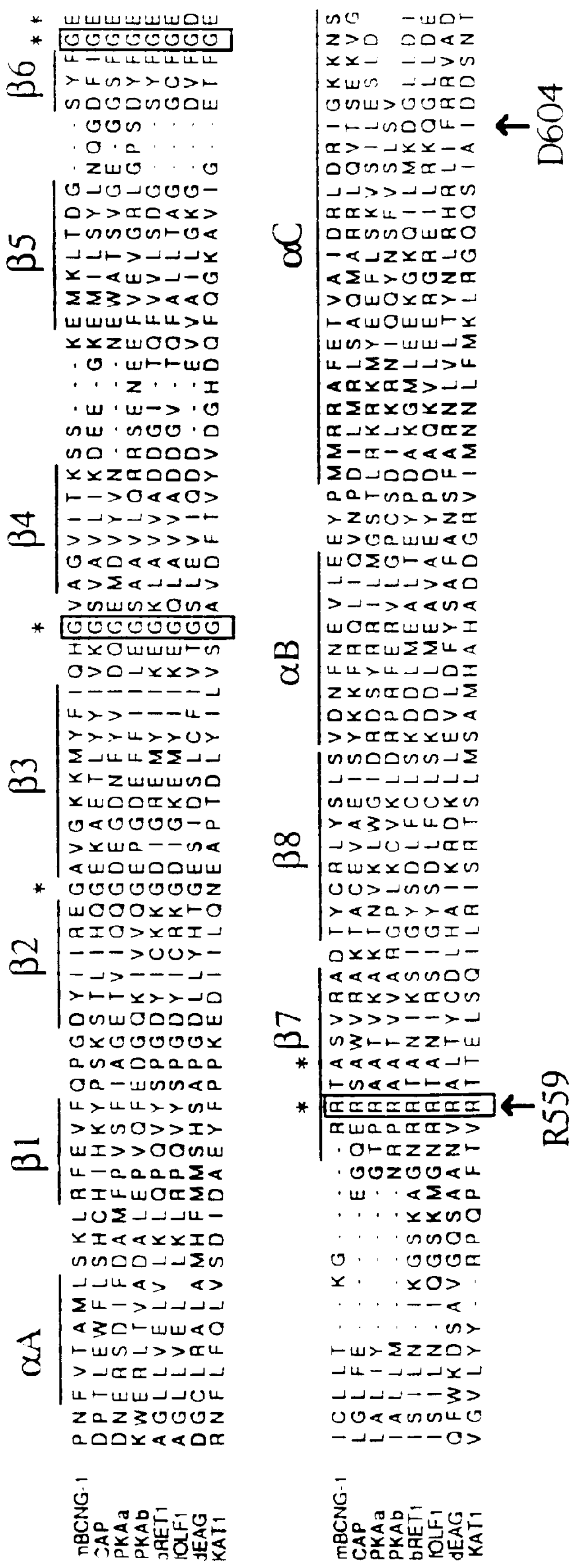
FIGS. 13A–13B.
Figure 13B:
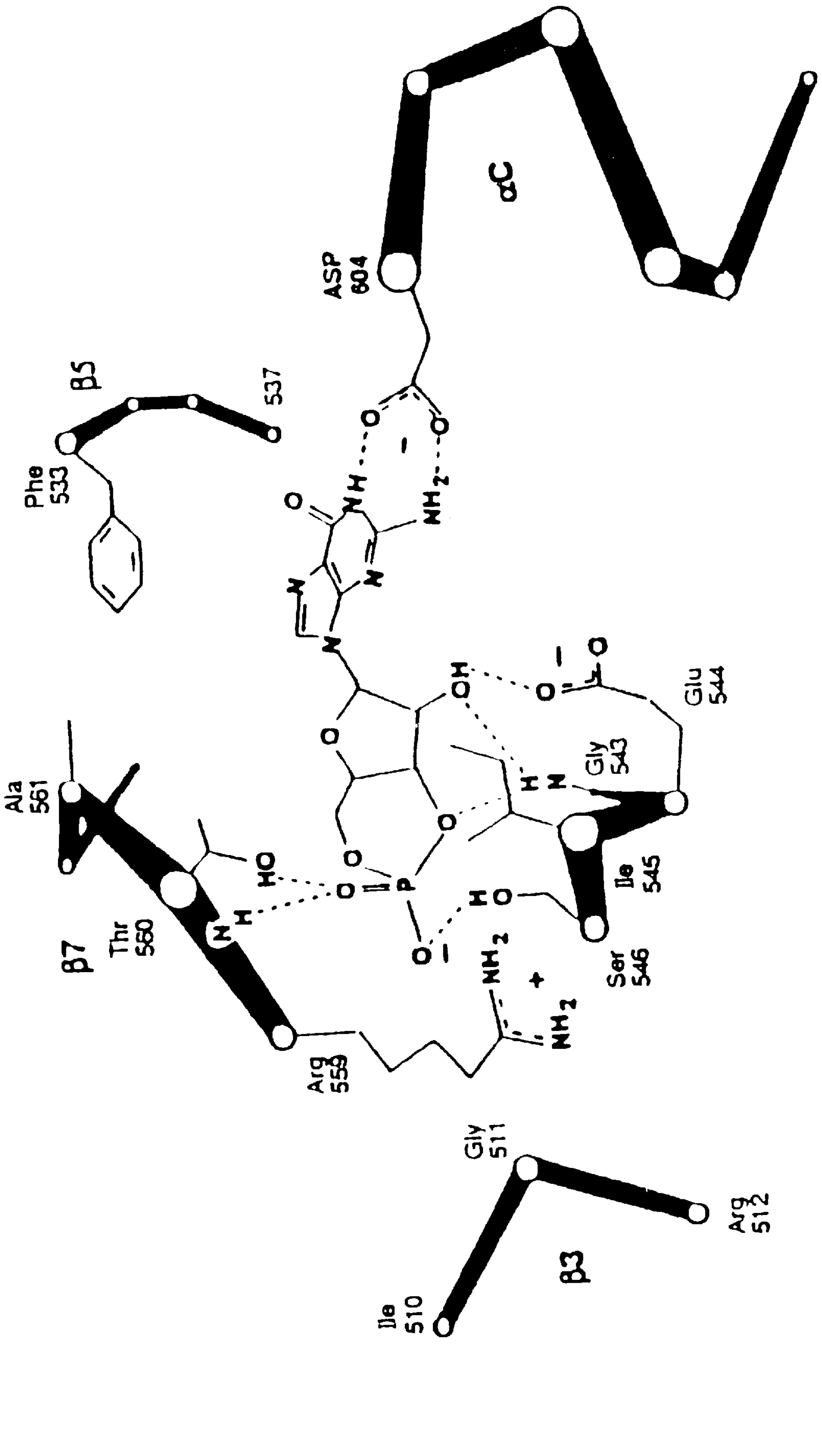

FIG. 13 shows a schematic representation of the cyclic nucleotide binding site of bRET1 showing the critical interactions between the binding site and the cyclic nucleotide.

Recent evidence has demonstrated that the third (or C) α-helix moves relative to the agonist upon channel activation, forming additional favorable contacts with the purine ring. Indeed, the selective activation of bRET1 by cGMP relative to cAMP is largely determined by a residue in the C α-helix, D604 (Varnum et al., 1995). This acidic residue is thought to form two hydrogen bonds with the hydrogens on a ring nitrogen and amino group of the cGMP purine ring. Unlike the cGMP selective bRET1 channel, cyclic nucleotide-gated channels that are activated equally well by cAMP or cGMP (fOLF1, Goulding et al., 1992; Goulding et al., 1994) or which favor activation by cAMP (rOLF2 coexpressed with rOLF1, Liman & Buck, 1994; Bradley et al., 1994) do not have an acidic residue here, but rather, have polar or hydrophobic amino acids (see Varnum, et al., 1995). Neutralization of D604 results in a loss of the ability to form the favorable hydrogen bonds with cGMP and the loss of the unfavorable interaction with the lone pair of electrons on the purine ring of CAMP, thus accounting for the channels which bear a hydrophobic or polar residue at this position becoming non-selective between CAMP and cGMP or even selective for CAMP.

In the C-terminus of the BCNG proteins there is a sequence of approximately 120 amino acids that is homologous to these cyclic nucleotide binding sites. Strikingly, the six residues that have been shown to be totally conserved in all functional cyclic nucleotide binding sites are conserved in all of the BCNG proteins that identified. The cyclic nucleotide binding site of the BCNG channels are most similar to the functional site present in the voltage-independent cyclic nucleotide-gated channels (30%). When the cyclic nucleotide binding sites found in channel genes are compared to those in protein kinases, the BCNG channel sites are more similar (25% similarity to yeast cAMP-dependent protein kinases) than those of any other ion channel. These data strongly suggest that the BCNG genes encode proteins whose activity is modulated by direct binding of cyclic nucleotide. Furthermore, the BCNG channels all have an isoleucine residue in the position where D604 is found in the cGMP selective bRET1 channel. Thus, the BCNG are suggested to be cAMP selective.

The pore. Despite the functional divergence that has given rise to Na, Ca or K selective families and to the presence of channels within these families whose conductances vary by 1–2 orders of magnitude, the pores of all members of the voltage-gated superfamily are related (see Itillic 1992; For example see FIG. 14). Much is known about the residues that contribute to the ion permeation properties of channels and this allows predictions about the permeation properties of the BCNG proteins (Mackinnon, 1991; Heginbothem et al., 1994).

Overall, the P region of mBCNG-1 is most closely related to the corresponding region in the K selective Shaker and eag channels, albeit poorly (30%). Based on the presence of a GYG motif in the P loop, the BCNG proteins would be expected to be K selective. However, the BCNG P loops contain substitutions in several positions that are otherwise highly conserved in other voltage activated $K^+$ channels. These changes can be seen in FIG. 14 (which shows an alignment of mBCNG-1 against channels from all the other major K channel families) and FIG. 8 (which shows the alignment of all currently cloned BCNG sequences). The aspartate residue which follows the GYG triplet is replaced with alanine (position 352) in mouse and human BCNG-1 and by an arginine in the other BCNG channels identified so far. The serine/threonine residue 8 residues N-terminal from that position (residue 344 in mBCNG-1) is replaced with histidine in all of the BCNG sequences. 6 residues N-terminal from the aspartate a hydrophobic leucine residue is introduced in place of a polar residue. In addition, at position −12 from the aspartate, a site that is occupied by an aromatic residue in all of the other channels aligned in FIG. 14, a lysine residue is introduced in all of the BCNG sequences (FIG. 8 and FIG. 14).

Figure 14:
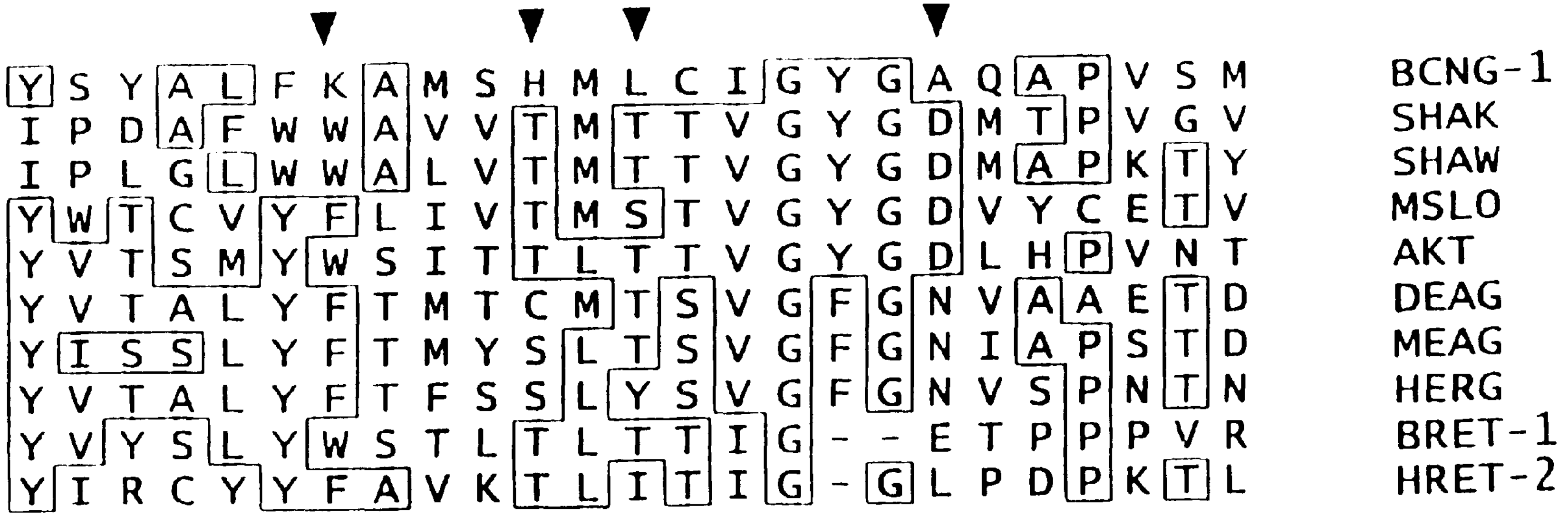
FIG. 14. Alignment of the P loop pore forming regions of the prototypical voltage-gated $K^+$channel shaker and cyclic nucleotide-gated channel bRET1 with the S4 sequence of mBCNG1. The aligned channels are mBCNG-1 (Seq.ID.No.:2), Shaker (SHAK, Papazian et al., 1987; Kamb et al., 1988), SHAW, Wei, et al., 1990) calcium activated K channel (MSLO, Pallanck and Ganetzky, 1994) the plant inward rectifier (AKT Sentenac et al., 1992), drosophila and mouse ether-a-gogo's (DEAG, Warmke et al., 1991; MEAG, Warmke and Ganetzky, 1994) Human ether-a-gogo related gene (HERG, Warmke and Ganetzky, 1994), bovine retinal a-subunit (bRET1, Kaupp et al., 1989) and human retinal β subunit (HRET-2, Chen et al., 1993). The arrows mark positions where the BCNG channels show pronounced and potentially important changes in sequence from the normal motif seen in K selective channels (Seq.ID.Nos.:41–50).

Although the amino acid substitutions seen in the P region of the BCNG subunits do not necessarily indicate that the channel will have lost its K selectivity (for example a lysine is present in the P region of the K selective Shaw channel, See FIG. 14) the substantial deviations from the K channel consensus sequence suggest that the BCNG proteins may generate a family of channels that do not select well between Na and K—consistent with the hypothesis that the BCNG channels encode the non-selective Ih pacemaker current.

Discussion

Significance of the BCNG Structure. The presence of cyclic nucleotide binding sites on a number of $K^+$ channels that are found in both plant and animal phyla suggests that the fusion between an ancestral $K^+$ channel and an ancestral cyclic nucleotide binding site is likely to have occurred prior to the evolutionary separation between plants and animals (Warmke and Ganetzky, 1994). Indeed, the finding that many of these sites are degenerate and non-functional supports this interpretation. Divergence from this common ancestor would have led on one hand to Eag-related channels (EAG, ERG, ELK) (Warmke and Ganetsky, 1994) and plant inward rectifiers (AKT and KAT), which maintained more of the features of voltage activated $K^+$ channels, while showing a progressive deviation from the original cyclic nucleotide binding site sequence) and on the other hand to CNG-channels (which show a higher evolutionary constraint on the cyclic nucleotide binding site, while they have lost voltage activation and $K^+$ selectivity) (Anderson, et al., 1992; Sentenac, et al., 1992). The features of BCNG-1 suggest that it may have remained closer to the ancestral molecule that represents the evolutionary link between voltage-gated $K^+$ channels and cyclic nucleotide-gated channels. This is supported by the observations that the cyclic nucleotide binding site of mBCNG-1 shows the closest homology to binding sites present in protein kinases, in particular in yeast cAMP-dependent protein kinases (25%) while the channel domains are most closely related to the voltage-dependent channel encoded by the Shaker gene that does not have a cyclic nucleotide binding site and thus, presumably arose before the gene fusion event. The cyclic nucleotide binding site of mBCNG-1 is most homologous to the site present in cyclic nucleotide-gated channels (30%) which again demonstrates that these probably arose from a common ancestor and in both there was pressure to maintain the cyclic nucleotide binding site because it contributed to the function of the protein. Thus, BCNG-1 appears to constitute a new branch of the $K^+$ channel superfamily.

Physiological Significance. Ion channels are central components underlying the electrical activity of all excitable cells and serve important transport functions in non-excitable cells. Members of the novel BCNG family of ion channels are expressed in both brain and cardiac muscle as well as skeletal muscle, lung, liver, pancrease and kidney. From their amino acid sequence, members of the BCNG channel gene family are likely to have important, novel roles in the electrophysiological activity of the brain and the heart and other tissues. This view is based, first, on the finding that MRNA coding for BCNG channel protein is expressed in both heart and brain. Second, the deduced primary amino acid sequence of the BCNG channels indicate that they are members of the voltage-gated channel family but unlike most voltage-gated channels, the BCNG channels contain what appears to be a functional cyclic nucleotide-binding domain in their carboxy terminus.

Northern blots of the four mouse BCNG channel genes show interesting differences in expression patterns (see FIG. 3, FIG. 9 and FIG. 10). mBCNG-1 is selectively expressed in brain. Western blots confirm that mBCNG-1 is also highly expressed at the protein level, and that this expression is widespread throughout the mouse brain (see FIG. 2). mBCNG-2 is expressed in brain and heart. mBCNG-3 is expressed in brain, heart, lung and skeletal muscle. mBCNG-4 is expressed in brain, liver and kidney. Thus, each gene, although highly similar at the amino acid level, shows a distinct pattern of expression, implying that each has a unique physiological function. This is borne out by the finding that the two human members of the BCNG family, hBCNG-1 and hBCNG-2, show similar patterns of expression to the mouse homologs. Thus, hBCNG-1 is selectively expressed in brain (with weaker hybridization in pancrease) whereas hBCNG-2 is expressed in brain and heart. Even within a particular organ system, the different genes show different patterns of expression. Thus, in the brain hBCNG-1 is more highly expressed in hippocampus and amygdala than in other brain regions. In contrast, hBCNG-2 is highly expressed in all brain regions.

Based on the BCNG amino acid sequence and tissue distribution, it was hypothesized that the channels encode a either a voltage-gated potassium channel that is activated by membrane depolarization and modulated by the direct binding of cyclic nucleotides, or the hyperpolarization-activated pacemaker channel that underlies spontaneous electrical activity in the heart (DiFrancesco and Torta, 1991) and in various regions of the brain (Steride et al., 1993). This latter hypothesis is based on the finding that the pacemaker channels, similar to BCNG genes, are expressed in both brain and the heart. Moreover, the pacemaker channels are known to be non-selective cation channels that are gated by both voltage and the direct binding of cyclic nucleotides to a cytoplasmic site on the channel (DiFrancesco and Torta, 1991; Pedarzani and Storm, 1995 Larkman And Kelly, 1997, McCormick and Page, 1990). To date, there is no biochemical or molecular biological information as to the nature of the pacemaker channel.

However, the similarity in tissue distribution and proposed gating mechanisms between the pacemaker channels and the BCNG channels suggested that the BCNG genes code for one or more subunits that comprise the pacemaker channels.

Figure 15A:
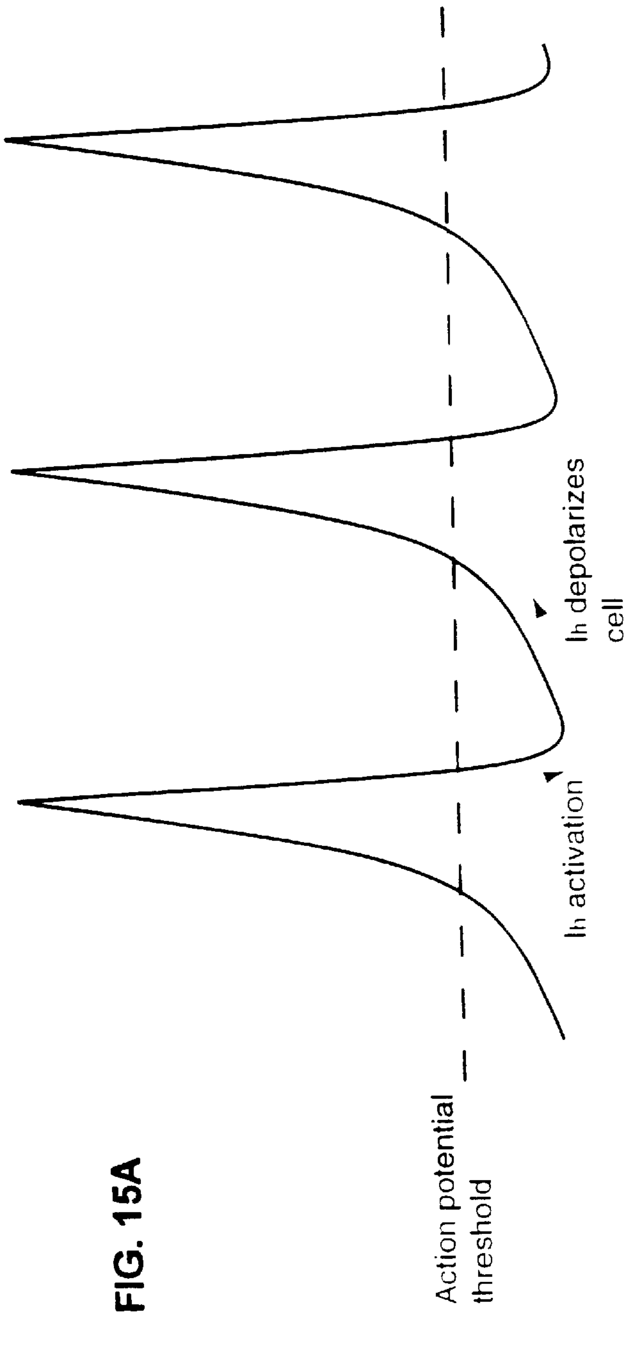
FIGS. 15A–15B. Schematic representation of repetitive firing of a pacemaker neuron and its involvement in the generation and regulation of rhythmic firing patterns.
Figure 15B:
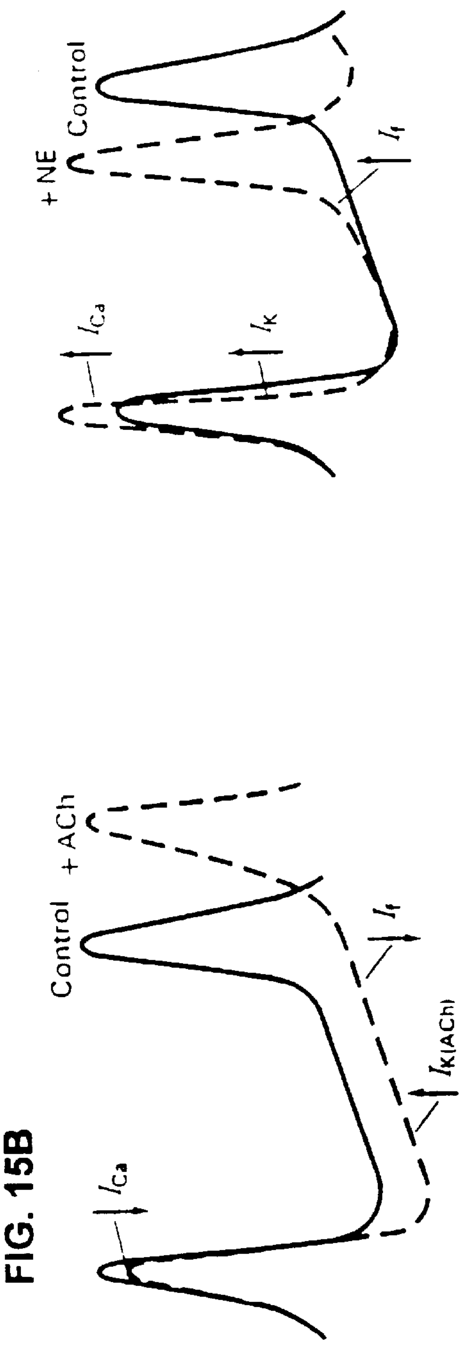

Pacemaker channels have been studied at the electrophysiological level in both cardiac tissue and central neurons. In both instances, the channels are activated when the cell membrane voltage is made more negative than −40 mV. These non-selective channels are permeable to both Na and $K^+$ ions. However, at the negative membrane potential range over which these channels open, their main effect is to allow positively charged sodium to enter the cell from the extracellular environment, causing the cell membrane to become more positive. This eventually causes the membrane voltage to reach threshold and the cell fires an action potential. (See FIG. 15). Cyclic AMP (cAMP) is known to shift the relation between membrane voltage and channel activation, causing the channels to turn on more rapidly when the membrane is depolarized. This increases the rate of the pacemaker depolarization, increasing the rate of spontaneous action potential firing. It is this effect that underlies the ability of epinephrine (adrenaline) to cause the heart to beat faster. The effects of cAMP on the pacemaker current appear to occur through two separate molecular mechanisms. First, cAMP activates the enzyme, cAMP-dependent protein kinase (PKA), leading to an increase in levels of protein phosphorylation. Second, cAMP is thought to directly bind to a cytoplasmic region of the pacemaker channel, producing an effect similar to that seen with protein phosphorylation. Such direct actions of cAMP have been reported both in the heart and in brain (DiFrancesco and Torta, 1991; Pedarzani and Storm, 1995).

An alternative function for the BCNG channels, that they encode for a novel voltage-gated and cyclic nucleotide-gated potassium channel, is suggested by the amino acid region that is known to line the ion-conducting pore and hence determine the ionic selectivity of the channel. This S5–S6 loop contains a three amino acid motif, GYG, that is conserved in almost all voltage-gated $K^+$ channels Heginbotham et al., 1994. The BCNG channel S5–S6 loop shows amino acid similarity with that of other potassium channels, including the GYG motif. This suggests that the BCNG channels may be $K^+$ selective. However, there are a number of striking differences in the sequence between BCNG and other $K^+$ channels that may indicate that the BCNG channels are less K-selective compared to other $K^+$ channels, consistent with the view that the BCNG channels code for the non-selective cation pacemaker channels that are permeable to both Na and $K^+$.

The presence of mBCNG-1 in the dendrites of hippocampal pyramidal cells is particularly intriguing, as cAMP has been shown to be important for the establishment of some forms of long-term synaptic potentiation in these cells (Frey, et al., 1993; Boshakov, et al., 1997; Huang and Kandel, 1994; Thomas, et al., 1996). The structural features of mBCNG-1 predict a $K^+$ conducting activity, directly modulated by cyclic nucleotide binding.

Interestingly, a current with similar characteristics has been described in the hippocampal pyramidal neurons of area CA1 (Warmke, et al., 1991) where mBCNG-1 is highly expressed. This current (IQ) is believed to contribute to the noradrenergic modulation of hippocampal activity, by regulating neuronal excitability in response to cAMP levels. BCNG-1 may participate in the formation of the channels responsible for this type of current.

Based on the widespread tissue distribution and likely important physiological role of the BCNG channels in electrical signaling, drugs that interact with these channels are of potential therapeutic use in a number of neurological, psychiatric and cardiac diseases as well as systemic diseases of tissues such as skeletal muscle, liver and kidney.

Neurological disease: Based on the high expression of these channels in the hippocampus and potential role in spontaneous pacemaker activity, they may be useful, novel targets for treatment of epilepsy. For example, by blocking these channels it may be possible to prevent or diminish the severity of seizures. In diseases associated with hippocampal neuronal loss, such as age-related memory deficit, stroke-induced memory loss, and Alzheimers disease, a drug which enhanced pacemaker channel activity may be of therapeutic use by increasing neuronal activity in the hippocampus. As these channels are also expressed in the basal ganglia and striatum, they may be potential targets in Parkinson's and Huntington's disease. The BCNG channels are also highly expressed in the thalamus, where pacemaker channels have been shown to be important in generating spontaneous action potentials important for arousal. Targeting of such channels may help treat attention deficit disorder.

Psychiatric disease: Given the high levels of expression of hBCNG-1 in the amygdala, these channels may be targets for drugs involving various affective disorders and anxiety. Their high expression in the limbic system suggests that they may also be of potential benefit in treatment of schizophrenia.

Cardiac disease: The expression of the BCNG-2 channels in the heart suggests that they may be useful targets for treatment of certain cardiac arrhythmias. Based on the hypothesis that these genes may encode pacemaker channels, the BCNG channels will be potential targets for treating both bradyarrhythmias through drugs that enhance pacemaker channel activity and certain tachyarrhythmias due to enhanced automaticity. Even if the BCNG channels are not the pacemaker channels, they are likely to play an important role in cardiac electrical activity, perhaps contributing to action potential repolarization, and thus would remain attractive targets for drug development.

A number of drugs, toxins and endogenous compounds are known to interact with various types of ion channels. These drugs have proved useful as local anesthetics and in the treatment of cardiac arrhythmias, hypertension, epilepsy and anxiety. These drugs fall into several classes including pore blockers, allosteric modulators, and competitive antagonists (see Table II). The BCNG channels present some unique features that make them very attractive drugs. First, there are both brain specific genes (BCNG-1) and genes that expressed in both brain and heart (BCNG-2,3). Thus BCNG may yield drugs specific for brain or heart. Second, the pore region of the BCNG channels shows considerable divergence from that of other known potassium channels. Thus, yielding pore-blocking drugs that would selectively alter BCNG channels but spare other types of voltage-gated $K^+$ channels. Third, the cyclic nucleotide-binding site elucidate another important target with respect to the opening of the BCNG channels. By designing specific cyclic nucleotide analogs it should be possible to design either synthetic agonists, which will increase channel opening, or antagonists which will decrease channel opening. Most available drugs for ion channels decrease channel opening, relatively few increase channel opening. The ability to either increase or decrease the opening of BCNG channels offers much potential for therapeutically effective compounds. For example in bovine photoreceptor CNG channels, Rp-cGMPS is an antagonist of channel opening whereas Sp-cGMPS is an agonist (Kramer and Tibbs, 1996). Moreover, the amino acid sequence of the cyclic nucleotide binding site of the BCNG channels shows considerable divergence with cyclic nucleotide binding sites of protein kinases and the cyclic nucleotide-gated channels of olfactory and photoreceptor neurons. Thus it should be possible to design cyclic nucleotide analogs which specifically target the BCNG channels.

TABLE II

Selected Drugs and Toxins That Interact with Members of the Voltage-gated Ion Channel Family

| Compound | Channel Targets | Site of action | Therapeutic Uses |
|---|---|---|---|
| Local Anesthetics (lidocaine, procaine, etc.) | Na | Pore (S6) | Local analgesia, arrhythmias |
| diphenylhydantoin | Na | Pore | Seizures |
| Tetrodotoxin | Na | Pore | |
| Saxitoxin | Na | Pore | |
| α, β-Scorpion toxin | Na | Activation and Inactivation gates | |
| Dihydropyridines | Ca (L-type) | Pore | arrhythmias, hypertension, angina |
| Verapamil | Ca (L-type) | Pore | |
| Diltiazem | Ca (L-type) | Pore | |
| w-conotoxin | Ca (N-type) | Pore | |
| w-agatoxin | Ca (P-type) | Pore | |
| Tetraethylammonium | K | Pore | |
| 4-aminopyridine | K | Pore | |
| charybdotoxin | K | Pore | |
| hanatoxin | K | activation Gate | |
| amiodarone | K | ? | arrhythmias |
| 1-cis-diltiazem | CNG | Pore | |
| Rp-cAMPS | CNG | Binding site antagonist | |
| Sp-cAMPS | CNG | Binding site agonist | |

Hille, 1992; Catterall, 1992; Roden, 1996.

From their amino acid sequence, these channels are likely to have three important physiological properties that make them a priori attractive targets for drug development. First, their gating should be voltage-dependent and thus it should be sensitive to modulation of the voltage-gating mechanism. Second, they possess a cyclic nucleotide binding domain in their C-terminus and it is probable that their gating will be modulated by direct binding of cyclic nucleotides. Third, the unusual sequence of the pore forming domain of the BCNG channels should allow the ion conduction properties of the channel to be selectively targeted.

If, the gating of the channels involves both the voltage-sensor machinery and the cyclic nucleotide binding site it is likely that coordinated drug regimes such that two compounds with low efficacy and even low selectivity can combine to selectively target the BCNG channels. Thus one compound that alone would have weak pharmacological effects on many voltage-activated channels combined with one that has a similarly weak effect on the various cyclic nucleotide binding pockets could be applied together. As no class of molecules is currently known that functionally combines BOTH of these structural elements—with the anticipated exception of the BCNG channels—it is likely that such a regime would lead to a highly efficacious and selective targeting of channels containing the BCNG subunits. Selective intervention against BCNG sub-types should also be possible.

The regulation of these channels through drugs provides a unique opportunity for regulating electrical activity associated with diseases as diverse as epilepsy and cardiac arrhythmias. Moreover, the cyclic nucleotide binding domain of these channels provides a unique pharmacological target that could be used to develop novel, specific, cyclic nucleotide agonists or antagonists to upregulate or downregulate channel function.

Drugs can modulate voltage-dependent gating—coupled with CNG to achieve selectivity.

Cell lines expressing mBCNG-1, mBCNG-2, mBCNG-3, mBCNG-4, hBCNG-1 and hBCNG-2 offer the promise of rapid screening for compounds that interact with the channels. To identify drugs that interact with the cyclic nucleotide binding domain, this region could be expressed selectively in bacteria and then purified. The purified protein fragment could then be used in standard ligand-binding assays to detect cyclic nucleotide analogs that bind with high affinity.

Functional effects of drugs on channel opening or ion permeation through the pore are tested using whole cell patch clamp of mammalian cell lines expressing the various BCNG genes. Where the BCNG channels resemble the CNG channels, they exhibit significant permeability to calcium. This permits a high throughput screen in which channel function is assessed by imaging intracellular calcium concentration. Drugs that increase channel opening also increase internal calcium.

EXAMPLE 4

Functional Expression of mBCNG-1 in Xenopus

Oocytes Reveals a Hyperpolarization-activated Cation Current Similar to Native Pacemaker Current. [Identification of a gene encoding a hyperpolarization-activated "pacemaker" channel of brain]

Introduction

The generation of pacemaker activity in heart and brain is mediated by hyperpolarization-activated cation channels that are directly regulated by cyclic nucleotides. We previously cloned a novel member of the voltage-gated K channel family from mouse brain (mBCNG-1) that contained a carboxy-terminal cyclic nucleotide-binding domain (Santoro et al., 1997) and hence proposed it to be a candidate gene for pacemaker channels. Heterologous expression of mBCNG-1 demonstrates that it does indeed code for a channel with properties indistinguishable from pacemaker channels in brain and similar to those in heart. Three additional mouse genes and two human genes closely related to mBCNG-1 display unique patterns of mRNA expression in different tissues, including brain and heart, demonstrating that these channels constitute a widely-expressed gene family.

The electrical activity of both the heart and the brain depends on specialized cells which act as pacemakers, generating the rhythmic, spontaneous firing of action potentials which can control muscle activity, certain rhythmic autonomic functions, and particular behavioral states. In normal nerve or muscle cells, pacemaker activity is characterized by spontaneous firing of action potentials that is intrinsic to the cell and independent of synaptic input. Defects in pacemaker activity can lead to both inherited (Spellberg, 1971) and acquired (Bigger and Reiffel, 1979) cardiac arrhythmias and may also underlie various neurological diseases.

In many of these cases, the pacemaker activity is generated by a hyperpolarization-activated channel that is permeable to both sodium and potassium and is present in both heart (DiFrancesco, 1993) and brain (Pape, 1996). Such cation-permeable channels were initially described in cardiac sinoatrial node cells (Brown et al., 1979; Yanagihara and Irisawa, 1980; Brown and DiFrancesco, 1980; DiFrancesco, 1986), where they were termed $I_f$ or $I_h$. They have since been described in cardiac Purkinje fibers (DiFrancesco, 1981), ventricular muscle (Yu et al., 1993), and both peripheral (Mayer and Westbrook, 1983) and central neurons (Halliwell and Adams, 1982; see Pape, 1996 for review), where they are referred to as $I_h$ or $I_q$. In sinoatrial node cells of the heart, the best studied example, this pacemaker channel drives the rhythmic firing and beating of the atria and ventricles (Brown et al., 1979; Yanagihara and Irisawa, 1980; Brown and DiFrancesco, 1980; although see Irisawa et al., 1993). In fact, it is through the modulation of this pacemaker channel that acetylcholine and norepinephrine exert their classical actions on heart rhythm.

In the brain, the modulation of pacemaker channel activity in thalamic relay neurons is important for regulating arousal during the sleep-wake cycle (Pape and McCormick, 1989; McCormick and Bal, 1997). Pacemaker activity in brainstem nuclei is likely to contribute to respiratory rhythms (Johnson and Getting, 1991; Dekin, 1993). Finally pacemaker activity in higher cortical regions is thought to contribute to endogenous oscillations that may be important for synchronizing the activity of neuronal populations (Maccaferri and McBain, 1996; Strata et al., 1997), a synchronization that has been proposed to bind together the separate analyzed components of a perceptual representation (Singer and Gray, 1995). Although the role of this channel in pacemaker activity may be its best characterized action, it also contributes to rebound excitation following hyperpolarizing responses in non-pacemaking cells (Fain et al., 1978; Attwell and Wilson, 1980; Wollmuth and Hille, 1992; Halliwell and Adams, 1982; Mayer and Westbrook, 1983) and may have additional functional roles.

One striking feature of the pacemaker channels is that their activity can be modulated by transmitters and hormones acting through the second messenger cAMP (Tsien, 1974; DiFrancesco and Tortorra, 1991). Elevation of cAMP levels shifts the voltage-dependence of pacemaker channel activation by 2–10 mV in the positive direction. As a result, the channels activate more rapidly and more completely upon repolarization to a fixed, negative potential. Indeed, it is the ability of cAMP to modulate the activation of the pacemaker current that is largely responsible for the increase in heart rate in response to β-adrenergic agonists (Brown et al., 1979) and the slowing of the heart rate during vaginal stimulation (DiFrancesco et al., 1989; Zaza et al., 1996). Intriguingly, this effect of cAMP appears to be mediated through its direct binding to the channel in both sinoatrial node cells (DiFrancesco and Tortora, 1991) and in neurons (Pedarzani and Storm, 1995; Ingram and Williams, 1996). By contrast, $I_f$ is regulated by PKA-dependent protein phosphorylation in cardiac Purkinje cells (Chang et al., 1991).

Pacemaker activity is characterized by spontaneous firing of action potentials in a nerve or muscle cell that is intrinsic to the cell and independent of synaptic input. This spontaneous firing is generated by a slow, pacemaker depolarization that is thought to involve the turning on of the hyperpolarization-activated pacemaker channels (DiFrancesco, 1993). Such cation-permeable channels were initially described in cardiac sinoatrial node cells (Brown et al., 1979; Yanagihara and Irisawa, 1980; Brown and DiFrancesco, 1980; DiFrancesco, 1986), where they were termed $I_f$ or $I_h$. They have since been described in cardiac Purkinje fibers (DiFrancesco, 1981), ventricular muscle (Yu et al., 1993), and both peripheral (Mayer and Westbrook, 1983) and central neurons (Halliwell and Adams, 1982; see Pape, 1996 for review), where they are referred to as $I_h$ or $I_q$.

The pacemaker channels, unlike most voltage-gated channels, are closed when the membrane is depolarized during an action potential and only open when the membrane repolarizes to negative voltages. The opening of these channels upon repolarization of the action potential permits an influx of positively charged sodium ions, contributing to the spontaneous pacemaker depolarization. If this depolarization is of sufficient amplitude it can then trigger a second action potential, leading to repetitive, rhythmic, electrical activity. Although there is much evidence that supports a role for these channels in pacemaking (DiFrancesco, 1993; 1995; Pape, 1996), their exact quantitative contribution remains controversial (Irisawa et al., 1993; Vassalle, 1995).

One striking feature of the pacemaker channels is that their activity can be modulated by transmitters and hormones acting through the second messenger cAMP (Tsien, 1974; DiFrancesco et al., 1986). Elevation of cAMP levels shifts the voltage-dependence of pacemaker channel activation by 5–10 mV in the positive direction. As a result, the channels activate more rapidly and more completely upon repolarization to a fixed, negative potential. Indeed, it is the ability of cAMP to speed up the activation of the pacemaker current that is largely responsible for the increase in heart rate in response to β-adrenergic agonists (Brown et al., 1979) and the slowing of the heart rate during vagal stimulation, when ACh acts through muscarinic receptor stimulation to decrease cAMP levels (DiFrancesco et al., 1989; Zaza et al., 1996). Intriguingly, this effect of cAMP appears to be mediated through its direct binding to the channel in both sinoatrial node cells (DiFrancesco and Tortora, 1991; DiFrancesco and Mangoni, 1994; Bois et al., 1997) and in neurons (Pedarzani and Storm, 1995; Ingram and Williams, 1996). By contrast, If is regulated by PKA-dependent protein phosphorylation in cardiac Purkinje cells (Chang et al., 1991).

Despite the intense physiological characterization of pacemaker function and mechanisms, the molecular nature of the hyperpolarization-activated cation channel that is responsible for generating the pacemaker depolarization has not yet been identified. For several reasons, we suspected that one candidate gene for the pacemaker channel might be mBCNG-1, which was originally cloned from a mouse brain cDNA library based on its interaction with the SH3 domain of a neural specific isoform of Src (Santoro et al., 1997). First, the deduced amino acid sequence of mBCNG-1 (originally termed BCNG-1 by Santoro et al.) reveals it to be a member of the superfamily of voltage-gated K channels (Jan and Jan, 1997), but with an unusual pore. Second, the carboxy terminus has a conserved cyclic nucleotide-binding (CNB) domain that is homologous to CNB domains of protein kinases (Shabb and Corbin, 1992) and the cyclic nucleotide-gated channels (Zagotta and Siegelbaum, 1996). This suggests its gating may be directly regulated by cyclic nucleotides. Third, both mBCNG-1 mRNA and protein are widely expressed in brain. mBCNG-1 was a candidate gene for the pacemaker channel (Santoro et al., 1997), which codes for a member of the superfamily of voltage-gated K channels (Jan and Jan, 1997). This channel was originally cloned from a mouse brain cDNA library based on its interaction with the SH3 domain of a neural specific isoform of Src (n-Src). The channel protein and mRNA are widely expressed in brain. The deduced amino acid sequence of mBCNG-1 (Seq.ID.No.:2) (originally termed BCNG-1 by Santoro et al.) contains a carboxy terminus, cyclic nucleotide-binding domain that is homologous to CNB domains of protein kinases (Shabb and Corbin, 1992) and the cyclic nucleotide-gated channels (Zagotta and Siegelbaum, 1996). Based on the fact that mBCNG-1 appeared to encode for a subunit of a voltage-gated channel that could be directly regulated by cyclic nucleotides and its widespread distribution in the brain, it was suggested that mBCNG-1 might code for a subunit of the hyperpolarization-activated cation current (Santoro et al., 1997).

Here we report the functional expression of mBCNG-1 in Xenopus oocytes. Patch clamp recordings clearly demonstrate that this gene encodes a hyperpolarization-activated cation channel that is identical in its four key properties to the endogenous pacemaker channel of brain and also bears considerable similarity to that of the heart. Moreover, we report partial cDNA clones coding for three additional members of the BCNG family from mouse brain (mBCNG-2,3,4). These three additional clones are also expressed in a variety of other tissues, including the heart. Because of the potential clinical importance of this gene family, we have also isolated and characterized two human clones that are highly conserved with and show similar expression patterns to mBCNG-1 and mBCNG-2. Thus, the BCNG channel genes may encode not only pacemaker channels of the brain but they may also encode a family of channels that are widely expressed in a variety of tissues, including the heart.

Results

The location and deduced amino acid sequence of mBCNG-1, a gene which encodes a novel memeber of the superfamily of of voltage-gated K channels, suggested to us that it might encode the hperpolarization-activated pacemaker-type channel present in brain. To test this idea directly, we synthesized mBCNG-1 cRNA, expressed it in Xenopus oocytes, and analyzed the functional properties of the expressed channels in cell-free membrane patches. The native brain pacemaker channel has four distinctive properties: 1) it is activated with slow kinetics by hyperpolarization, 2) it is a cation channel that selects weakly for K relative to Na; 3) it is blocked by external Cs but not by Ba, and 4) it is directly modulated by intracellular cAMP. Expression of mBCNG-1 generates channels with each of these four properties as is demonstrated below.

Functional expression of mBCNG-1 in Xenopus oocytes reveals a hyperpolarization-activated cation current similar to native neuronal pacemaker current.

Figures 16A, 16B, 16C, 16D:
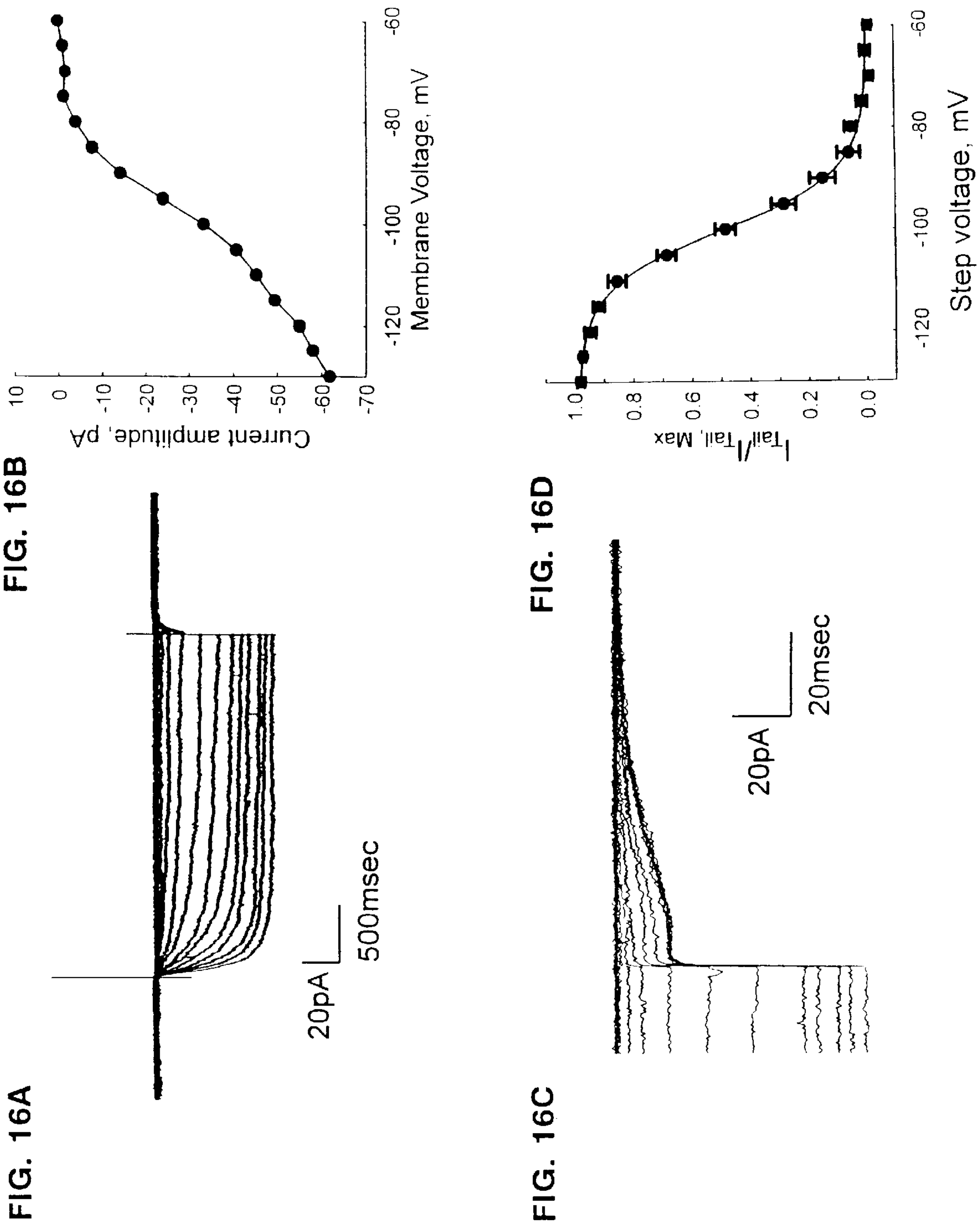
FIGS. 16A–16F. mBCNG-1 expression gives rise to a hyperpolarization-activated current that resembles the native neuronal pacemaker current.
Figure 16F:
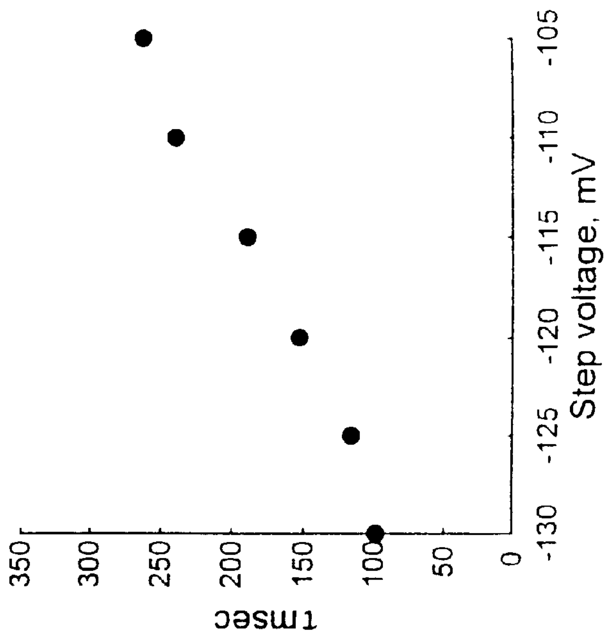
Figure 16E:
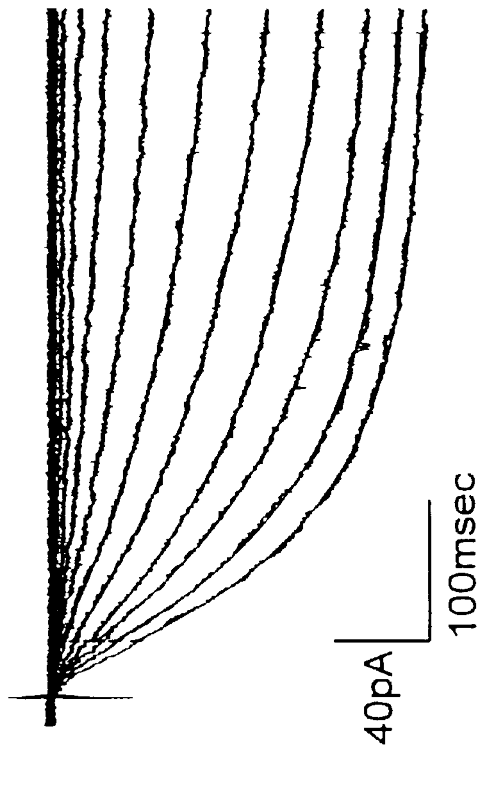

Patches obtained from oocytes injected with mBCNG-1 cRNA display hyperpolarization-activated ionic currents that resemble those seen in native neuronal pacemakers (FIGS. 16A–F). These currents activate when the membrane is hyperpolarized from a holding potential of −40 mV to test potentials below −80 mV (FIGS. 16A, 16B) The inward currents turn on with a relatively slow time course at less negative potentials but their rate of activation speeds up with increasing levels of hyperpolarization (FIGS. 16A, 16E, 16F). Upon return to the holding potential (−40 mV), the currents deactivate relatively quickly, generating a decaying, inward tail current (FIG. 16C).

Hyperpolarizing steps to −130 mV typically activate between −20 pA to −200 pA of current among the >50 different patches from which we have recorded (patches with less than 5 pA of current were frequently observed but could not be analyzed). Such currents were not observed in uninjected control oocytes or in oocytes injected with cRNA encoding the bovine rod photoreceptor CNG channel, a voltage-independent channel that is activated by cGMP. As the single channel conductance of $I_f$ is around 1 ps (DiFrancesco, 1986), we estimate that these patches (~1–2 $\mu m^2$ membrane area) typically contain 50–1500 mBCNG-1 channels, indicating a robust level of expression. The absence of discernable single channel currents in patches that display low current densities (<2 pA), is consistent with mBCNG-1 channels displaying the small single channel conductance of the native pacemaker channels.

Both the time course of activation upon hyperpolarization and time course of deactivation upon return to the holding potential show characteristic sigmoidal kinetics (FIGS. 16C, 16E), similar to those reported for the $I_f$ current in native cells (DiFrancesco, 1984). Following an initial lag, the time course of activation could be approximated by a single exponential function (FIG. 16E), the time constant of which decreases from 290±37 ms at −105 mV (mean±s.e.m., n=5) to 98±14 ms (n=5) at −130 mV (FIG. 16F, Table III).

TABLE III

Biophysical Properties of mBCNG-1

| | CONTROL | | | | cAMP | | 2 mM Cs |
|---|---|---|---|---|---|---|---|
| | $V_{1/2}$(mV) | Slope (mV) | $\tau_{-130}$ (ms) | $\tau_{-105}$ (ms) | $\Delta V_{1/2}$(mV) | Slope (mV) | % inhibition |
| MEAN | −99.9 | −5.96 | 97.8 | 287.4 | 1.8 | −6.30 | 92.4 |
| SEM | 0.8 | 0.71 | 13.6 | 37.0 | 0.3 | 0.71 | 2.5 |
| n | 5 | 5 | 5 | 5 | 5 | 5 | 6 |

TABLE III. SUMMARY OF BIOPHYSICAL PROPERTIES OF mBCNG-1. Control. Average values for steady-state activation parameters: $V_{1/2}$ and slope, from Boltzmann equation fit to tail-current activation curves; mean time constants of activation for steps to −130 and −105 mV. cAMP. Mean effect of cAMP on $V_{1/2}$ and slope of steady-state activation curve. Shift in $V_{1/2}$ measured by averaging $V_{1/2}$ values before cAMP and after washout and subtracting this average from $V_{1/2}$ value in presence of cAMP (1, 30 or 3000 $\mu$M). Slope gives mean slope in presence of cAMP. 2 mM Cs. Mean percent block of mBCNG-1 current by Cs. Second and third lines show standard errors and number of experiments for each measurement.

The steady-state voltage-dependence of activation was determined by hyperpolarizing the membrane to various test voltages (FIG. 16C). The relative magnitude of the decaying inward tail current upon return to the holding potential of −40 mV provides a measure of the fractional activation of the current during the preceding hyperpolarization. The peak tail current amplitudes show a sigmoidal dependence on the test voltage (FIG. 16D) They begin to activate at potentials negative to −80 mV and reach maximal activation with steps to between −110 and −120 mV. Fits of the Boltzmann equation to this relation (see Experimental Procedures) yield estimates of the voltage at which mBCNG-1 is half-maximally activated ($V_{1/2}$=−99.9±0.8 mV, n=5) as well as the slope of the relation between voltage and activation (e-fold change for −6.0±0.7 mV, n=5).

The mBCNG-1 current is carried by K and Na

Figure 17A:
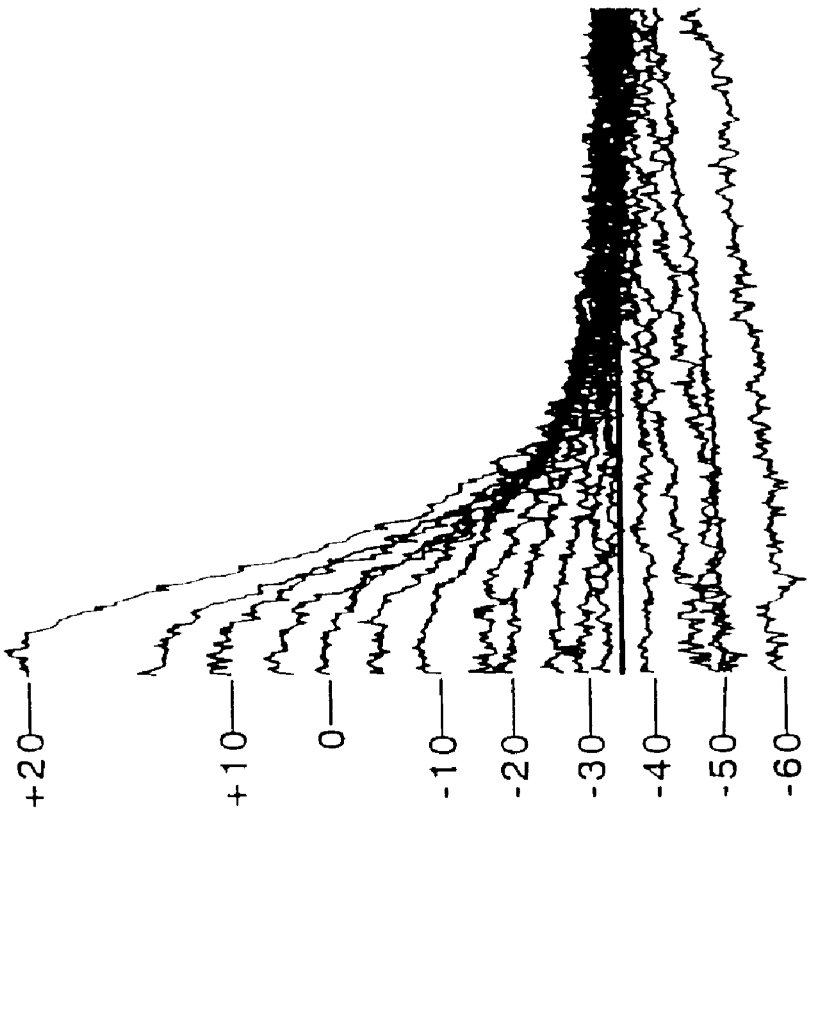
FIGS. 17A–17C. mBCNG-1 is a cation channel that selects weakly for potassium over sodium.
Figure 17B:
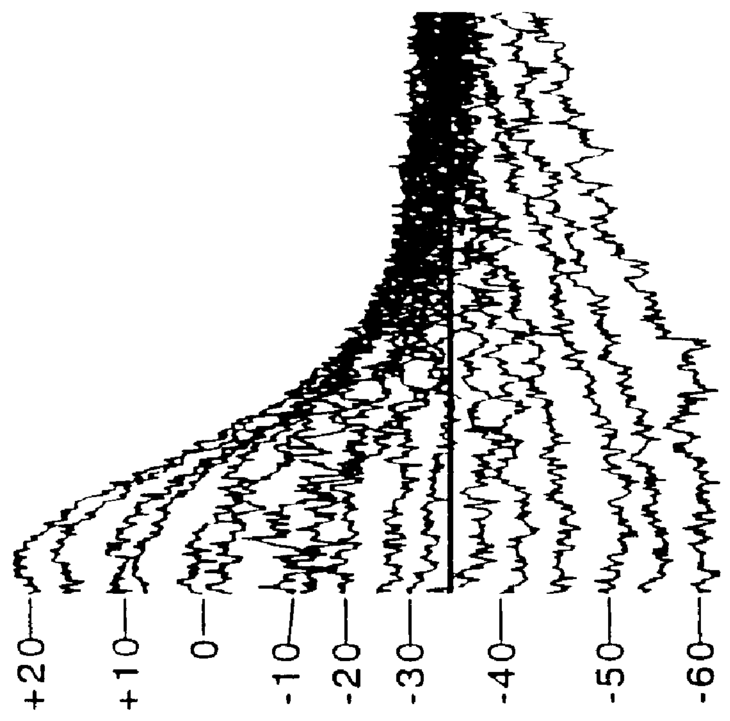
Figure 17C:
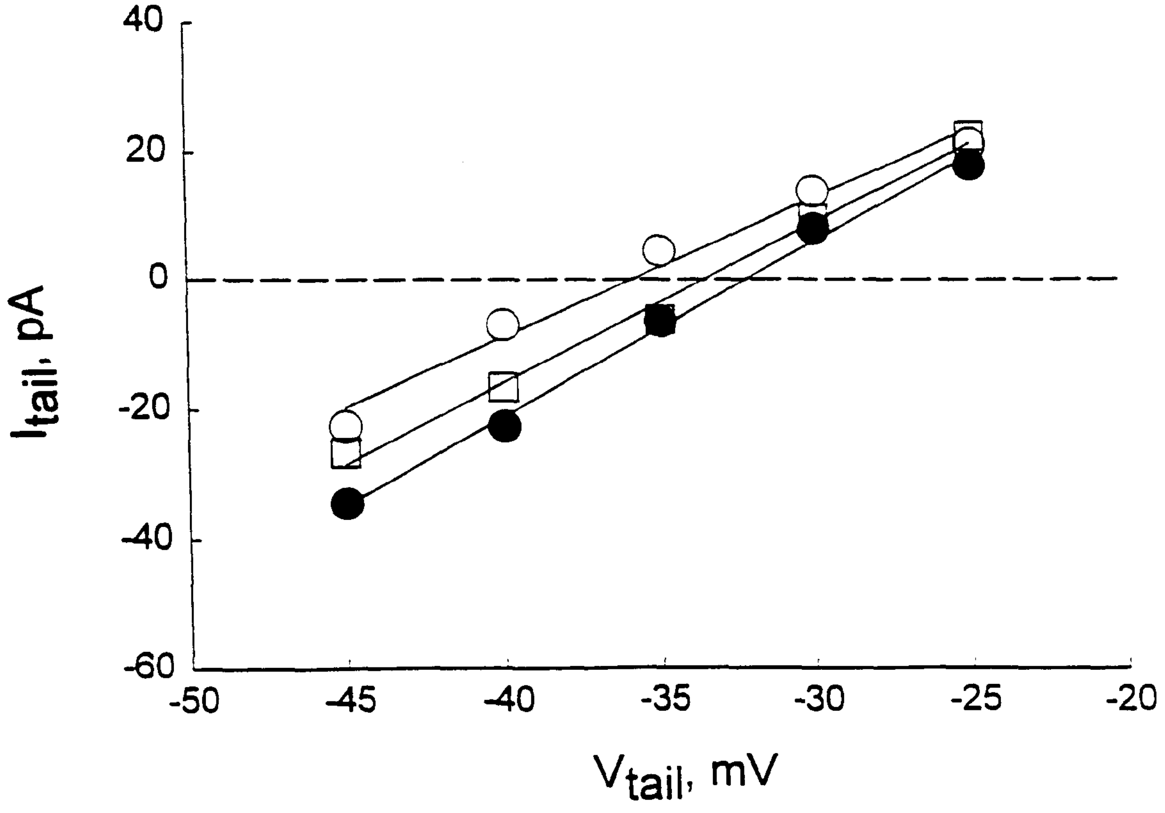

Native pacemaker channels are weakly selective for K over Na, exhibiting typical reversal potentials of around −30 mV under physiological gradients of Na and K. To demonstrate that the mBCNG-1 current is indeed mediated by cation-conducting channels, we measured the reversal potential of these currents under conditions of symmetrical Cl concentrations but asymmetric concentrations of K and Na that approximate their physiological gradients (FIGS. 17A, 17C). We find that the reversal potential of the mBCNG-1 current occurs at −31.8±1.6 mV (n=4), very close to the expected value (FIGS. 17A–C). As the above measurements were obtained in the absence of added Ca, we next explored the possibility that these channels may be converted to Ca-selective channels in the presence of external Ca, similar to voltage-gated calcium channels (Hess and Tsien, 1983). However, we found that addition of 1 mM Ca to the external NaCl solution did not cause any positive shift in the reversal potential (−34.9±3 mV, n=2), which would be expected for a Ca-selective channel. The reversal potential that we determined for the mBCNG-1 current is also clearly distinct from the value of 0 mV expected for a current carried by chloride ions. This point is important as Xenopus oocytes contain endogenous hyperpolarization-activated Cl channels whose level of expression can change upon expression of cRNAs (Tzounopolous et al., 1995). To further rule out a role for Cl, either as a charge carrier through mBCNG-1 channels or as a current that contaminates our measurements of mBCNG-1 currents, we replaced the internal Cl by aspartate, an anion which does not permeate most Cl channels. This is expected to shift the Cl equilibrium potential to −78 mV. Although Cl replacement altered the magnitude of the mBCNG-1 current (similar to that previously reported for the native $I_f$ channels—Frace et al., 1992), it did not cause a negative shift in the reversal potential (FIGS. 17B, 17C; there may be a small positive voltage shift that might be due to changes in liquid junction potential or K ion activity). It was thus concluded that mBCNG-1 does indeed code for a hyperpolarization-activated cation channel that is permeable to K and Na, similar to native $I_f$ and $_hI$ currents. Based on the measured reversal potential and the Goldman-Hodgkin-Katz equation, the channel is 4-fold more permeable to K than to Na, similar to the ratio in native pacemaker channels.

The mBCNG-1 current is blocked by external Cs but not by external Ba

Figure 18A:
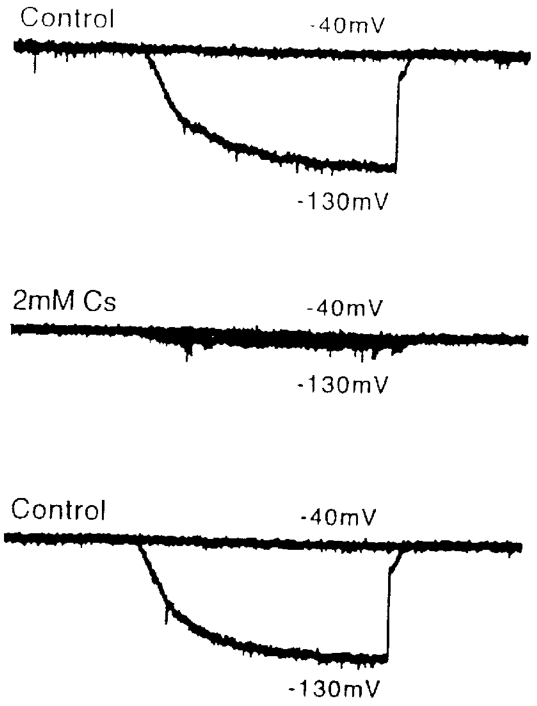
FIGS. 18A–18C. The mBCNG-1 channel is blocked by external Cs but not by external Ba, similar to native pacemaker channels. mBCNG-1 current records from an outside-out patch.
Figure 18B:
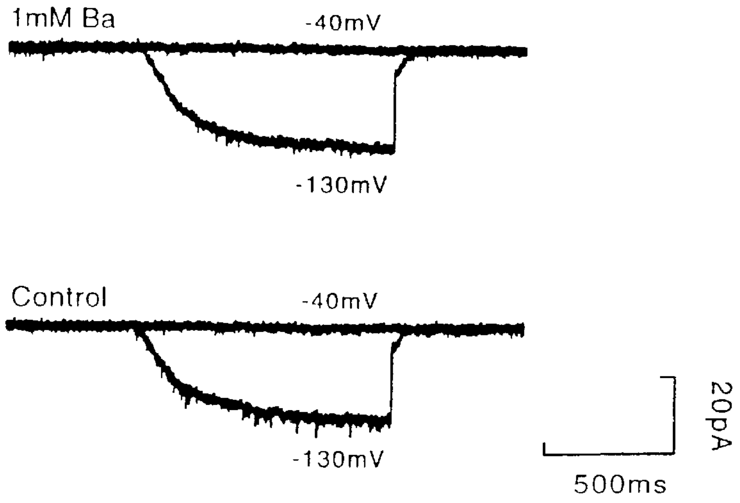
Figure 18C:
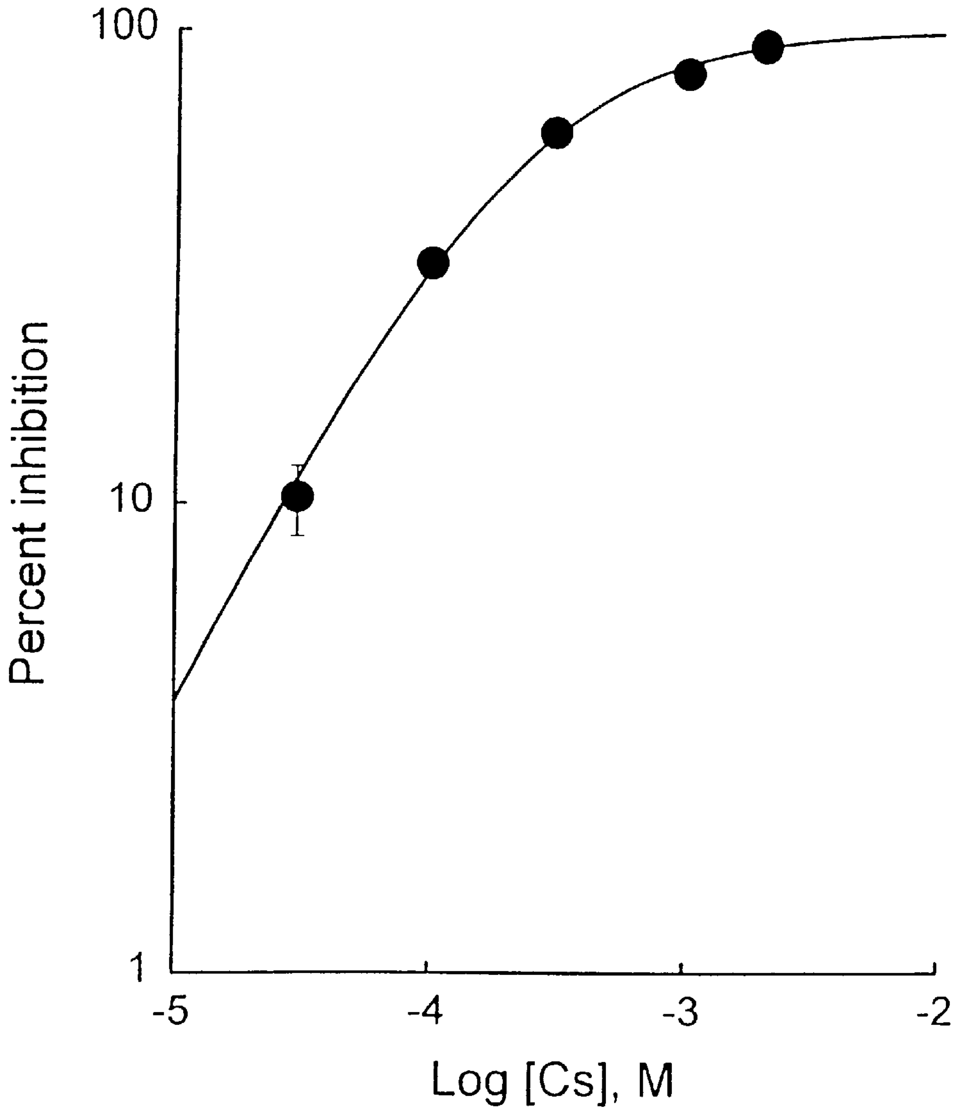

A characteristic feature of the pacemaker channel that allows it to be distinguished from several other types of hyperpolarization-activated channels is its sensitivity to block by relatively low concentrations of extracellular Cs (DiFrancesco, 1982; Noma et al., 1983). At the same time, the pacemaker channels are relatively insensitive to block by external Ba (DiFrancesco, 1982). We find that the mBCNG-1 channels are similar to native pacemaker channels in their sensitivity to external cations. Thus, the mBCNG-1 current is nearly completely blocked by 2 mM Cs ions when applied to the extracellular surface of an outside--out patch (FIGS. 18A–18B; mean % inhibition=92.4±2.5, n=6). Dose response curves for this effect show that the $IC_{50}$ is around 200 μM with a Hill coefficient of ~1 (FIG. 18C). In contrast to the blocking action of Cs, addition of 1 mM Ba to the external solution, which blocks inward rectifier K channels and hyperpolarization activated Cl channels, had little effect (FIGS. 18A–B; mean percent inhibition=0±5%, n=3). The fact that mBCNG-1 channels are largely blocked by Cs also indicates that our current measurements are not contaminated to any significant extent by endogenous oocyte Cl channels (Barish, 1983; Tzounopolous et al., 1995) or stretch-activated cation channels (Yang and Sachs, 1990), neither of which are blocked by external Cs.

mBCNG-1 channels are directly modulated by cAMP

Figure 19B:
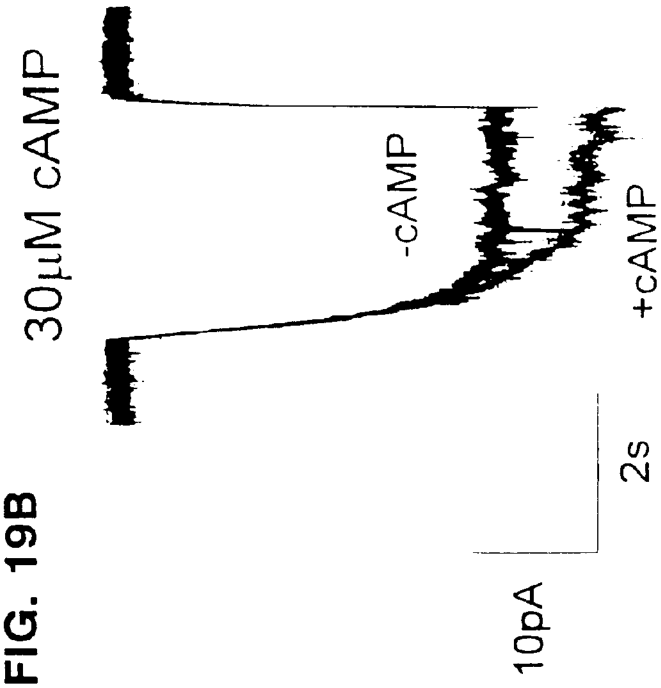
FIGS. 19A–19C. The mBCNG-1 channel is directly regulated by cytoplasmic cAMP.
Figure 19A:
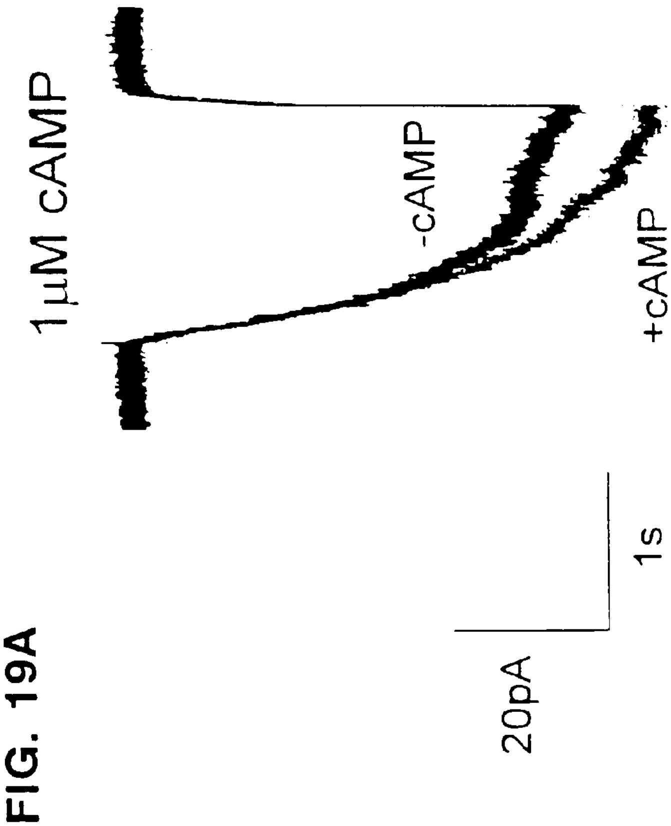
Figure 19C:
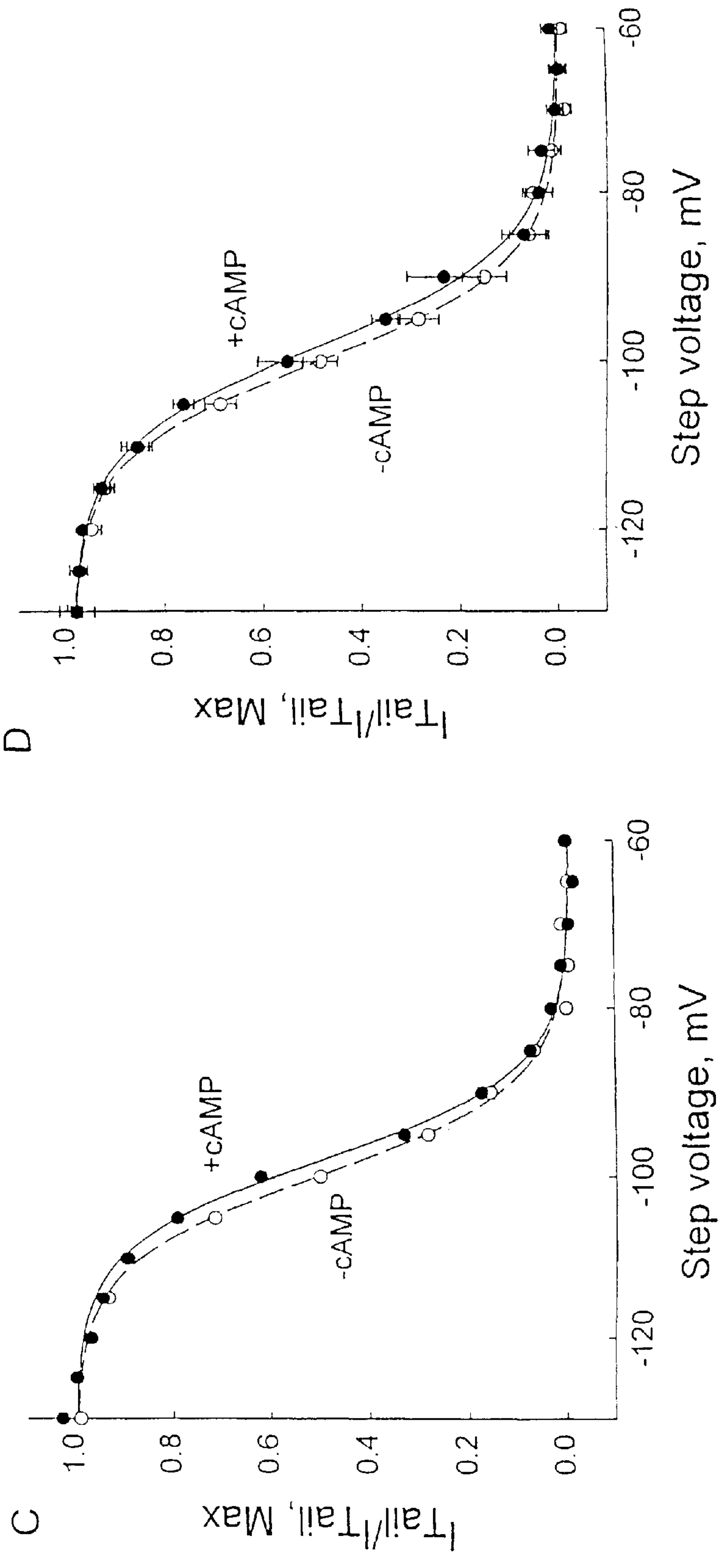

Previous studies on native pacemaker channels have shown that direct application of cAMP and/or cGMP to cell-free inside-out patches can increase the size of the $I_f$ current elicited by a submaximal hyperpolarization, due to a shift of the activation curve to more positive potentials (DiFrancesco and Tortora, 1991). We observed a qualitatively similar effect with the mBCNG-1 channels (FIGS. 19A–C). Thus, in resonse to bath application of cAMP to the internal surface of an inside-out patch, there is a reversible increase in the magnitude of the inward current during a step to 100 mV. The increase in current is observed in response to 1 μM, 30 μM or 3 mM cAMP (FIGS. 19A, 19B).

This effect of cAMP is due to a small, but reproducible, positive shift in the steady-state activation curve of these channels by 2 mV (FIG. 19C; mean=1.8±0.3 mV, n=5). Although this effect of cAMP is small, it was consistently observed in 5 out of 5 patches and found to be statistically significant (P<0.001; paired t-test). Moreover, in the four patches in which we could record full activation curves after washout of cAMP, the shift was shown to be reversible. The voltage shift is also observed when the individual activation curves from the 5 separate experiments are averaged to obtain the mean activation curves in either the absence or presence of cAMP (FIG. 19C). Although the averaging procedure tends to obscure the effects of cAMP due to small variability in the control activation curves among different patches, the difference between the curves is still significant (P<0.05; two way ANOVA with one repeated measure, F(3,6)=11.56). Furthermore, the shift we observe here with cAMP is nearly identical to the shift observed for pacemaker channels in the hippocampus (Pedarzani and Storm, 1995), a region where mBCNG-1 is highly expressed (Santoro et al., 1997). As there was no ATP or GTP in the internal solutions, G-AMP is likely to act by directly binding to the channels.

Based upon the above observations, we concluded that the hyperpolarization-activated current observed upon mBCNG-1 expression represents expression of a pacemaker channel with voltage-dependence, ionic selectivity, ionic blocking properties and second messenger modulation similar to the native brain pacemaker channels.

Identification of a family of BCNG genes

Since mBCNG-1 is expressed only in brain, we wondered whether other, related genes may be expressed in different tissues, including the heart. We have isolated partial cDNA clones for three additional mouse and two human genes encoding regions homologous to mBCNG-1. Partial cDNA clones representing two mouse genes (mBCNG-2 and mBCNG-3) were isolated while screening for full-length mBCNG-1 products, and a fourth mouse gene (mBCNG-4) as well as two human genes (hBCNG-1 and hBCNG-2) were identified following an EST database homology search, using the protein sequence of mBCNG-1 as a query. Further extensions of the identified cDNA clones were subsequently obtained by library screening or RT-PCR cloning. A schematic representation of the mouse and human BCNG sequences identified so far is presented in FIGS. 7A–7B.

Predicted amino acid sequence of the conserved BCNG channel family

The deduced, integrated, partial sequences obtained so far for the mBCNG-2, mBCNG-3 and mBCNG-4 encoded proteins are shown in FIGS. 8A–8B, and are tentatively aligned to the previously reported full length sequence of MBCNG-1 (Santoro et al., 1997). All of the identified sequences (except mBCNG-4) contain the conserved motifs of a voltage-gated potassium channel (Jan and Jan, 1997), including the S1–S6 transmembrane segments, a charged S4 voltage-sensor, and a pore-lining P loop. In addition, all BCNG family members contain a conserved cyclic nucleotide-binding domain in their carboxy terminus. It is interesting that both mBCNG-1 and mBCNG-2 contain a serine residue in their cytoplasmic carboxy terminus that lies within a consensus site for PKA phosphorylation (FIGS. 7*a*-7B, arrow) whereas mBCNG-4 does not contain this site. The absence or presence of the PKA site on different channels may explain why the cardiac Purkinje fiber channel is regulated by PKA phosphorylation (Chang et al., 1991) whereas the sinoatrial node channel is directly regulated by cAMP (DiFrancesco and Tortora, 1991).

The three mouse proteins are closely related to each other, having a similarity of 84–86% over the hydrophobic core region (amino acids 111 through 419, numbered according to mBCNG-1). Notably, mBCNG-2 and mBCNG-3 are more closely related to each other (89% similar) than either is to mBCNG-1. As far as a limited alignment could show, mBCNG-4 appears to be the most distantly related protein in the group (amino acids 529 through 592), having a similarity of 79% to mBCNG-1. The 308 amino acid-long core region of the hBCNG-1 protein, extending from the S1 through the S6 transmembrane segments, is 100% identical to mBCNG-1, while the core region of the hBCNG-2 protein is 98% similar to mBCNG-2.

Tissue distribution of BCNG mRNA expression

Northern blot analysis showed individual patterns of tissue distribution for each of the identified clones and a high correspondence in the transcript and localization patterns between homologous mouse and human clones (FIGS. 9A–9D and 10A–10D). The expression of mBCNG-1 appears to be largely restricted to the brain (FIGS. 9A–D; probe “q1”, see FIGS. 7A–7B), as previously reported using a distinct amino terminus probe (probe “q0”; Santoro et al. 1997). In contrast, mBCNG-2 and mBCNG-3 are expressed in the brain as well as in the heart (FIGS. 9A–D). Hybridization signals for mBCNG-3 are also detected in poly A+ RNA from skeletal muscle and lung. A distinct pattern of tissue distribution is revealed for mBCNG-4, which appears to be mainly expressed in the liver, but is also present in brain, lung and kidney (FIGS. 9A–D).

The homologous mouse and human BCNG genes are likely to be functionally similar since they exhibit very similar patterns of tissue expression as revealed by Northern blot analysis. FIGS. 10A–D shows that a probe designed within the hBCNG-1 sequence recognized four transcripts in human brain polyA+ RNA, similar to that seen in the mBCNG-1 Northern blot (FIGS. 9A–9D and Santoro et al. 1997). Weak hybridization signals are also detected for hBCNG-1 in human muscle and pancreas. Northern blot analysis using a probe based on the hBCNG-2 sequence showed an expression pattern which is highly consistent with the expression pattern of mBCNG-2 (FIGS. 10A–D; compare with FIGS. 9A–9D). An abundant 3.4 kb transcript is detected in the brain and the same transcript is also present in the heart.

The analysis of the distribution of mBCNG-1 within the mouse brain (Santoro et al. 1997) revealed that the highest expression of mBCNG-1 occurs in the cortex, hippocampus and cerebellum. Northern blot analysis of the hBCNG-1 mRNA distribution within different brain regions also showed a differential expression of the gene, with the highest levels present in cortical structures (hippocampus and amygdala; FIGS. 10A–D). hBCNG-2 shows a more uniform level of high expression in all brain structures, suggesting a more ubiquitous role. In particular, the strong hybridization signal in corpus callosum-derived RNA may indicate expression of hBCNG-2 within glial cells.

Figure 20A:
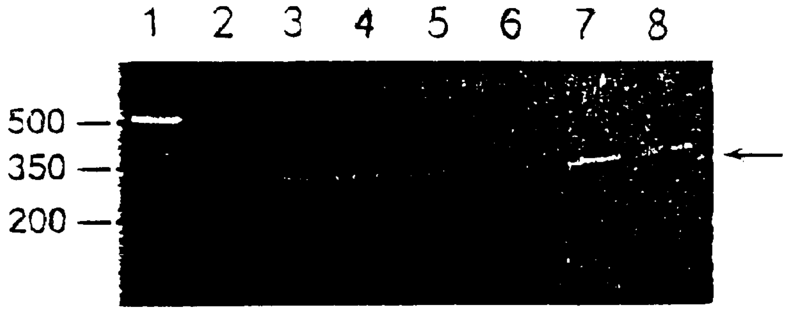
FIG. 20A. PolyA+ RNA samples from ventricle, atrial and sino-atrial node of the rabbit heart were tested by RT-PCR for the presence of mBCNG-2 or 3 transcripts. Lanes: 1) molecular weight marker; 2) reaction performed in the absence of reverse transcriptase; 3) ventricle RNA; 4) atrial RNA; 5) sino-atrial node RNA; 6) PCR reaction on plasmid containing mBCNG-1 cDNA; 7) PCR reaction on plasmid containing mBCNG-2 cDNA; 8) PCR reaction on plasmid containing mBCNG-3 cDNA. Molecular size markers are indicated on the left. The arrow on the right indicates the expected 340 bp amplification product.
Figure 20B:
FIG. 20B. Southern blot analysis of the gel shown in A using a probe to mBCNG-2.
Figure 20C:
FIG. 20C. Southern blot analysis of the gel in A using a probe to mBCNG-3.

If the BCNG-2 and BCNG-3 genes expressed in heart do indeed code for pacemaker channels, we would expect them to be expressed in the cardiac tissues in which pacemaker channel activity has been reported. Although the sinoatrial node is the primary pacemaking tissue of the heart, latent pacemaker activity is found in both atrial (Thuringer et al., 1992; Zhou et al., 1992) and ventricular (Yu et al., 1993; Robinson et al., 1997) muscle. However, the voltage-dependence of activation of the channels in the regions outside of the node is normally shifted to very hyperpolarized, non-physiological potentials. In accord with this observation of a widespread occurrence of pacemaker channels throughout the heart, we find that primers which amplify both mBCNG-2 and mBCNG-3, but not mBCNG-1, generate RT-PCR products from ventricular, atrial and sinoatrial node mRNA (FIG. 20A). To establish the relative expression of mBCNG-2 and mBCNG-3 within each of these regions of the heart, we performed a Southern blot analysis on the RT-PCR products. Hybridization with probes that specifically recognize mBCNG-2 or mBCNG-3 demonstrate that the predominant species within the RT-PCR product, and hence the analyzed cardiac regions, is mBCNG-2 (FIGS. 20B, C).

Discussion

Identification of a pacemaker channel gene for brain

The distinct sequences and tissue distributions of the identified BCNG genes reveals that the BCNG products represent a family of ion channel proteins, with characteristic motifs for voltage-sensing and cyclic nucleotide-binding. These genes are predominantly located in brain and in heart. When expressed in Xenopus oocytes, the mBCNG-1 channel gives rise to a hyperpolarization-activated cation channel whose properties closely correspond to those of the pacemaker current in the heart ($I_f$). Although we have no direct evidence that the members of the BCNG channel family expressed in heart code for cardiac pacemaker channels, the tissue distribution and sequence similarity of these partial cDNA clones with full-length mBCNG-1 is suggestive that they may well code for the cardiac channel.

Members of the voltage-gated K channel family are generally tetramers, composed of four pore-forming subunits (MacKinnon, 1991). Although mBCNG-1 cRNA leads to expression of functional channels on its own, the existence of multiple BCNG genes suggests that the native channels may be heteromultimers. In addition, the BCNG channel subunits may associate with auxiliary, non-pore-forming β subunits that modify the function of the channel. It is possible that mBCNG-1 may be more potently modulated by cAMP when it combines with additional subunits.

Alternatively, there may be inherent differences in the efficacy with which cAMP modulates different BCNG family members. In support of this latter possibility, the cAMP-dependent shift of Ih in hippocampal neurons, where BCNG-1 is prominently expressed (FIGS. 10A–D, and Santoro et al., 1997), is only 2–3 mV (Pedarzani and Storm, 1995), almost identical to the shift observed here. This contrasts with the 10 mV shift reported for $I_f$ in sino-atrial node (DiFrancesco and Tortora, 1991) and the 4–6 mV shift of $I_h$ in sensory neurons (Ingram and Williams, 1966). The relatively rapid activation kinetics of mBCNG-1 also make it more simlar to the rapidly activated hippocampal channel (Halliwell and Adams, 1982; Maccaferri et al., 1993; Pedarzani and Storm, 1995) than to the more slowly activating cardiac channels. It is an intriguing possibility that differences in cAMP efficacy may be related to the phosphorylation state of the serinve residue in the PKA consensus site within the cyclic nucleotide binding domain of the BCNG-1 and BCNG-2 subunits.

Two important differences from classic voltage-gated channels endow the mBCNG-1 channel with its characteristic properties Despite the sequence similarity between the BCNG channels and other voltage-gated K channels, there are two important functional differences. First, most voltage-gated K channels are usually activated by depolarization. The opposite voltage-dependent polarity of the mBCNG-1 channels occurs despite the presence of a highly charged, basic S4 voltage-sensing domain. Second, whereas most members of the K channel family are at least 100-fold selective for K ions over Na ions, the mBCNG-1 channels, like the native pacemaker channels, are only four fold selective for potassium versus sodium. The BCNG channels do, however, contain a P region that is similar to P regions of other K selective channels. We discuss possible mechanisms for these differences below.

How can the BCNG channels activate upon membrane hyperpolarization rather than depolarization, despite the presence of an S4 segment? A similar reversed polarity of voltage-dependent activation has been reported for the S4-containing KAT1 voltage-gated potassium channel of plants (Schachtman et al., 1994). One relatively simple mechanism that can explain the voltage-gating properties of KAT1 and mBCNG-1 channels is provided by the study of Miller and Aldrich (1996) on Shaker K channels, which normally activate rapidly and then inactivate rapidly upon depolarization. These authors showed that S4 point mutations that shift the activation gating reaction to very negative potentials (well below the resting potential) transformed the Shaker K channels into hyperpolarization-activated channels. At voltages near the resting potential, even though the activation gates of the mutant channels are in the open configuration, the channels are closed due to the inactivation reaction. Moderate hyperpolarizations, that are not sufficiently negative to shut the activation gates, open the channels by causing inactivation gates to open. The opening of the BCNG channels upon hyperpolarization could reflect a similar removal of inactivation.

The lower K selectivity of the mBCNG-1 channels could reflect the presence of several non-conservative changes at key positions in the P region. Thus, although the channels do contain the GYG motif that forms the major part of the K channel selectivity sequence, a conserved threonine residue two residues N terminal to the GYG triplet is changed to a cysteine in the BCNG channels. This conserved threonine has been shown to form part of the K selectivity filter in the X-ray crystal structure of the bacterial kcsa channel (Doyle et al., 1998). Moroever, a highly conserved aspartate (immediately C terminal to the GYG triplet) is either an alanine or arginine in the BCNG clones.

The role of the pacemaker current in disease

Might changes in BCNG channel function due to post-translational modification, changes in gene expression, or genetic mutations underlie inherited or acquired neurological disorders or diseases of automaticity? With our identification that the BCNG genes code for CNS and, perhaps, cardiac pacemaker channels, it should now be possible to determine whether certain familial sinus rhythm diseases (Spellberg, 1971) are due to primary defects in the pacemaker channel. Defects in pacemaker channel function could also contribute to acquired diseases of the heart, such as sick sinus syndrome associated with atrial fibrillation, sinus tachycardias and bradycardias (Bigger and Reiffel, 1979), and ventricular arrhythmias associated with heart failure (Cerbai et al., 1994; 1997).

The existence of multiple genes coding for regionally specific channels offers the intriguing possibility of developing therapeutic agents that would specifically target, for example, cardiac rather than brain pacemaker channels. Conversely, the importance of pacemaker activity in the brain for arousal and perhaps perceptual awareness might make these brain channels interesting targets for pharmacological manipulation. Finally, controversies as to the precise role of the pacemaker channels in the electrical activity of both the brain and heart should now be amenable to the powerful approaches of mouse genetics.

Experimental Procedures

Library screening and RT-PCR cloning

Standard manipulations of Escherichia coli, lambda phage and nucleic acids, including recombinant DNA procedures, were performed essentially as described (Sambrook et al. 1989).

The first fragment of mBCNG-2 cDNA was cloned as a product of PCR reactions designed to isolate full length mBCNG-1 cDNA (Santoro et al., 1997). This fragment corresponded to 234–430 of the mBCNG-2 sequence (numbering here and througout according to mBCNG-1, see FIGS. 8A–8B) and was used to screen a mouse brain λgt10 library (CLONTECH® ML 3000a) at hight stringency, yielding the N-terminal part of mBCNG-2 (clone 11-λ1). From the same λgt10 library screen, a weakly reacting plaque was also identified (clone 15-7), which was subsequently shown to represent a third distinct gene (mBCNG-3).

A BLAST search in mouse and human EST databases revealed four EST clones that appeared to be fragments of two mouse BCNG genes (M41-EST, gb AA023393; M28-EST, gb AA238712) and two human BCNG genes (H57-EST, gb H45591; H61-EST, gb N72770). Oligonucleotides were designed within these sequences and used together with oligonucleotides designed in conserved regions of the BCNG clones to obtain RT-PCR products from mouse or human polyA+ RNA (see below). RT-PCR products were sequenced and the overlapping regions compared, to establish the correspondence between ESTs and known BCNG clones (see FIG. 5). The M28-EST clone appeared to represent a fourth and distinct gene from the previously identified BCNG cDNAs. Complete sequencing of the M28-EST clone revealed that only the 31 end of the clone aligns with the BCNG sequences; the sequence 5' to position 632 is likely to represent an intron, and a stop codon is present at position 869.

A human brain λgt10 library (CLONTECH®, HL 3022a) was screened with a fragment derived from H61-EST clone (probe "H61"); see below, and FIGS. 7A–C), yielding the N-terminal region of the hBCNG-2 sequence up to amino acid at position number 587.

RT-PCR reactions were performed (25 times for 45 sec at 94° C., 30 sec at 55° C., and 2 min at 72° C.) on polyA+ RNA preparations from mouse brain and mouse heart (CLONTECH®, 6616-1 and 6611-1), using the SuperScript Preamplification System (GIBCO-BRL®) with the following oligonucleotides:

B123 5'CAGTGGGAAGAGATTTTCCACATGACC3' (Seq I.D. No. 23) (corresponding to aa 269–277) and 41REV 5'GATCATGCTGAACCTTGTGCAGCAAG3' (Seq. I.D. No. 24) (corresponding to aa 590–598) or 28REV 5'CACCKCRTTGAAGTGGTCCACGCT3' (Seq I.D. No. 25) (corresponding to aa 554–561).

For human genes, reactions were performed (25 times for 45 sec at 94° C., 20 sec at 58° C., and 3 min at 72° C.) on polyA+ RNA from human brain and human heart (CLONTECH®, 6516-1 and 6533-1) using the following oligonucleotides:

MB1–3 5'ATGTTCGGSAGCCAGAAGGCGGTGGAG3' (Seq I.D. No. 26) (corresponding to aa 102–110) and H57.C 5'CAGCTCGAACACTGGCAGTACGAC3' (Seq I.D. No. 27) (corresponding to aa 537–544).

For heart region localization of BCNG-2/3 transcripts, reactions were performed on polyA+ RNA isolated from ventricles, atria or sinoatrial nodes of rabbit heart, using oligonucleotides:

BCNG-2/F2 5'GAGCAGGAGCGCGTCAAGTCGGCG3' (Seq I.D. No. 28) (corresponding to aa 112–119) and BCNG-2/R2 5'GAAGATGTAGTCCACGGGGATGGA3' (Seq I.D. No. 29) (corresponding to aa 218–225).

Figure 9A:
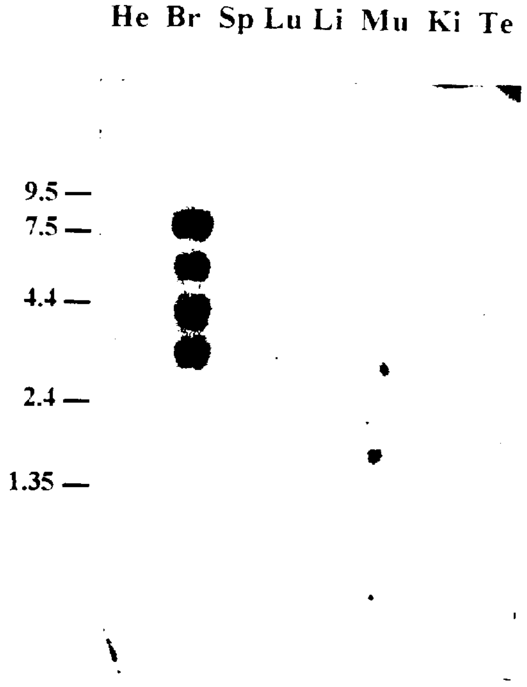
FIGS. 9A–9D. Northern Blot Analysis of Mouse BCNG Gene Expression. Multiple Tissue Northern blot, containg 2 μg of polyA+ RNA from each of the following mouse tissues: heart (He), brain (Br), spleen (Sp), lung (Lu) liver (Li), skeletal muscle (Mu), kidney (Ki) and testis (Te), was hybridized to DNA fragments corresponding to the indicated BCNG genes. Molecular size markers are indicated on the left.
Figure 9B:
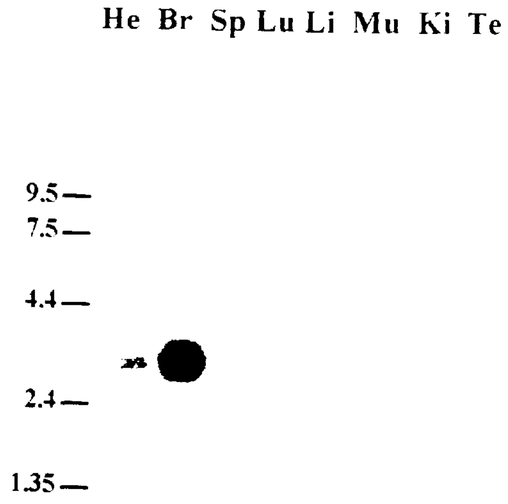
Figure 9C:
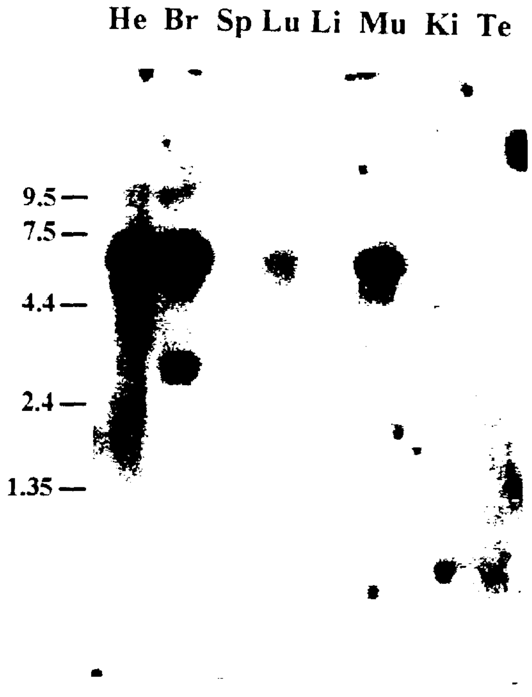
Figure 9D:
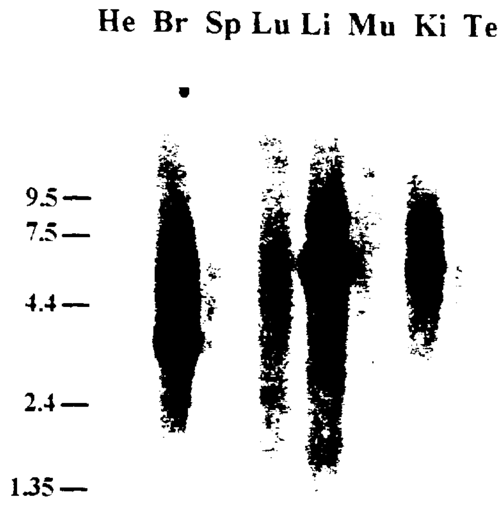
Figure 10A:
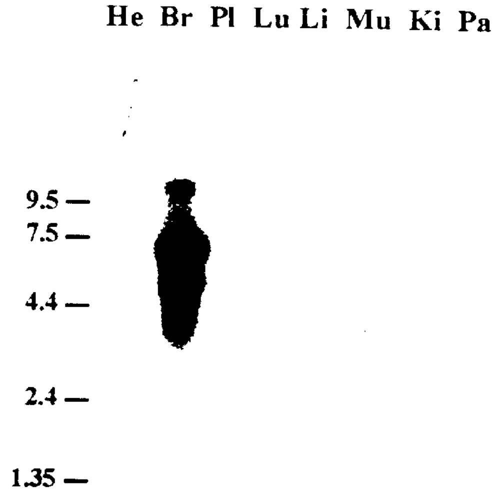
FIGS. 10A–D. Northern Blot Analysis of Human BCNG Gene Expression.
Figure 10B:
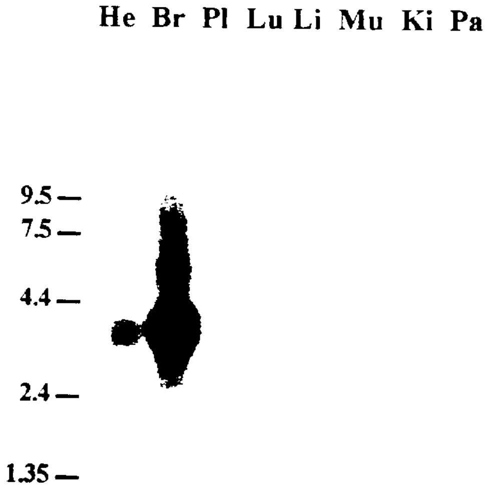
Figure 10C:
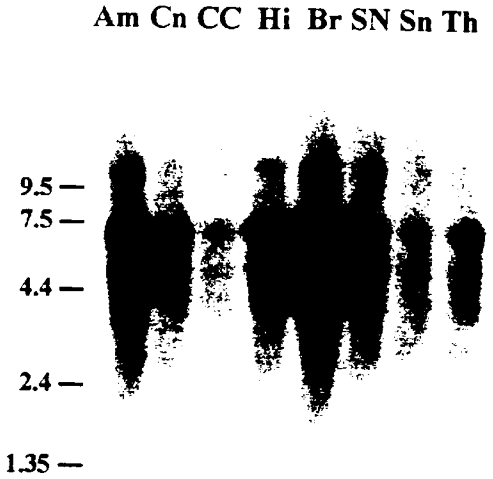
Figure 10D:
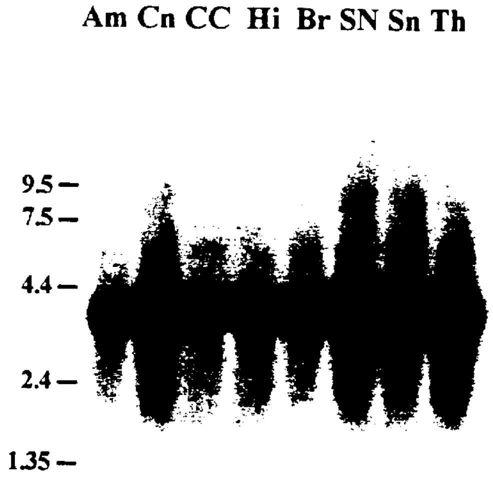

To determine the specificity of recognition among different family members, the same oligonucleotides were used on plasmid DNAs that encoded mBCNG-1, 2 or 3 cDNAs (see Legend to FIG. 9A). These plasmids were labeled by random priming (STRATAGENE®) and used as the probes for the Southern blot analysis.

Northern Blots

For mouse gene expression studies, a mouse multiple tissue Northern blot (CLONTECH®, 7762-1) was probed with PCR products representing the following regions of the mBCNG clones (see schematic representation in FIGS. 7A–7B and amino acid numbering in FIGS. 8A–8B):

mBCNG-1: probe "q1" (corresponding to aa 594–720; Santoro et al., 1997); mBCNG-2: probe "dA" (corresponding to aa 234–430). mBCNG-3: probe "115-7" (corresponding to the mBCNG-3 sequence from start up to position 319). mBCNG-4: probe "M28" (corresponding to aa 529–607 of the mBCNG-4 sequence plus 180 nt of the mBCNG-4 3' UTR; this probe was obtained as a gel-purified EcoRI/BglII restriction fragment, 400 bp, from the EST-M28 DNA).

For human gene expression studies, a human multiple tissue Northern blot (CLONTECH®, 7760-1) or human brain multiple tissue Northern blot (CLONTECH, 7750-1) was probed with the following PCR products:

hBCNG-1: probe "H57" (corresponding to aa 537–800). hBCNG-2: probe "H61" (corresponding to aa 452–634). Hybridizations were all performed in EXPRESSHYB® solution (CLONTECH®) for 1 hr at 68° C., as indicated in the manufacturer's Protocol Handbook. Blots were washed for 10 min at room temperature in 2x SSC/0.1% SDS, followed by two washes for 30 min at 65° C. in 0.2x SSC/0.1% SDS. Filters were stripped between subsequent hybridizations by boiling for 5 min in 0.5% SDS/H20.

Electrophysiological recordings mBCNG-1 was subcloned into the pSD64TR expression vector. RNA was transcribed from BamHI-linearized DNA using SP6 RNA polymerase (Message Machine®, Ambion®) and injected into Xenopus oocytes prepared as previously described (Goulding et al., 1992).

Patch clamp recordings were made from cell-free inside-out and outside-out patches 3–7 days after cRNA injection. Data were acquired using either an Axopatch 200A or 200B integrating patch clamp amplifier (Axon Instruments®, USA). The holding potential in all of these experiments was −40 mV. For simplicity, only abbreviated descriptions of the solutions used are given in the text and in Brief Description of the Figures, full descriptions are given below.

The KC1-EGTA solution contained: 107 mM KCl, 5 mM NaCl, 10 mM HEPES (pH 7.4, KOH), 1 mM EGTA. The NaCl-EGTA solution contained 107 mM NaCl, 5 mM KCl, 10 mM HEPES (pH 7.4, NaOH), 1 mM EGTA. The KCl/NaCl-EGTA and KCl/NaCl-CaCl2 solutions contained: 82 mM KCl, 30 mM NaCl, 10 mM HEPES (pH 7.4, KOH) with either 1 mM EGTA or 1 mM CaCl2, respectively. In some experiments we replaced Cl with aspartate in the following KAspartate-EGTA solution: 107 mM K-Aspartate, 5 mM NaCl, 10 mM HEPES (pH 7.4, KOH), 1 mM EGTA. Where appropriate, Na-cAMP was included in the intracellular solution by iso-osmolar replacement of NaCl, while CsCl and BaCl2 were included in the indicated extracellular solutions by iso-osmotic replacement of NaCl or CaCl2, respectively. A Ag-AgCl ground wire was connected to the bath solution by a 3 M KCl agar bridge electrode. The largest uncompensated junction potential was measured to be 3.4 mV. Voltages have not been corrected to account for this offset. All recordings were obtained at room temperature (22–24° C.).

Voltage clamp protocols were applied using a P/N protocol to subtract uncompensated linear leak and capacitance using either pClamp® software (v 6.0, AXON INSTRUMENTS®, with N=8) and a Pentium 100 mHz PC computer or the Pulse software (v 8.11, Heka, with N=10) and a MACINTOSH CENTRIS® 650 computer. Unless otherwise indicated, data were low pass filtered at 1.25 kHz (8 pole Bessel filter, Frequency Devices 902) and digitized at 2.5 kHz using either a TL-1 DMA Interface (AXON INSTRUMENTS®) or an ITC-16 interface (INSTRUTECH CORP.®). Analyses were done using pClamp (v 6.0, AXON INSTRUMENTS®), Pulse (v 8.11, Heka) or Sigmaplot (v 4.0 SPSS Inc.).

The current-voltage relationship was obtained by measuring steady-state current values at the end of 3 s voltage steps (current averaged between 2.5 s to 2.95 s) The steady-state activation curve was determined from the amplitude of tail currents observed upon a subsequent depolarizing voltage step to −40 mV (current averaged between 4–10 ms following the return to −40 mV). Current values were plotted versus the hyperpolarization step voltage and fitted with the Boltzmann equation:

$$I(V)=A_1+A_2/\{1+\exp[-(V-V_{1/2})/\text{slope}]\}$$

where $A_1$ is the offset, $A_2$ the amplitude, V is voltage in mV and $V_{1/2}$ is the activation mid-point voltage. The data and the fitted Boltzmann function were then normalized to the maximum amplitude of the fit. Activation time constants were determined by fitting single exponentials to the rising phase of the current after allowing for an initial lag.

To determine reversal potentials under different ionic conditions, inside-out patches held at −40 mV were stepped to −130 mV for 300 ms and then stepped back to a series of test potentials ranging from −60 to +20 mV in 5 mV increments. The peak amplitude of the tail currents were measured by averaging the data between 2 and 4 ms following the step to the test potential. The sensitivity of the mBCNG-1 current to external Cs and Ba was determined using the outside-out patch clamp configuration and measuring the steady-state current values at the end of 1 s steps to −130 mV (current averaged between 800 ms to 990 ms). In both of these series of experiments, electrodes were coated with Sylgard to minimize pipette capacitance, and data were filtered at 2.5 kHz and sampled at 5 kHz.

Contamination from an endogenous Ca-activated Cl channel in the oocyte membrane (Barish, 1983) was minimized by including EGTA (1 mM) with no added calcium in the internal solution. Oocytes also contain a stretch-activated cation channel that can be recognized by its large single channel conductance (60 pS) (Yang and Sachs, 1990). Patches containing such channel activity were not studied.

EXAMPLE 5

Co-expression of BCNG channel subunits and candidate proteins.

BCNG proteins or BCNG-related proteins may form heteromultimeric proteins. In order to delineate the functional roles of novel BCNG subunits, novel BCNG subunits are coexpressed with BCNG subunits that have overlapping tissue distribution. Voltage-gated $K^+$ channels and cyclic nucleotide-gated channels both form heteromultimers. In some cases, the subunits can form complexes with completely distinct proteins (eg. KvLQT1 with MinK—(Barhanin, et al., 1996; HERG with MinK McDonald, et al., 1997); IrK6.1 and IrK6.2 with the sulphonylurea receptor—Isomoto, et al., 1996; Inagaki, et al., 1996). BCNG proteins may assemble with subunits such as MinK or ERG like subunits. Candidate proteins are selected on the basis of overlapping tissue distribution and likelihood based on known functional properties. For example, Kv1.2 shows overlapping distribution with mBCNG-1 even at the subcellular level (Sheng, et al., 1994; Wang, et al., 1994).

Coexpression with polvA+ MRNA. If another protein can form a functional heteromultimer with the BCNG channel proteins, co-expression with size fractionated mRNA from tissue (eg. heart, brain, muscle or kidney) where the appropriate BCNG subunit is expressed (as shown by Northern blot analysis) should result in a unique current in electrophysiological currents when the BCNG RNA is coinjected with the mRNA from the tissue.

Alternative strategies to clone subunits that will modify functional properties of the expressed BCNG channels include low stringency homology screening of appropriate libraries using nucleotide probes derived from BCNG genes or PCR amplification from genomic or cDNA using degenerate oligonucleotides based on BCNG genes.

Yet another method to isolate other channel subunit proteins that may coassemble with identified BCNG family members is to use the yeast two hybrid system (Fields and Soug, 1989). This system was initially used to clone mBCNG-1 based on its interaction with the n-src SH3 domain (See, Example 1). Conserved cytoplasmic N- and C-terminal domains from BCNG channel proteins are used as the 'bait' in the yeast two hybrid system. N- and C-terminal fragments are subcloned in an appropriate plasmid (e.g. pEG202) (Zervos et al., 1983).

Sequences of BCNG family members: DNA and Predicted Amino Acid Sequences of Mouse and Human BCNG Clones Mouse sequences DNA and predicted amino acid sequence of mBCNG-1

These mouse sequences are the original DNA and predicted amino acid sequences obtained and are those in GenBank Accession Number AF028737.

mBCNG-1 DNA open reading frame (SEQ ID NO:30)

```
ATGGAAGGCGGCGGCAAACCCAACTCCGCGTCCAACAGCCGCGACGATGG
CAACAGCGTCTTCCCCTCCAAGGCGCCCGCGACGGGGCCGGTGGCGGCCG
ACAAGCGCCTGGGGACCCCGCCGAGGGGCGGCGCGGCCGGGAAGGAACAT
GGCAACTCCGTGTGCTTCAAGGTGGACGGCGGCGGAGGAGAGGAGCCGGC
GGGCAGCTTCGAGGATGCCGAGGGGCCCCGGCGGCAGTATGGTTTCATGC
AGAGGCAGTTCACCTCCATGCTGCAGCCTGGGGTCAACAAATTCTCCCTC
CGCATGTTTGGGAGCCAGAAGGCGGTGGAGAAGGAGCAGGAAAGGGTTAA
AACTGCAGGCTTCTGGATTATCCATCCGTACAGTGACTTCAGGTTTTATT
GGGATTTAATCATGCTTATAATGATGGTTGGAAATTTGGTCATCATACCA
GTTGGAATCACGTTCTTCACAGAGCAGACGACAACACCGTGGATTATTTT
CAACGTGGCATCCGATACTGTTTTCCTGCTTGGACTTAATCATGAATTTT
AGGACTGGGACTGTCAATGAAGACAGCTCGGAAATCATCCTGGACCCTAA
AGTGATCAAGATGAATTATTTAAAAAGCTGGTTTGTGGTGGACTTCATCT
CATCGATCCCGGTGGATTATATCTTTCTCATTGTAGAGAAAGGGATGGAC
TCAGAAGTTTACAAGACAGCCAGAGCACTTCGTATCGTGAGGTTTACAAA
AATTCTCAGTCTCTTGCGGTTATTACGCCTTTCAAGGTTAATCAGATACA
TACACCAGTGGGAAGAGATATTCCACATGACCTATGACCTCGCCAGTGCT
GTGGTGAGGATCTTCAACCTCATTGGCATGATGCTGCTTCTGTGCCACTG
GGATGGCTGTCTTCAGTTCCTGGTTCCCCTGCTGCAGGACTTCCCACCAG
ATTGCTGGGTTTCTCTGAATGAAATGGTTAATGATTCCTGGGGAAAACAA
TATTCCTACGCACTCTTCAAAGCTATGAGTCACATGCTGTGCATTGGTTA
TGGCGCCCAAGCCCCTGTCAGCATGTCTGACCTCTGGATTACCATGCTGA
GCATGATTGTGGGCGCCACCTGCTACGCAATGTTTGTTGGCCATGCCACA
GCTTTGATCCAGTCTTTGGACTCTTCAAGGAGGCAGTATCAAGAGAAGTA
TAAGCAAGTAGAGCAATACATGTCATTCCACAAGTTACCAGCTGACATGC
GCCAGAAGATACATGATTACTATGAGCACCGATACCAAGGCAAGATCTTC
GATGAAGAAAATATTCTCAGTGAGCTTAATGATCCTCTGAGAGAGGAAAT
AGTCAACTTCAACTGCCGGAAACTGGTGGCTACTATGCCTCTTTTTGCTA
ACGCCGATCCCAATTTCGTGACGGCCATGCTGAGCAAGCTGAGATTTGAG
GTGTTCCAGCCCGGAGACTATATCATTCGAGAAGGAGCTGTGGGGAAGAA
```

-continued

AATGTATTTCATCCAGCACGGTGTTGCTGGCGTTATCACCAAGTCCAGTA
AAGAAATGAAGCTGACAGATGGCTCTTACTTCGGAGAGATATGCCTGCTG
ACCAAGGGCCGGCGCACTGCCAGTGTCCGAGCTGATACCTACTGTCGTCT
TTACTCCCTTTCGGTGGACAATTTCAATGAGGTCTTGGAGGAATATCCAA
TGATGAGAAGAGCCTTTGAGACAGTTGCTATTGACCGACTCGATCGGATA
GGCAAGAAAAACTCTATTCTCCTGCAGAAGTTCCAGAAGGATCTAAACAC
TGGTGTTTTCAACAACCAGGAGAACGAGATCCTGAAGCAGATCGTGAAGC
ATGACCGAGAGATGGTACAAGCTATCCCTCCAATCAACTATCCTCAAATG
ACAGCCCTCAACTGCACATCTTCAACCACCACCCCAACCTCCCGCATGAG
GACCCAATCTCCGCCAGTCTACACCGCAACCAGCCTGTCTCACAGCAATC
TGCACTCACCCAGTCCCAGCACACAGACGCCCCAACCCTCAGCCATCCTT
CACCCTGCTCCTATACCACAGCAGTCTGCAGTCCTCCTATACAGAGCCCC
CTGGCCACACGAACTTTCCATTATGCCTCTCCCACTGCGTCCCAGCTGTC
ACTCATGCAGCAGCCTCAGCAGCAACTACCGCAGTCCCAGGTACAGCAGA
CTCAGACTCAGACTCAGCAGCAGCAGCAGCAACAGCAGCAGCAGCAGCAG
CAGCAACAGCAACAACAGCAGCAGCAGCAGCAGCAGCAGCAGCAGCAGCA
GCAGCAGCAGCAGCAGCAGCAGCAGCCACAGACACCTGGTAGCTCCACAC
CGAAAAATGAAGTGCACAAGAGCACACAAGCCCTTCATAACACCAACCTG
ACCAAAGAAGTCAGGCCCCTTTCCGCCTCGCAGCCTTCTCTGCCCCATGA
GGTCTCCACTTTGATCTCCAGACCTCATCCCACTGTGGGCGAATCCCTGG
CCTCTATCCCTCAACCCGTGGCAGCAGTCCACAGCACTGGCCTTCAGGCA
GGGAGCAGGAGCACAGTGCCACAACGTGTCACCTTGTTCCGACAGATGTC
CTCGGGAGCCATCCCCCCCAACCGAGGAGTGCCTCCAGCACCCCCTCCAC
CAGCAGCTGTGCAGAGAGAGTCTCCCTCAGTCCTAAATACAGACCCAGAT
GCAGAAAAACCCCGTTTTGCTTCGAATTTATGA mBCNG-1 predicted amino acid sequence (SEQ ID NO:31)
MEGGGKPNSASNSRDDGNSVFPSKAPATGPVAADKRLGTPPRGGAAKEHG
NSVCFKVDGGGGEEPAGSFEDAEGPRRQYGFMQRQFTSMLQPGVNKFSLR
MFGSQKAVEKEQERVKTAGFWIIHPYSDFRFYWDLIMLIMMVGNLVIIPV
GITFFTEQTTTPWIIFNVASDTVFLLDLIMNFRTGTVNEDSSEIILDPKV
IKMNYLKSWFVVDFISSIPVDYIFLIVEKGMDSEVYKTARALRIVRFTKI
LSLLRLLRLSRLIRYIHQWEEIFHMTYDLASAVVRIFNLIGMMLLLCHWD
GCLQFLVPLLQDFPPDCWVSLNEMVNDSWGKQYSYALFKAMSHMLCIGYG
AQAPVSMSDLWITMLSMIVGATCYAMFVGHATALIQSLDSSRRQYQEKYK
QVEQYMSFHKLPADMRQKIHDYYEHRYQGKIFDEENILSELNDPLREEIV
NFNCRKLVATMPLFANADPNFVTAMLSKLRFEVFQPGDYIIREGAVGKKM
YFIQHGVAGVITKSSKEMKLTDGSYFGEICLLTKGRRTASVPADTYCRLY
SLSVDNFNEVLEEYPMMRRAFETVAIDRLDRIGKKNSILLQKFQKDLNTG
YFNNQENEILKQIVKHDREMVQAIPPINYPQMTALNCTSSTTTPTSRMRT -continued QSPPVYTATSLSHSNLHSPSPSTQTPQPSAILSPCSYTTAVCSPPIQSPL
ATRTFHYASPTASQLSLMQQPQQQLPQSQVQQTQTQTQQQQQQQQQQQQQ
QQQQQQQQQQQQQQQQQQQQQQQQQPQTPGSSTPKNEVHKSTQALNNTNLT
KEVRPLSASQPSLPHEVSTLISRPHPTVGESLASIPQPVAAVHSTGLQAG
SRSTVPQRVTLFRQMSSGAIPPNRGVPPAPPPRAAVQRESPSVLNTDPDA
EKPRFASNL DNA and predicted amino acid sequence of mBCNG-2 GenBank Accession Number AF064873.

mBCNG-2 DNA sequence (SEQ ID NO:32)
AAGTTCTCCCTGCGGATGTTCGGCAGCCAGAAGGCCGTGGAGCGCGAGCA
GGAACGCGTGAAGTCGGCGGGGGCCTGGATCATCCACCCCTACAGCGACT
TCAGGTTCTACTGGGACTTCACCATGCTGTTGTTCATGGTGGGAAATCTC
ATTATCATTCCCGTGGGCATCACTTTCTTCAAGGACGAGACCACCGCGCC
CTGGATCGTCTTCAACGTGGTCTCGGACACTTTCTTCCTCATGGACTTGG
TGTTGAACTTCCGCACCGGCATTGTTATTGAGGACAACACGGAGATCATC
CTGGACCCCGAGAAGATAAAGAAGAAGTACTTGCGTACGTGGTTCGTGGT
GGACTTCGTGTCATCCATCCCGGTGGACTACATCTTCCTCATAGTGGAGA
AGGGAATCGACTCCGAGGTCTACAAGACAGCGCGTGCTCTGCGCATCGTG
CGCTTCACCAAGATCCTCAGTCTGCTGCGGCTGCTGCGGCTATCACGGCT
CATCCGATATATCCACCAGTGGGAAGAGATTTTCCACATGACCTACGACC
TGGCAAGTGCAGTGATGCGCATCTGTAACCTGATCAGCATGATGCTACTG
CTCTGCCACTGGGACGGTTGCCTGCAGTTCCTGGTGCCCATGCTGCAAGA
CTTCCCCAGCGACTGCTGGGTGTCCATCAACAACATGGTGAACCACTCGT
GGAGCGAGCTCTACTCGTTCGCGCTCTTCAAGGCCATGAGCCACATGCTG
TGCATCGGCTACGGGCGGCAGGCGCCCGAGAGCATGACAGACATCTGGCT
GACCATGCTCAGCATGATCGTAGGCGCCACCTGCTATGCCATGTTCATTG
GGCACGCCACTGCGCTCATCCAGTCCCTGGATTCGTCACGGCGCCAATAC
CAGGAGAAGTACAAGCAAGTAGAGCAATACATGTCCTTCCACAAACTGCC
CGCTGACTTCCGCCAGAAGATCCACGATTACTATGAACACCGGTACCAAG
GGAAGATGTCTGATGAGGACAGCATCCTTGGGGAACTCAACGGGCCACTG
CGTGAGGAGATTGTGAACTTCAACTGCCGGAAGCTGGTGGCTTCCATGCC
GCTGTTTGCCAATGCAGACCCCAATTTCGTCACAGCCATGCTGACAAAGC
TCAAATTTGAGGTCTTCCAGCCTGGAGATTACATCATCCGAGAGGGGACC
ATCGGGAAGAAGATGTACTTCATCCAGCATGGGGTGGTGAGCGTGCTCAC
CAAGGGCAACAAGGAGATGAAGCTGTCGGATGGCTCCTATTTCGGGGAGA
TCTGCTTGCTCACGAGGGGCCGGCGTACGGCCAGCGTGCGAGCTGACACC
TACTGTCGCCTCTACTCACTGAGTGTGGACAATTTCAACGAGGTGCTGGA -continued

GGAATACCCCATGATGCGGCGTGCCTTTGAGACTGTGGCTATTGACCGGC

TAGATCGCATAGGCAAGAAGAACTCCACCTTGCTGCACAAGGTTCAGCAT

GATCTCAGCTCC mBCNG-2 predicted amino acid sequence (SEQ ID NO:33)
KFSLRMFGSQKAVEREQERVKSAGAWIIHPYSDFRFYWDFTMLLFMVGNL

IIIPVGITFFKDETTAPWIVFNVVSDTFFLMDLVLNFRTGIVIEDNTEII

LDPEKIKKKYLRTWFVVDFVSSIPVDYIFLIVEKGIDSEVYKTARALRIV

RFTKILSLLRLLRLSRLIRYIHQWEEIFHMTYDLASAVMRICNLISMMLL

LCHWDGCLQFLVPMLQDFPSDCWVSINNMVNHSWSELYSFALFKAMSHML

CIGYGRQAPESMTDIWLTMLSMIVGATCYAMFIGHATALIQSLDSSRRQY

QEKYKQVEQYMSFHKLPADFRQKIHDYYEHRYQGKMSDEDSILGELNGPL

REEIVNFNCRKLVASMPLFANADPNFVTAMLTKLKFEVFQPGDYIIREGT

IGKKMYFIQHGVVSVLTKGNKEMKLSDGSYFGEICLLTRGRRTASVRADT

YCRLYSLSVDNFNEVLEEYPMMRRAFETVAIDRLDRIGKKNSTLLHKVQH

DLSS

DNA and predicted amino acid sequence of mBCNG-3 GenBank Accession Number AF064874.

mBCNG-3 DNA sequence (SEQ ID NO:34)
TGCGAGCAGCCCTCGGCGGACACCGCTATCAAAGTGGAGGGAGGCGCGGC

CGCCATCGACCATATCCTCCCCGAGGCCGAGGTGCGCCTGGGCCAAAGCG

GCTTCATGCAGCGCCAGTTCGGTGCCATGCTGCAACCTGGGGTCAACAAA

TTCTCCCTAAGGATGTTCGGCAGCCAGAAAGCGGTGGAGCGCGAGCAGGA

GAGGGTTAAGTCAGCAGGGTTTTGGATTATCCACCCCTACAGTGACTTCA

GATTTTACTGGGACCTGACGATGCTGTTGCTGATGGTGGGGAATCTGATC

ATCATACCCGTGGGCATCACCTTCTTCAAGGATGAGAACACCACACCCTG

GATCGTCTTCAATGTGGTGTCAGACACATTCTTCCTCATTGACTTGGTCC

TCAACTTCCGCACGGGGATCGTGGTGGAGGACAACACAGAAATCATCCTT

GACCCGCAGAGGATCAAGATGAAGTACCTGAAAAGCTGGTTTGTGGTAGA

TTTCATCTCCTCCATACCTGTCGAATACATTTTCCTTATAGTGGAGACTC

GCATTGACTCGGAGGTTTACAAAACCGCTAGGGCTGTGCGCATTGTCCGT

TTCACTAAGATCCTCAGCCTCCTGCGCCTCTTGAGGCTTTCCCGCCTCAT

TCGATACATTCATCAGTGGGAAGAGATTTTCCACATGACCTATGACCTGG

CCAGCGCCGTGGTACGCATCGTGAACCTCATTGGCATGATGCTTCTGCTG

TGTCACTGGGATGGCTGCCTGCAGTTCCTAGTGCCCATGCTGCAGGACTT

CCCCCATGACTGCTGGGTGTCCATCAATGGCATGGTGAATAACTCCTGGG

GGAAGCAGTATTCCTACGCCCTCTTCAAGGCCATGAGCCACATGCTGTGC

ATTGGGTATGGACGGCAGGCACCCGTAGGCATGTCTGACGTCTGGCTCAC

CATGCTCAGCATGATCGTGGGGGCCACCTGCTATGCCATGTTCATCGGCC

ACGCCACTGCCCTCATCCAGTCGCTAGACTCCTCCCGGCGCCAGTACCAG

-continued

GAGAAGTATAAACAGGTGGAGCAGTACATGTCTTTCCACAAGCTCCCGCC

TGACACCCGACAGCGCATCCATGACTACTATGAACACCGTTACCAAGGCA

AGATGTTTGATGAGGAAAGCATCCTGGGTGAGTTGAGTGAGCCACTTCGA

GAGGAGATCATCAACTTTAACTGCCGAAAGCTGGTGGCATCCATGCCACT

GTTTGCCAACGCAGATCCCAACTTTGTGACATCCATGCTGACCAAGTTGC

GTTTCGAGGTCTTCCAGCCTGGGGATTACATCATCCCCGAAGGCACCATC

GGCAAGAAGATGTACTTTATCCAGCACGGCGTGGTCAGCGTGCTCACTAA

GGGCAACAAAGAGACCAGGCTGGCTGATGGCTCCTATTTTGGAGAGATCT

GCTTGCTGACCCGGGGTCGGCGCACAGCCAGCGTCAGAGCGGATACTTAT

TNCCGCCTCTACTCACTG mBCNG-3 predicted amino acid sequence (SEQ ID NO:35)
CEQPSADTAIKVEGGAAAIDHILPEAEVRLGQSGFMQRQFGAMLQPGVNK

FSLRMFGSQKAVEREQERVKSAGFWIIHPYSDFRFYWDLTMLLLMVGNLI

IIPVGITFFKDENTTPWIVFNVVSDTFFLIDLVLNFRTGIVVEDNTEIIL

DPQRIKMKYLKSWFVVDFISSIPVEYIFLIVETRIDSEVYKTARAVRIVR

FTKILSLLRLLRLSRLIRYIHQWEEIFHMTYDLASAVVRIVNLIGMMLLL

CHWDGCLQFLVPMLQDFPHDCWVSINGMVNNSWGKQYSYALFKAMSHMLC

IGYGRQAPVGMSDVWLTMLSMIVGATCYAMFIGHATALIQSLDSSRRQYQ

EKYKQVEQYMSFHKLPPDTRQRIHDYYEHRYQGKMFDEESILGELSEPLR

EEIINFNCRKLVASMPLFANADPNFVTSMLTKLRFEVFQPGDYIIREGTI

GKKMYFIQHGVVSVLTKGNKETRLADGSYFGEICLLTRGRRTASVRADTY

XRLYSL

DNA and Predicted amino acid sequence of mBCNG-4 Reported are the complete DNA sequence of clone M28-EST, and the open reading frame (ORF) encoded between positions 632 and 871 of that DNA sequence. GenBank accession number AF064875.

mBCNG-4 DNA sequence (SEQ ID NO:36)
TTTTTGGGTTTTAAAATTTATTTTATTTTTAAAAGCGTCTCCGGANANTC

TAGTGCATGGCCAGGCTACAAGCTACTGGGCCAGCAACTCTGTAGGATTA

TTAATGACAAAAATGCAAGGACCCCATAGTTGATGGAAACCCAGGGATGA

AGCAGGGCTGTCCCACAGACTTAGGCTTTGTGGAGCTGTCTGAAAACCCA

GGCTGTGGCTTTGGAAGAAGTGCAGACAACCACTGCCCAGAGTGACTTAA

GGTTCATACAACCATCCAGCCACCTAAGCACCCCTACCTTCAAGCATCTT

GCCAGTCCCACTTTGTGTCTGTTTAGCCTGCTTTTCTCCTCCCAGTTAGG

AGTCGGGTACACCCTGGGACGGAGCAATAAGACTGGGGTTGGAGTTAATG

TGTAAAATAACTGAAAAAAACATCTGGGGCTGGCAAACCTGTTTGTCTGG

AAAACAGCCTTCCAGATGTGCAGGTATGGAAACAGACAGTGCTTAGAGCA

GTAAGGGACCTTATACCAGCTAATCGTTCATTCTCCCAAGTATAAGGAGG

-continued

AATCTGGGGGTGCTGGGTTAGCTGCTGCAGGCCTAATTGGGGGGTGGAAT

GGGAGCTCTGAGCTCTTCCCCGCTTTCGCAGAGATCTGCCTGCTGACTCG

AGGTCGGAGAACAGCCAGTGTAAGGGCTGACACCTATTGTCGCCTCTACT

CGCTCAGCGTGGACCACTTCAATGCGGTGCTTGAGGAGTTCCCAATGATG

CGCAGGGCTTTTGAGACGGTGGCCATGGACCGGCTTCGGCGCATCGGTGA

GGCCTGTTTACTCTGTCTGCTCTGGGTCCTGGCTGGGCCTCATCTCATGA

GCCTAGCCCTGGTGCTTTGACACCACATCCCAGCCCACCCAGTTCCAGTC

CATGCCTCCAGCAGGCTGTTAGCACTGTTGCTCACTAGACTTAGCCCTAG

CGAGAAATTGCCGTGGAGTGTCTCCCCAAACCCTCATTCCCCGTGTCCTT

CTGGGTACCAGTTCTTAACCTCACAATTTTTTATTGATA mBCNG-4 predicted amino acid sequence (SEQ ID NO:37)
EICLLTRGRRTASVRADTYCRLYSLSVDHFNAVLEEFPMMRRAFETVAMD

RLRRIGEACLLCLLWVLAGPHLMSLALVL

Human Sequences:

DNA and predicted amino acid sequence of hBCNG-1 GenBank accession number AF064876.

hBCNG-1 DNA sequence (SEQ ID NO:38)
AAGGAGCAGGAAAGGGTTAAAACTGCAGGCTTCTGGATTATCCACCCTTA

CAGTGATTTCAGGTTTTACTGGGATTTAATAATGCTCATAATGATGGTTG

GAAATCTAGTCATCATACCAGTTGGAATCACATTCTTTACAGAGCAAACA

ACAACACCATGGATTATTTTCAATGTGGCATCAGATACAGTTTTCCTATT

GGACCTGATCATGAATTTTAGGACTGGGACTGTCAATGAAGACAGTTCTG

AAATCATCCTGGACCCCAAAGTGATCAAGATGAATTATTTAAAAAGCTGG

TTTGTGGTTGACTTCATCTCATCCATCCCAGTGGATTATATCTTTCTTAT

TGTAGAAAAAGGAATGGATTCTGAAGTTTACAAGACAGCCAGGGCCCTTC

GCATTGTGAGGTTTACAAAAATTCTCAGTCTCTTGCGTTTATTACGACTT

TCAAGGTTAATTAGATACATACATCAATGGGAAGAGATATTCCACATGAC

ATATGATCTCGCCAGTGCAGTGGTGAGAATTTTTAATCTCATCGGCATGA

TGCTGCTCCTGTGCCACTGGGATGGTTGTCTTCAGTTCTTAGTACCACTA

CTGCAGGACTTCCCACCAGATTGCTGGGTGTCTTTAAATGAAATGGTTAA

TGATTCTTGGGGAAAGCAGTATTCATACGCACTCTTCAAAGCTATGAGTC

ACATGCTGTGCATTGGGTATGGAGCCCAAGCCCCAGTCAGCATGTCTGAC

CTCTGGATTACCATGCTGAGCATGATCGTCGGGGCCACCTGCTATGCCAT

GTTTGTCGGCCATGCCACCGCTTTAATCCAGTCTCTGGATTCTTCGAGGC

GGCAGTATCAAGAGAAGTATAAGCAAGTGGAACAATACATGTCATTCCAT

AAGTTACCAGCTGATATGCGTCAGAAGATACATGATTACTATGAACACAG

ATACCAAGGCAAAATCTTTGATGAGGAAAATATTCTCAATGAACTCAATG

ATCCTCTGAGAGAGGAGATAGTCAACTTCAACTGTCGGAAACTGGTGGCT

ACAATGCCTTTATTTGCTAATGCGGATCCTAATTTTGTGACTGCCATGCT

-continued

GAGCAAGTTGAGATTTGAGGTGTTTCAACCTGGAGATTATATCATACGAG

AAGGAGCCGTGGGTAAAAAAATGTATTTCATTCAACACGGTGTTGCTGGT

GTCATTACAAAATCCAGTAAAGAAATGAAGCTGACAGATGGCTCTTACTT

TGGAGAGATTTGCCTGCTGACCAAAGGACGTCGTACTGCCAGTGTTCGAG

CTGATACATATTGTCGTCTTTACTCACTTTCCGTGGACAATTTCAACGAG

GTCCTGGAGGAATATCCAATGATGAGGAGAGCCTTTGAGACAGTTGCCAT

TGACCGACTAGATCGAATAGGAAAGAAAAATTCAATTCTTCTGCAAAAGT

TCCAGAAGGATCTGAACACTGGTGTTTTCAACAATCAGGAGAACGAAATC

CTCAAGCAGATTGTGAAACATGACAGGGAGATGGTGCAGGCAATCGCTCC

CATCAATTATCCTCAAATGACAACCCTGAATTCCACATCGTCTACTACGA

CCCCGACCTCCCGCATGAGGACACAATCTCCACCGGTGTACACAGCGACC

AGCCTGTCTCACAGCAACCTGCACTCCCCCAGTCCCAGCACACAGACCCC

CCAGCCATCAGCCATCCTGTCACCCTGCTCCTACACCACCGCGGTCTGCA

GCCCTCCTGTACAGAGCCCTCTGGCCGCTCGAACTTTCCACTATGCCTCC

CCCACCGCCTCCCAGCTGTCACTCATGCAACAGCAGCCGCAGCAGCAGGT

ACAGCAGTCCCAGCCGCCGCAGACTCAGCCACAGCAGCCGTCCCCGCAGC

CACAGACACCTGGCAGCTCCACGCCGAAAAATGAAGTGCACAAGAGCACG

CAGGCGCTTCACAACACCAACCTGACCCGGGAAGTCAGGCCATTTTCCGC

CTGGCAGCCNTCGCTGCCCCATGAGGTGTCCATTTTGATTTCCAGACCCA

TCCCACTGTGGGGGAGTCCCTGGCCTCCATCCCTCAACCCGTGACGGCGG

TCCCCGGAACGGGCCTTCAGGCAGGGGGCAGGAGCACTGTCCCGCAGCGC

GTCACCTTTTTCCGACAGATGTNGTCGGGAGCCATCCCCCCGAACCGAGG

AGTCCTTCCAGCACCCCTTCCACTTATCACACCCCATCCTAAAAAA hBCNG-1 predicted amino acid sequence (SEQ ID NO:39)
KEQERVKTAGFWIIHPYSDFRFYWDLIMLIMMVGNLVIIPVGITFFTEQT

TTPWIIFNVASDTVFLLDLIMNFRTGTVNEDSSEIILDPKVIKMNYLKSW

FVVDFISSIPVDYIFLIVEKGMDSEVYKTARALRIVRFTKILSLLRLLRL

SRLIRYIHQWEEIFHMTYDLASAVVRIFNLIGMMLLLCHWDGCLQFLVPL

LQDFPPDCWVSLNEMVNDSWGKQYSYALFKAMSHMLCIGYGAQAPVSMSD

LWITMLSMIVGATCYAMFVGHATALIQSLDSSRRQYQEKYKQVEQYMSFH

KLPADMRQKIHDYYEHRYQGKIFDEENILNELNDPLREEIVNFNCRKLVA

TMPLFANADPNFVTAMLSKLRFEVFQPGDYIIREGAVGKKMYFIQHGVAG

VITKSSKEMKLTDGSYFGEICLLTKGRRTASVRADTYCRLYSLSVDNFNE

VLEEYPMMRRAFETVAIDRLDRIGKKNSILLQKFQKDLNTGVFNNQENEI

LKQIVKHDREMVQAIAPINYPQMTTLNSTSSTTTPTSRMRTQSPPVYTAT

SLSHSNLHSPSPSTQTPQPSAILSPCSYTTAVCSPPVQSPLAARTFHYAS

PTASQLSLMQQQPQQQVQQSQPPQTQPQQPSPQPQTPGSSTPKNEVHKST

QALHNTNLTREVRPFSAWQPSLPHEVSILISRPHPTVGESLASIPQPVTA

VPGTGLQAGGRSTVPQRVTFFRQMXSGAIPPNRGVLPAPLPLITPHPKK

DNA and predicted amino acid sequence (Seq I.D. No. 40) of hBCNG-2 GenBank accession number AF064877.

hBCNG-2 DNA sequence

```
GCGAGGAGGCGGGCCCGGCGGGGGAGCCGCGCGGCAGCCAGGCCAGCTTC

ATGCAGCGCCAGTTCGGCGCGCTCCTGCAGCCGGGCGTCAACAAGTTCTC

GCTGCGGATGTTCGGCAGCCAGAAGGCCGTGGAGCGCGAGCAGGAGCGCG

TCAAGTCGGCGGGGGCCTGGATCATCCACCCGTACAGCGACTTCAGGTTC

TACTGGGACTTCACCATGCTGCTGTTCATGGTGGGAAACCTCATCATCAT

CCCAGTGGGCATCACCTTCTTCAAGGATGAGACCACTGCCCCGTGGATCG

TGTTCAACGTGGTCTCGGACACCTTCTTCCTCATGGACCTGGTGTTGAAC

TTCCGCACCGGCATTGTGATCGAGGACAACACGGAGATCATCCTGGACCC

CGAGAAGATCAAGAANAAGTATCTGCGCACGTGGTTCGTGGTGGTCTTCG

TGTCCTCCATCCCCGTGGACTACATCTTCCTTATCGTGGAGAAGGGCATT

GACTCCGAGGTCTACAAGACGGCACGCGCCCTGCGCATCGTGCGCTTCAC

CAAAATCCTCAGCCTCCTGCGGCTGCTGCGCCTCTCACGCCTGATCCGCT

ACATCCATCAGTGGGAGGAGATCTTCCACATGACCTATGACCTGGCCAGC

GCGGTGATGAGGATCTGCAATCTCATCAGCATGATGCTGCTGCTCTGCCA

CTGGGACGGCTGCCTGCAGTTCCTGGTGCCTATGCTGCAGGACTTCCCGC

GCAACTGCTGGGTGTCCATCAATGGCATGGTGAACCACTCGTGGAGTGAA

CTGTACTCCTTCGCACTCTTCAAGGCCATGAGCCACATGCTGTGCATCGG

GTACGGCCGGCAGGCGCCCGAAAGCATGACGGACATCTGGCTGACCATGC

TCAGCATGATTGTGGGTGCCACCTGCTACGCCATGTTCATCGGCCACGCC

ACTGCCCTCATCCAGTCGCTGGACTCCTCGCGGCGCCAGTACCAGGAGAA

GTACAAGCAGGTGGAGCAGTACATGTCCTTCCACAAGCTGCCAGCTGACT

TCCGCCAGAAGATCCACGACTACTATGAACACCGTTACCAGGGCAAGATG

TTTGACGAGGACAGCATCCTGGGCGAGCTCAACGGGCCCCTGCGGGAGGA

GATCGTCAACTTCAACTGCCGGAAGCTGGTGGCCTCCATGCCGCTGTTCG

CCAACGCCGACCCCAACTTCGTCACGGCCATGCTGACCAAGCTCAAGTTC

GAGGTCTTCCAGCCGGGTGACTACATCATCCGCGAAGGCACCATCGGGAA

GAAGATGTACTTCATCCAGCACGGCGTGGTCAGCGTGCTCACTAAGGGCA

ACAAGGAGATGAAGCTGTCCGATGGCTCCTACTTCGGGGAGATCTGCCTG

CTCACCCGGGGCCGCCGCACGGCGANCGTGCGGGCTGACACCTACTGCCG

CCTCTATTCCCTGAGCGTGGACAACTTCAACGAAGTGCTGGAGGAGTACC

CCATGATGCGGCGCGCTTTCGAGACGGTGGCCATCGACCGCCTGGACCGC

ATCGGCAAGAAGAATTCCATCCTCCTGCACAAGGTGCAGCATGACCTCAA

CTCGGGCGTATTCAACAACCAGGAGAACGCCATCATCCAGGAGATCGTCA

AGTACGACCGCGAGATGGTGCAGCAGGCCGAGCTGGGTCAGCGCGTGGGC

TTTTTCCCGCCGCCGCCGCCGCCGCCGCAGGTCACTTCGGCCATCGCCAC

GCTGCAGCAGGCGGCGGCCATGAGCTTCTGCCCGCAGGTGGC
```

hBCNG-2 predicted amino acid sequence (SEQ ID NO:41)

-continued

```
EEAGPAGEPRGSQASFMQRQFGALLQPGVNKFSLRMFGSQKAVEREQERV

KSAGAWIIHPYSDFRFYWDFTMLLFMVGNLIIIPVGITFFKDETTAPWIV

FNVVSDTFFLMDLVLNFRTGIVIEDNTEIILDPEKIKXKYLRTWFVVVFV

SSIPVDYIFLIVEKGIDSEVYKTARALRIVRFTKILSLLRLLRLSRLIRY

IHQWEEIFHMTYDLASAVMRICNLISMMLLLCHWDGCLQFLVPMLQDFPR

NCWVSINGMVNHSWSELYSFALFKAMSHMLCIGYGRQAPESMTDIWLTML

SMIVGATCYAMFIGHATALIQSLDSSRRQYQEKYKQVEQYMSFHKLPADF

RQKIHDYYEHRYQGKMFDEDSILGELNGPLREEIVNFNCRKLVASMPLFA

NADPNFVTAMLTKLKFEVFQPGDYIIREGTIGKKMYFIQHGVVSVLTKGN

KEMKLSDGSYFGEICLLTRGRRTAXVRADTYCRLYSLSVDNFNEVLEEYP

MMRRAFETVAIDRLDRIGKKNSILLHKVQHDLNSGVFNNQENAIIQEIVK

YDREMVQQAELGQRVGFFPPPPPPPQVTSAIATLQQAAAMSFCPQVA
```

References

Adelman, J. P., Shen, K.-Z., Kavanaugh, M. P., Warren, R. A., Wu, Y.-N., Lagrutta, A., Bond, C. T., & North, R. A. (1992) Neuron 9, 209–216.

Adelman, J. P. (1995) Current Opinion in Neurobiology 5, 286–295.

Aiba, H., Fujimoto, S. and Ozaki, N. (1982) *Nucleic Acids Res.* 10:1345–1361.

Anderson, J. A., Huprikar, S. S., Kochian, L. V., Lucas, W. J. and Gaber, R. F. (1992) *Proc. Natl. Acad. Sci.* 89:3736–3740.

Arancio, O., Kandel, E. R., & Hawkins, R. D. (1995) Nature 376, 74–80.

Atkinson, N. S., Robertson, G. A., & Ganetzky, B. (1991) Science 253, 551–555.

Ausubel, F. M., Brent, R., Kingston, R. E., Moore, D. D., Seidman, J. G., Smith, J. A.,& Struhl, K. (1994) Current Protocols in Molecular Biology (John Wiley and Sons, New York, NY).

Baker, K., Warren, K. S., Yellen, G., and Fishman, M. C. (1997). Defective "pacemaker" current ($I_h$) in a zebrafish mutant with a slow heart rate. Proc. Natl. Acad. Sci. USA 94, 4554–4559.

Barhanin, J., Lesage, F., Guillemare, E., Fink, M., Lazdunski, M. & Romey, G. (1996) Nature 384:78–80.

Barton, S. K. et al., 1992 *J. Am. Chem. Soc.* 114:8736–40.

Bigger, J. T. Jr. and Reiffel, J. A. (1979). Sick sinus syndrome. Annu. Rev. Med. 30, 91–118.

Bois, P., Renaudon, B., Baruscotti, M., Lenfant, J., and DiFrancesco, D. (1997). J. Physiol. (Lond) 501, 565–571.

Bolshakov, V. Y., Golan, H., Kandel, E. R., & Siegelbaum, S. A.(1997) Neuron 19,635–651.

Bradley, J., Li, J., Davidson, N., Lester, H. A., & Zinn, K. (1994) Proc. Natl. Acad. Sci USA 91, 8890–8894.

Bradley, J., Zhang, Y, Bakin, R., Lester, H. A., Ronnett, G. V., & Zinn, K. (1997) J. of Neurosci. 17, 1993–2005.

Breede, L., & Nasmyth, K. (1985) Cold Spring Harbor Symp. Quant. Biol. 50, 643–650.

Broillet, M. C. & Firestein, S. (1997) *Neuron* 18: 951–958.

Brown, H. F., DiFrancesco, D., and Noble, S. J. (1979). Nature 280, 235–236.

Brown, H. and DiFrancesco, D. (1980). J. Physiol. (Lond) 308, 331–351.

Brugge, J. S., Cotton, P. C., Querel, A. E., Barrett, J. N., Nonner, D., & Keane, R. W. (1985) Nature 316, 554–557.

Bruggemann, A., Pardo, L., Stuhmer, W., & Pongs, O. (1993) Nature 365, 445–448.

Buller, A. L. and White, M. M. (1990). Mol. Pharmacol. 37, 423–428.

Cerbai, E., Pino, R., Porciatti, F., Sani, G., Toscano, M., Maccherini, M., Giunti, G., and Mugelli, A. (1997). Circulation 95, 568–571.

Cerbai, E., Barbieri, M., and Mugelli, A. (1994). J. Physiol. (Lond) 481, 585–591.

Cerbai, E. et al. (1997) J. Physiol. (Lond) 492, 97–106.

Chang, F., Cohen, I. S., DiFrancesco, D., Rosen, M. R, and Tromba, C. (1991). J. Physiol. (Lond) 440, 367–384.

Chen, T. Y., Peng, Y. W., Dhallan, R. S., Ahamed, B., Reed, R. R, & Yau K. W. (1993) Nature 362, 764–767.

Cossart, P. and Gicquel-Sanzey, B. (1982) *Nucleic Acids Res.* 10: 1363–1378.

Dale, R. N. K. et al., 1973 *Proc. Natl. Acad. Sci. USA* 70:2238–42.

Dekin, M. S. (1993). J. Neurophysiol. 70, 590–601.

Demo, S. D. and Yellen, G. (1991). Neuron 7, 743–753.

Dhallan, R. S., Yau, K. W., Schrader, K. A., and Reed, R. R. (1990) Nature 347, 184–187.

DiFrancesco, D. and Tortora, P. (1991). Nature 351, 145–147.

DiFrancesco, D., Porciatti, F., and Cohen, I. S. (1991).

Experientia 47, 449–452.

DiFrancesco, D. (1986). Nature 324, 470–473.

DiFrancesco, D. (1993). Annu. Rev. Physiol. 55, 455–472.

DiFrancesco, D. (1984). J. Physiol. (Lond) 348, 341–367.

DiFrancesco, D., Ojeda, C. (1980). J. Physiol. (Lond) 308, 353–367.

DiFrancesco, D. and Mangoni, M. (1994). J. Physiol. (Lond) 474, 473–482.

DiFrancesco, D., Ferroni, A., Mazzanti, M., and Tromba, C. (1986). J. Physiol. (Lond) 377, 61–88.

DiFrancesco, D., Ducouret, P., and Robinson, R. B. (1989). Science 243, 669–671.

DiFrancesco, D. (1981). J. Physiol. (Lond) 314, 359–376.

DiFrancesco, D. (1995). Cardiovasc. Res. 30, 307–308.

Doyle, D. A., Cabral, J. M., Pfuetzner, R. A., Kuo, A., Gulbis, J. M., Cohen, S. L., Chait, B. T., and MacKinnon, R. (1998). Science 280, 69–77.

Erickson, P. F. et al., 1982 *J. Inmunol. Methods* 51:241–49.

Fields S., & Song O. K. (1989) Nature 340, 245–246.

Frangioni, J. V., & Neel, B. G. (1993) Anal. Biochem. 210, 179–187.

Frey, U, Huang, Y.-Y., & Kandel, E. R. (1993) Science 260, 1661–1664.

Goulding, E. H., Ngai, J., Kramer, R. H., Colicos, S., Axel, R., Siegelbaum, S. A. and Chess, A. (1992) *Neuron* 8:45–58.

Goulding, E. H., Tibbs, G. R. and Siegelbaum, S. A. (1994) *Nature* 372:369–374.

Grant, S. G. N., Karl, K. A., Kiebler, M., & Kandel, E. R. (1995) Genes Dev. 9, 1909–1921.

Greene,W. N., & Millar, N. S. (1995) Trends Neurosci. 18, 280–287.

Halliwell, J. V. and Adams, P. R. (1982). Brain. Res. 250, 71–92.

Harlow, E., & Lane, D. (1988) Antibodies: a laboratory manual (Cold Spring Harbor Lab. Press, Cold Spring Harbor, N.Y.).

Hedin, K. E., Lim, N. F., and Clapham, D. E. (1996). Neuron 16, 423–429.

Heginbotham, L., Lu, Z., Abramson, T., and MacKinnon, R. (1994). Biophys. J. 66, 1061–1067.

Hille, B. (1992). Ionic Channels of Excitable Membranes. Sinauer.

Hoshi, T. (1995) J. Gen. Physiol. 105, 309–328.

Huang Y.-Y., & Kandel E. R. (1994) Learning & Memory 1:74–82.

Inagaki, N., Gonoi, T., Clement, J. P., Wang, C. Z., Aguilar-Bryan, L., Bryan, J. & Seino, S. (1996) *Neuron* 16:1011–1017.

Ingram, S. L. and Williams, J. T. (1996). J. Physiol. (Lond) 492, 97–106.

Irisawa, H., Brown, H. F., and Giles, W. (1993). Physiol. Rev. 73, 197–227.

Isomoto, S., Kondo, C., Yamada, M., Matsumoto, S., Higashiguchi, O., Horio, Y., Matsuzawa, Y. & Kurachi, Y. (1996) *J Biol Chem* 271:24321–24324.

Jan, L. Y. and Jan, Y. N. (1997). Annu. Rev. Neurosci. 20, 91–123.

Jegla, T. & Salkoff, L. *J. Neurosci* (1997) 17, 32–44.

Johnson, S. M. and Getting, P. A. (1991). J. Neurophysiol. 66, 744–761.

Johnson, T. K. et al., 1983 *Anal. Biochem.* 133:125–131.

Kamb, A., Iverson, L. E., & Tanouye, M. A. (1987) Cell 50, 405–413.

Kaupp, U. B., Niidome, T, Tanabe, T., Terada, S., Bönigk, W., Stühmer, W., Cook, N.J., Kangawa, K., Matsuo, H., Hirose, T., Miyata, T., & Numa, S. (1989) Nature 342, 762–766.

Kingston, P. A., Zufall, F., & Barnstable, C. J. (1996) Proc. Natl. Acad. Sci. USA 93,10440–10445.

Kohler, M., Hirschberg, B., Bond, C. T., Kinzie, J. M., Marrion, N. V., Maylie, J., & Adelman, J. P. (1996) Science 273, 1709–1714.

Kramer, R. H. and Tibbs, G. R. (1996) *J. Neurosci.* 16:1285–1293.

Krapivinsky, G., Krapivinsky, L., Wickman, K., & Clapham, D. E. (1995) J. Biol. Chem. 270,29059–29062.

Kumar, V. D. and Weber, I. T. (1992) *Biochemistry* 31:4643–4649.

Lidofsky, S. D. (1996) *J. Membr. Biol.* 157, 231–236.

Liman, E. R., & Buck, L. B. (1994) Neuron 13, 1–20.

Liman, E. R., Hess, P., Weaver, F. & Koren, G. *Nature* (1991) 353: 752–756.

Maccaferri, G., Mangoni, M., Lazzari, A., and DiFrancesco, D. (1993). J. Neurophysiol. 69, 2129–2136.

Maccaferri, G. and McBain, C.J. (1996). J. Physiol. (Lond) 497, 119–130.

MacKinnon, R. (1991). Nature 350, 232–235.

Martinez, R., Mathey-Prevot, B., Bernards, A., & Baltimore, D. (1987) Science 237, 411–415.

Matthaei, F. S. et al., (1986) *Anal. Biochem.* 157:123–128.

Marunaka, Y. et al. (1991) Biochim. Biophys. Acta 1070, 152–156.

Mayer, M. L. and Westbrook, G. L. (1983). J. Physiol. (Lond) 340, 19–45.

Mayford, M., Wang, J., Kandel, E. R., & O'Dell, T. J. (1995) Cell 81:891–904.

McCormick, D. A. and Bal, T. (1997). Annu. Rev. Neurosci. 20, 185–215.

McCormick, D. A. and Pape, H. C. (1990). J. Physiol. (Lond) 431, 291–318.

McDonald, T. V., Yu, Z., Ming, Z., Palma, E., Meyers, M. B., Wang, K. W., Goldstein, S. A. & Fishman, G. I. (1997) Nature 388:289–292.

Miller, A. G. and Aldrich, R. W. (1996). Neuron 16, 853–858.

Noma, A., Morad, M, and Irisawa, H. (1983). Pflugers Arch. 397, 190–194.

Palay, S. L., & Chan-Palay, V. (1974) Cerebellar cortex: cytology and organization (Springer, New York, N.Y.).

Pallanck, L., & Ganetzky, B. (1994) Hum. Mol. Genet. 3, 1239–1243.

Papazian, D. M., Tempe, L. C., Jan, Y. N., & Jan, L. Y. (1991) Nature 349:305–310.

Papazian, D. M., Schwartz, T. L., Tempel, B. L., Jan, Y. N., & Jan, L. Y. (1987) Science 237, 749–753.

Pape, H. C. and McCormick, D. A. (1989). Nature 340, 715–718.

Pape, H. C. (1996). Annu. Rev. Physiol. 58, 299–327.

Pawson, T. (1995) Nature 373, 573–580.

Pedarzani, P., & Storm, J. F. (1995) Proc. Natl. Acad. Sci. USA 92, 11716–11720.

Pedarzani, P., & Storm, J. F. (1995) Proc. Natl. Acad. Sci. USA 92, 11716–11720.

Pongs, O., (1992) Physiol. Rev. 72: S69–S88.

Raisman, G., Cowan, W-. M., & Powell, T. P. S. (1965) Brain 88:963–996.

Robinson, R. B., Yu, H., Chang, F., and Cohen, I. S. (1997). Pflugers Arch. 433, 533–535.

Roden, D. (1996). Antiarryhthmic drugs. In, The Pharmacological Basis of Therapeutics, ninth ed. Eds, Hardman, J. G., Limbird, L. E. McGraw Hill, New York.

Sambrook, J., Fritsch, E. F., and Maniatis, T. (1989). Molecular Cloning: A Laboratory Manual, 2nd Ed. (Cold Spring Harbor Laboratory Press).

Sanguinetti, M. C., Jiang, C., Curran, M. E., and Keating, M. T. (1995). Cell 81, 299–307.

Santoro, B., Grant, S. G. N., Bartsch, D., and Kandel, E. R. (1997). Proc. Natl. Acad. Sci. USA 94, 14815–14820.

Schlack W. et al. (1998) Arzneimittelforschung 1998 Jan; 48(1):26–33.

Schachtman, D. P., Schroeder, J. I., Lucas, W. J., Anderson, J. A., and Gaber, R. F. (1994). Science 258, 1654–1658.

Scott, S.-P., Harrison, R. W., Weber, I. T. and Tanaka, J. C. (1996) *Protein Engineering* 9:333–344.

Sentenac, H., Bonneaud, N., Minet, M., Lacroute, F., Salmon, J.-M., Gaymard, F. and Grignon, C. (1992) *Science* 256:663–665.

Shabb, J. B. and Corbin, J. D. (1992) *J. Biol. Chem.* 267, 5723–5726.

Sheng, M., Tsaur, M.-L., Jan, Y. N., & Jan, L. Y. (1994) J. Neurosci. 14, 2408–2417.

Singer, W. and Gray, C. M. (1995). Annu. Rev. Neurosci. 18, 555–586.

Smith, P. L., Baukrowitz, T., and Yellen, G. (1996). Nature 379, 833–836.

Spellberg, R. D. (1971). Chest 60, 246–251.

Staub, O., Dho, S., Henry, P. C., Correa, J., Ishikawa, T., McGlade, J., & Rotin, D. (1996) EMBO J. 15, 2371–2380.

Strata, F., Atzori, M., Molnar, M., Ugolini, G., Tempia, F., and Cherubini, E. (1997). J. Neurosci. 17, 1435–1446.

Strong, M., Chandy, G., & Gutman, G. (1993) Mol. Biol. Evol. 10, 221–242.

Su, Y., Dostmann, W. R. G., Herberg, F. W., Durick, K., Xuong, N-H., Ten Eyck, L., Taylor, S. S. and Varughese, K. I. (1995) *Science* 269:807–813.

Sudol, M. (1996) TIBS 21, 161–163.

Sugrue, M. M., Brugge, J. S., Marshak, D. R., Greengard, P., & Gustafson, E. L. (1990) J. Neurosci. 10, 2513–2527.

Thomas M. J., Moody T. D., Makhinson M., and O'Dell, T. J. (1996) Neuron 17, 475–482.

Tibbs, G. R., Liu, D. T., Leypold, B. G., and Siegelbaum, S. A. (1998). J. Biol. Chem. 273, 4497–4505.

Titani, K., Sasagawa, T., Ericsson, L. H., Kumar, S., Smith, S. B., Krebs, E. G. and Walsh, K. A. (1984) *Biochemistry* 23:4193–4199.

Trudeau, M. C., Warmke, J. W., Ganetzky, B., and Robertson, G. A. (1995). Science 269, 92–95.

Tsien, R. W. (1974). J. Gen. Physiol. 64, 293–319.

Tzounopoulos, T., Maylie, J., and Adelman, J. P. (1995). Biophys. J. 69, 904–908.

Varnum, M. D., Black, K. D. and Zagotta, W. N. (1995) Neuron 15:619–625.

Vassalle, M. (1995). Cardiovasc. Res. 30, 309–310.

Wang, H., Kunkel, D. D., Schwartzkroin, P. A., & Tempel, B. L. (1994) J. Neurosci. 14, 4588–4599.

Warmke, J, Drysdale, R., & Ganetzky, B. (1991) Science 252, 1560–1562.

Warmke, J. W., & Ganetzky, B. (1994) Proc. Natl. Acad. Sci. USA 91, 3438–3442.

Weber, I. T., Shabb, J. B., & Corbin, J. D. (1989) Biochemistry 28, 6122–6127.

Weber, I. T. and Steitz, T. A. (1987) *J. Mol. Biol.* 198:311–326.

Wohlfart, P., Haase, W., Molday, R. S., & Cook, N. J. (1992) J. Biol. Chem. 267, 644–648.

Yanagihara, K., and Irisawa, H. (1980). Pflugers Arch. 385, 11–19.

Yu, H., Chang, F., and Cohen, I. S. (1993). Circ. Res. 72, 232–236.

Zagotta, W. N., & Siegelbaum, S. A. (1996) Annu. Rev. Neurosci. 19, 235–263.

Zaza, A., Robinson, R. B., and DiFrancesco, D. (1996). J. Physiol. (Lond) 491, 347–355.

Zervos, A. S., Gyuris, J., & Brent, R. (1993) Cell 72, 223–232.

What is claimed is:

1. An isolated protein comprising the amino acid sequence of mouse BCNG-1 (SEQ ID NO:31).

2. A cell comprising the protein of claim 1, wherein the cell does not naturally express the protein.

* * * * *